(12) United States Patent
Larsen et al.

(10) Patent No.: US 11,707,377 B2
(45) Date of Patent: Jul. 25, 2023

(54) COUPLING PART WITH A HINGE FOR A MEDICAL BASE PLATE AND SENSOR ASSEMBLY PART

(71) Applicant: Coloplast A/S, Humlebaek (DK)

(72) Inventors: Lars Erup Larsen, Maaloev (DK); Jais Ask Hansen, Jaegerspris (DK); Lars Stendevad Windeballe, Virum (DK)

(73) Assignee: Coloplast A/S, Humlebaek (DK)

( * ) Notice: Subject to any disclaimer, the term of this patent is extended or adjusted under 35 U.S.C. 154(b) by 281 days.

(21) Appl. No.: 16/954,211

(22) PCT Filed: Dec. 20, 2018

(86) PCT No.: PCT/DK2018/050408
§ 371 (c)(1),
(2) Date: Jun. 16, 2020

(87) PCT Pub. No.: WO2019/120452
PCT Pub. Date: Jun. 27, 2019

(65) Prior Publication Data
US 2021/0361464 A1   Nov. 25, 2021

(30) Foreign Application Priority Data

Dec. 22, 2017   (DK) .......................... PA 2017 70984
Dec. 22, 2017   (DK) .......................... PA 2017 70998
(Continued)

(51) Int. Cl.
*A61F 5/443*   (2006.01)
*A61F 5/44*   (2006.01)
(Continued)

(52) U.S. Cl.
CPC ...... *A61F 5/443* (2013.01); *A61F 2005/4486* (2013.01)

(58) Field of Classification Search
CPC ... A61F 5/443; A61F 2005/4486; A61F 5/445
See application file for complete search history.

(56) References Cited

U.S. PATENT DOCUMENTS 2,054,535 A   9/1936   Diack
2,327,514 A *   8/1943   Fenwick ................. A61F 5/445
604/338
(Continued)

FOREIGN PATENT DOCUMENTS

CN   203786580 U   8/2014
CN   104902399 A   9/2015
(Continued)

*Primary Examiner* — Guy K Townsend
(74) *Attorney, Agent, or Firm* — Coloplast Corp., Coloplast A/S; Nick Bauman

(57) ABSTRACT

Disclosed is a coupling part and a base plate comprising a coupling part. The coupling part comprises a first coupling part section and a second coupling part section. The first coupling part section being configured for attachment to a first part of the base plate, and the second coupling part section being configured for attachment to a second part of the base plate. The first coupling part section being hingedly attached to the second coupling part section allowing a rotational movement of the first coupling part section relative to the second coupling part section about a hinge-axis. The hinge axis being parallel to the first coupling part plane and the second coupling part plane.

14 Claims, 25 Drawing Sheets

(30) Foreign Application Priority Data

Feb. 20, 2018 (DK) .......................... PA 2018 70108
Jun. 4, 2018 (DK) .......................... PA 2018 70323

(51) Int. Cl.
*A61F 5/445* (2006.01)
*A61F 5/448* (2006.01)

(56) References Cited

U.S. PATENT DOCUMENTS

| | | | | |
|---|---|---|---|---|
| 2,542,233 | A * | 2/1951 | Carroll | A61F 5/445 604/337 |
| 2,544,579 | A * | 3/1951 | Ardnerfrankj | A61F 5/445 604/337 |
| 3,214,502 | A | 10/1965 | Schaar | |
| 3,832,510 | A | 8/1974 | Pfau et al. | |
| 3,915,171 | A * | 10/1975 | Shermeta | A61J 15/0065 D24/112 |
| 3,941,133 | A | 3/1976 | Chen | |
| 4,231,369 | A | 11/1980 | Sorensen et al. | |
| 4,372,308 | A | 2/1983 | Steer et al. | |
| 4,449,970 | A | 5/1984 | Bevan et al. | |
| 4,668,227 | A * | 5/1987 | Kay | A61F 5/442 604/277 |
| 4,754,264 | A | 6/1988 | Okada et al. | |
| 4,775,374 | A | 10/1988 | Cilento et al. | |
| 4,834,731 | A | 5/1989 | Nowak et al. | |
| 4,973,323 | A | 11/1990 | Kaczmarek et al. | |
| 4,982,742 | A | 1/1991 | Claude | |
| 5,013,307 | A | 5/1991 | Broida | |
| 5,016,645 | A | 5/1991 | Williams et al. | |
| 5,051,259 | A | 9/1991 | Olsen et al. | |
| 5,074,851 | A | 12/1991 | Plass et al. | |
| 5,111,812 | A | 5/1992 | Swanson et al. | |
| 5,167,650 | A | 12/1992 | Johnsen et al. | |
| 5,197,895 | A | 3/1993 | Stupecky | |
| 5,237,995 | A | 8/1993 | Cano | |
| 5,318,543 | A * | 6/1994 | Ross | A61J 15/0023 604/170.01 |
| 5,358,488 | A * | 10/1994 | Suriyapa | A61J 15/0015 604/910 |
| 5,486,158 | A | 1/1996 | Samuelsen | |
| 5,570,082 | A | 10/1996 | Mahgerefteh et al. | |
| 5,593,397 | A | 1/1997 | La Gro | |
| 5,626,135 | A * | 5/1997 | Sanfilippo | A61N 1/0492 600/394 |
| 5,672,163 | A * | 9/1997 | Ferreira | A61F 5/441 604/333 |
| 5,677,221 | A | 10/1997 | Tseng | |
| 5,704,905 | A | 1/1998 | Jensen et al. | |
| 5,790,036 | A | 8/1998 | Fisher et al. | |
| 5,800,415 | A | 9/1998 | Olsen | |
| 5,816,252 | A | 10/1998 | Faries, Jr. et al. | |
| 5,834,009 | A | 11/1998 | Sawers et al. | |
| 5,879,292 | A | 3/1999 | Sternberg et al. | |
| 5,942,186 | A | 8/1999 | Sanada et al. | |
| 6,015,399 | A * | 1/2000 | Mracna | A61F 5/445 604/332 |
| 6,025,725 | A | 2/2000 | Gershenfeld et al. | |
| 6,057,689 | A | 5/2000 | Saadat | |
| 6,103,033 | A | 8/2000 | Say et al. | |
| 6,135,986 | A * | 10/2000 | Leisner | A61F 5/441 604/324 |
| 6,165,005 | A | 12/2000 | Mills et al. | |
| 6,171,289 | B1 * | 1/2001 | Millot | A61F 5/443 604/336 |
| 6,206,864 | B1 | 3/2001 | Kavanagh et al. | |
| 6,407,308 | B1 | 6/2002 | Roe et al. | |
| 6,433,244 | B1 | 8/2002 | Roe et al. | |
| 6,482,491 | B1 | 11/2002 | Samuelsen et al. | |
| 6,485,476 | B1 | 11/2002 | von Dyck et al. | |
| 6,520,943 | B1 | 2/2003 | Wagner | |
| 6,659,989 | B1 | 12/2003 | Otto | |
| 6,764,474 | B2 | 7/2004 | Nielsen et al. | |
| 7,066,919 | B1 * | 6/2006 | Sauerland | A61F 5/445 604/327 |
| 7,150,728 | B2 | 12/2006 | Hansen et al. | |
| 7,166,091 | B1 * | 1/2007 | Zeltner | A61F 5/445 604/338 |
| 7,199,501 | B2 | 4/2007 | Pei et al. | |
| 7,214,217 | B2 | 5/2007 | Pedersen et al. | |
| 7,326,190 | B2 * | 2/2008 | Botten | A61F 5/441 604/332 |
| 7,341,578 | B2 * | 3/2008 | Bulow | A61F 5/441 604/338 |
| 7,347,844 | B2 | 3/2008 | Cline et al. | |
| 7,367,965 | B2 * | 5/2008 | Poulsen | A61F 5/441 604/324 |
| 7,559,922 | B2 * | 7/2009 | Botten | A61F 5/441 604/332 |
| 7,625,362 | B2 * | 12/2009 | Boehringer | A61M 1/74 604/304 |
| 7,641,612 | B1 | 1/2010 | McCall | |
| 7,670,289 | B1 * | 3/2010 | McCall | A61M 1/3653 210/651 |
| 7,943,812 | B2 | 5/2011 | Stroebeck et al. | |
| 7,981,098 | B2 * | 7/2011 | Boehringer | A61M 1/74 604/319 |
| 3,061,360 | A1 | 11/2011 | Locke et al. | |
| 8,277,427 | B2 | 10/2012 | Edvardsen et al. | |
| 8,319,003 | B2 | 11/2012 | Olsen et al. | |
| 8,398,575 | B1 | 3/2013 | McCall | |
| 8,398,603 | B2 * | 3/2013 | Thirstrup | A61B 5/746 602/41 |
| 8,399,732 | B2 | 3/2013 | Oelund et al. | |
| 8,409,158 | B2 * | 4/2013 | Edvardsen | A61F 5/443 604/335 |
| 8,449,471 | B2 | 5/2013 | Tran | |
| 8,500,718 | B2 | 8/2013 | Locke et al. | |
| 8,632,492 | B2 * | 1/2014 | DeLegge | A61M 39/0247 604/99.04 |
| 8,680,991 | B2 | 3/2014 | Tran | |
| 8,684,982 | B2 * | 4/2014 | Nguyen-DeMary | A61F 5/441 604/327 |
| 8,740,865 | B2 | 6/2014 | Krystek et al. | |
| 8,795,257 | B2 | 8/2014 | Coulthard et al. | |
| 8,821,464 | B2 * | 9/2014 | Hanuka | A61F 5/441 604/333 |
| 8,975,465 | B2 | 3/2015 | Hong et al. | |
| 9,046,085 | B2 | 6/2015 | Schoess et al. | |
| 9,066,812 | B2 * | 6/2015 | Edvardsen | A61F 5/443 |
| 9,216,104 | B2 * | 12/2015 | Thirstrup | A61F 5/4404 |
| 9,308,332 | B2 | 4/2016 | Heppe | |
| 9,322,797 | B1 | 4/2016 | Lastinger et al. | |
| 9,629,964 | B2 | 4/2017 | Wuepper | |
| 9,693,908 | B2 * | 7/2017 | Eriksson | A61M 1/82 |
| 9,770,359 | B2 | 9/2017 | Edvardsen et al. | |
| 9,788,991 | B2 | 10/2017 | Bird | |
| 9,867,934 | B2 | 1/2018 | Heppe | |
| 9,928,341 | B2 * | 3/2018 | Angelides | G16H 40/67 |
| 10,016,298 | B2 * | 7/2018 | Thirstrup | A61F 13/42 |
| D826,740 | S | 8/2018 | Stevens et al. | |
| 10,500,084 | B2 * | 12/2019 | Hansen | A61F 5/4404 |
| 10,531,977 | B2 * | 1/2020 | Schoess | A61F 5/445 |
| 10,646,370 | B2 * | 5/2020 | Keleny | A61F 5/441 |
| 10,792,184 | B2 * | 10/2020 | Hvid | A61M 3/0208 |
| 10,799,385 | B2 * | 10/2020 | Hansen | A61F 5/445 |
| 10,849,781 | B2 * | 12/2020 | Hansen | A61F 5/445 |
| 10,874,541 | B2 | 12/2020 | Seres et al. | |
| 10,987,243 | B2 * | 4/2021 | Thirstrup | A61B 5/746 |
| 11,096,818 | B2 * | 8/2021 | Thirstrup | A61F 13/02 |
| 11,135,084 | B2 | 10/2021 | Seres et al. | |
| 11,406,525 | B2 * | 8/2022 | Seres | A61B 5/14539 |
| 11,471,318 | B2 | 10/2022 | Hansen et al. | |
| 11,491,042 | B2 * | 11/2022 | Seres | A61B 5/002 |
| 11,534,323 | B2 * | 12/2022 | Hansen | G06T 7/70 |
| 11,540,937 | B2 * | 1/2023 | Hansen | A61F 5/445 |
| 11,547,595 | B2 * | 1/2023 | Hansen | A61B 5/6833 |
| 11,547,596 | B2 * | 1/2023 | Hansen | A61F 5/443 |
| 11,559,423 | B2 * | 1/2023 | Speiermann | A61F 5/44 |
| 11,559,426 | B2 * | 1/2023 | Sletten | A61F 5/44 |
| 2002/0019615 | A1 | 2/2002 | Roe et al. | |

(56) References Cited

U.S. PATENT DOCUMENTS

| | | |
|---|---|---|
| 2003/0132763 A1 | 7/2003 | Ellenz |
| 2003/0169032 A1 | 9/2003 | Minchole et al. |
| 2004/0006320 A1 | 1/2004 | Buglino et al. |
| 2004/0030305 A1 | 2/2004 | Sakamoto |
| 2004/0036484 A1 | 2/2004 | Tamai |
| 2004/0049145 A1 | 3/2004 | Flick |
| 2004/0078219 A1* | 4/2004 | Kaylor .................. G16H 40/67 600/300 |
| 2004/0100376 A1* | 5/2004 | Lye ........................ A61B 5/411 600/300 |
| 2004/0106908 A1 | 6/2004 | Leise, Jr. et al. |
| 2004/0111072 A1 | 6/2004 | McKissick |
| 2004/0133175 A1 | 7/2004 | Hagedorn-Olsen |
| 2004/0171999 A1 | 9/2004 | Andersen et al. |
| 2004/0193122 A1 | 9/2004 | Cline et al. |
| 2004/0193123 A1 | 9/2004 | Fenton |
| 2004/0216833 A1 | 11/2004 | Fleming et al. |
| 2005/0054997 A1 | 3/2005 | Buglino et al. |
| 2005/0065488 A1 | 3/2005 | Elliott |
| 2005/0070863 A1* | 3/2005 | Bulow .................... A61F 5/441 604/332 |
| 2005/0085779 A1* | 4/2005 | Poulsen ................. A61F 5/441 604/332 |
| 2005/0101841 A9* | 5/2005 | Kaylor .................. G16H 40/67 600/300 |
| 2005/0240163 A1 | 10/2005 | Andersen |
| 2005/0261645 A1* | 11/2005 | Conrad ................... A61F 5/445 604/332 |
| 2006/0015081 A1 | 1/2006 | Suzuki et al. |
| 2006/0025727 A1* | 2/2006 | Boehringer ........... A61M 1/966 604/313 |
| 2006/0052752 A1* | 3/2006 | McMichael ......... A61J 15/0034 604/910 |
| 2006/0194324 A1 | 8/2006 | Faries, Jr. et al. |
| 2006/0271002 A1* | 11/2006 | Botten .................... A61F 5/441 604/339 |
| 2007/0035405 A1 | 2/2007 | Wada et al. |
| 2007/0135782 A1 | 6/2007 | Bager et al. |
| 2007/0185464 A1 | 8/2007 | Fattman et al. |
| 2008/0038536 A1 | 2/2008 | Strobech et al. |
| 2008/0071214 A1 | 3/2008 | Locke et al. |
| 2008/0075934 A1 | 3/2008 | Barlow, Jr. et al. |
| 2008/0091154 A1* | 4/2008 | Botten .................... A61F 5/441 96/155 |
| 2008/0097360 A1 | 4/2008 | Andersen et al. |
| 2008/0140057 A1 | 6/2008 | Wood et al. |
| 2008/0234641 A1 | 9/2008 | Locke et al. |
| 2008/0275327 A1* | 11/2008 | Faarbaek ............ A61B 5/68335 600/382 |
| 2008/0278337 A1 | 11/2008 | Huang et al. |
| 2008/0300559 A1 | 12/2008 | Gustafson et al. |
| 2008/0306459 A1 | 12/2008 | Albrectsen |
| 2009/0012501 A1* | 1/2009 | Boehringer ........... A61M 1/966 604/543 |
| 2009/0118600 A1 | 5/2009 | Ortiz et al. |
| 2009/0118687 A1* | 5/2009 | Kristensen ............ A61F 5/448 604/342 |
| 2009/0167286 A1 | 7/2009 | Naylor et al. |
| 2009/0173935 A1 | 7/2009 | Cho et al. |
| 2009/0227969 A1 | 9/2009 | Jaeb et al. |
| 2009/0247970 A1* | 10/2009 | Keleny ............... B01D 46/0036 156/247 |
| 2010/0010460 A1* | 1/2010 | Butler .................... A61F 5/441 604/333 |
| 2010/0030167 A1* | 2/2010 | Thirstrup ............ A61F 5/4404 340/657 |
| 2010/0036206 A1 | 2/2010 | Lorio |
| 2010/0072271 A1 | 3/2010 | Thorstensson |
| 2011/0034890 A1 | 2/2011 | Stroebech et al. |
| 2011/0077497 A1 | 3/2011 | Oster et al. |
| 2011/0130642 A1 | 6/2011 | Jaeb et al. |
| 2012/0013130 A1 | 1/2012 | Jung |
| 2012/0143154 A1* | 6/2012 | Edvardsen ........... A61F 5/4404 604/336 |
| 2012/0143155 A1* | 6/2012 | Edvardsen ............. A61F 5/443 604/318 |
| 2012/0253224 A1 | 10/2012 | Mir et al. |
| 2012/0258302 A1 | 10/2012 | Hunt et al. |
| 2012/0259230 A1 | 10/2012 | Riley |
| 2012/0283678 A1* | 11/2012 | Nguyen-DeMary .... A61F 5/445 604/338 |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1* | 3/2013 | Hanuka ................. A61F 5/441 604/344 |
| 2013/0066285 A1 | 3/2013 | Locke et al. |
| 2013/0072886 A1* | 3/2013 | Schertiger ............. A61F 5/445 604/335 |
| 2013/0102979 A1 | 4/2013 | Coulthard et al. |
| 2013/0138065 A1 | 5/2013 | Buus |
| 2013/0150769 A1 | 6/2013 | Heppe |
| 2013/0165862 A1* | 6/2013 | Griffith .............. A61J 15/0026 604/174 |
| 2013/0192604 A1* | 8/2013 | Persson ............... A61M 16/047 128/207.16 |
| 2013/0226116 A1 | 8/2013 | Edvardsen et al. |
| 2013/0231620 A1* | 9/2013 | Thirstrup ............... A61F 5/445 604/344 |
| 2013/0261575 A1 | 10/2013 | Kiyoshi |
| 2013/0303867 A1 | 11/2013 | Elfstrom et al. |
| 2013/0324952 A1 | 12/2013 | Krystek et al. |
| 2013/0324955 A1 | 12/2013 | Wong et al. |
| 2014/0051946 A1 | 2/2014 | Arne et al. |
| 2014/0200538 A1 | 7/2014 | Euliano et al. |
| 2014/0236111 A1 | 8/2014 | Casado et al. |
| 2014/0236335 A1 | 8/2014 | Lewis et al. |
| 2014/0275854 A1 | 9/2014 | Venkatraman et al. |
| 2014/0276501 A1* | 9/2014 | Cisko ..................... A61F 5/443 604/355 |
| 2014/0288381 A1* | 9/2014 | Faarbaek ............. A61B 5/0002 600/300 |
| 2014/0323909 A1 | 10/2014 | Kim |
| 2014/0327433 A1 | 11/2014 | Anway et al. |
| 2014/0336493 A1 | 11/2014 | Kulach et al. |
| 2015/0231802 A1 | 8/2015 | Quan et al. |
| 2015/0250639 A1* | 9/2015 | Thirstrup .......... A61F 13/00051 156/278 |
| 2015/0257923 A1 | 9/2015 | Thirstrup et al. |
| 2015/0342777 A1 | 12/2015 | Seres et al. |
| 2015/0374896 A1 | 12/2015 | Du et al. |
| 2016/0084869 A1 | 3/2016 | Yuen et al. |
| 2016/0158056 A1 | 6/2016 | Davis et al. |
| 2016/0158969 A1 | 6/2016 | McLane et al. |
| 2016/0166438 A1* | 6/2016 | Rovaniemi ............ A61F 13/42 493/320 |
| 2016/0218555 A1 | 7/2016 | Slaby et al. |
| 2016/0235581 A1* | 8/2016 | Keleny ................... A61F 5/441 |
| 2016/0278990 A1 | 9/2016 | Chen |
| 2016/0284084 A1 | 9/2016 | Gurcan et al. |
| 2016/0305776 A1 | 10/2016 | Martensson et al. |
| 2016/0310140 A1 | 10/2016 | Belson et al. |
| 2016/0310329 A1 | 10/2016 | Patel et al. |
| 2016/0317728 A1 | 11/2016 | Lewis et al. |
| 2016/0361015 A1 | 12/2016 | Wang et al. |
| 2017/0042614 A1 | 2/2017 | Salahieh et al. |
| 2017/0050004 A1* | 2/2017 | Tilson ................ A61B 17/8816 |
| 2017/0055896 A1 | 3/2017 | Al-Ali et al. |
| 2017/0079576 A1 | 3/2017 | Stroebech et al. |
| 2017/0112658 A1* | 4/2017 | Hosono .................. A61F 5/445 |
| 2017/0140103 A1* | 5/2017 | Angelides ............ A61F 5/4404 |
| 2017/0156920 A1 | 6/2017 | Hunt et al. |
| 2017/0262986 A1 | 9/2017 | Xiong et al. |
| 2017/0340474 A1* | 11/2017 | Thirstrup ............... A61B 5/746 |
| 2017/0348137 A1* | 12/2017 | Hvid ................... A61M 3/0202 |
| 2017/0360592 A1* | 12/2017 | Carrubba ................ A61F 5/445 |
| 2018/0049667 A1 | 2/2018 | Heppe |
| 2018/0055359 A1 | 3/2018 | Shamim et al. |
| 2018/0078163 A1 | 3/2018 | Welch |
| 2018/0171183 A1 | 6/2018 | Sakurai et al. |

(56) References Cited

U.S. PATENT DOCUMENTS

| | | | |
|---|---|---|---|
| 2019/0099552 A1 | 4/2019 | Zhang et al. | |
| 2019/0133810 A1* | 5/2019 | Seres | A61F 5/4404 |
| 2019/0133811 A1* | 5/2019 | Seres | A61F 5/4404 |
| 2019/0133812 A1* | 5/2019 | Seres | A61F 5/448 |
| 2019/0142623 A1* | 5/2019 | Schoess | A61F 5/4404 |
| | | | 604/336 |
| 2019/0175386 A1* | 6/2019 | Monty | A61F 5/445 |
| 2019/0192066 A1 | 6/2019 | Schoess et al. | |
| 2019/0192332 A1* | 6/2019 | Hansen | A61B 5/7405 |
| 2019/0192333 A1* | 6/2019 | Hansen | A61F 5/445 |
| 2019/0192334 A1* | 6/2019 | Hansen | G01M 3/40 |
| 2019/0240059 A1 | 8/2019 | Seres et al. | |
| 2019/0247050 A1* | 8/2019 | Goldsmith | A61F 2/82 |
| 2019/0374163 A1* | 12/2019 | Faarbaek | A61B 5/6833 |
| 2019/0374372 A1* | 12/2019 | Seres | A61B 5/6802 |
| 2020/0100931 A1 | 4/2020 | Schoess et al. | |
| 2020/0188161 A1 | 6/2020 | Seres et al. | |
| 2020/0246174 A1 | 8/2020 | Hansen et al. | |
| 2020/0246175 A1 | 8/2020 | Hansen et al. | |
| 2020/0246176 A1 | 8/2020 | Hansen et al. | |
| 2020/0246177 A1 | 8/2020 | Hansen et al. | |
| 2020/0276063 A1 | 9/2020 | Muñoz Herencia | |
| 2020/0306074 A1 | 10/2020 | Speiermann et al. | |
| 2020/0330258 A1 | 10/2020 | Hansen et al. | |
| 2020/0330260 A1 | 10/2020 | Hansen et al. | |
| 2020/0337880 A1 | 10/2020 | Hansen et al. | |
| 2020/0337881 A1 | 10/2020 | Hansen et al. | |
| 2020/0337882 A1 | 10/2020 | Hansen et al. | |
| 2020/0337883 A1 | 10/2020 | Hansen et al. | |
| 2020/0375499 A1 | 12/2020 | Hansen et al. | |
| 2020/0375782 A1 | 12/2020 | Hansen et al. | |
| 2020/0375783 A1 | 12/2020 | Hansen et al. | |
| 2020/0375784 A1 | 12/2020 | Hansen et al. | |
| 2020/0375785 A1 | 12/2020 | Hansen et al. | |
| 2020/0375786 A1 | 12/2020 | Hansen et al. | |
| 2020/0383637 A1 | 12/2020 | Hansen et al. | |
| 2020/0383818 A1 | 12/2020 | Hansen et al. | |
| 2020/0383819 A1 | 12/2020 | Sletten et al. | |
| 2020/0383820 A1 | 12/2020 | Hansen et al. | |
| 2020/0383821 A1 | 12/2020 | Hansen et al. | |
| 2020/0390587 A1 | 12/2020 | Svanegaard et al. | |
| 2020/0390588 A1 | 12/2020 | Svanegaard et al. | |
| 2020/0390589 A1 | 12/2020 | Hansen et al. | |
| 2020/0395120 A1 | 12/2020 | Svanegaard et al. | |
| 2020/0395610 A1 | 12/2020 | Ono et al. | |
| 2020/0405228 A1 | 12/2020 | Svanegaard et al. | |
| 2020/0405229 A1 | 12/2020 | Svanegaard et al. | |
| 2020/0405230 A1 | 12/2020 | Svanegaard et al. | |
| 2021/0000414 A1 | 1/2021 | Svanegaard et al. | |
| 2021/0000633 A1 | 1/2021 | Hansen et al. | |
| 2021/0000634 A1 | 1/2021 | Svanegaard et al. | |
| 2021/0000635 A1 | 1/2021 | Hansen et al. | |
| 2021/0000636 A1 | 1/2021 | Hansen et al. | |
| 2021/0007663 A1 | 1/2021 | Svanegaard et al. | |
| 2021/0007881 A1 | 1/2021 | Svanegaard et al. | |
| 2021/0015653 A1 | 1/2021 | Hansen et al. | |
| 2021/0015654 A1 | 1/2021 | Hansen et al. | |
| 2021/0022683 A1 | 1/2021 | Faarbaek et al. | |
| 2021/0038424 A1 | 2/2021 | Svanegaard et al. | |
| 2021/0059603 A1 | 3/2021 | Svanegaard et al. | |
| 2021/0085511 A1 | 3/2021 | Hansen et al. | |
| 2021/0085512 A1 | 3/2021 | Hansen et al. | |
| 2021/0128364 A1 | 5/2021 | Cole et al. | |
| 2021/0177642 A1 | 6/2021 | Andersen et al. | |
| 2021/0212855 A1 | 7/2021 | Hansen et al. | |
| 2021/0338471 A1 | 11/2021 | Nolan et al. | |
| 2021/0361464 A1 | 11/2021 | Larsen et al. | |
| 2021/0361465 A1 | 11/2021 | Hansen et al. | |
| 2021/0361466 A1 | 11/2021 | Hansen et al. | |
| 2021/0361467 A1 | 11/2021 | Hansen et al. | |
| 2021/0369197 A1 | 12/2021 | Hansen et al. | |
| 2021/0369488 A1 | 12/2021 | Hansen et al. | |
| 2021/0369489 A1 | 12/2021 | Hansen et al. | |
| 2021/0369490 A1 | 12/2021 | Hansen et al. | |
| 2021/0386368 A1 | 12/2021 | Carlsson et al. | |
| 2022/0000652 A1 | 1/2022 | Thirstrup et al. | |
| 2022/0031495 A1 | 2/2022 | Seres et al. | |
| 2022/0079802 A1 | 3/2022 | Hansen | |
| 2022/0079803 A1 | 3/2022 | Windeballe et al. | |
| 2022/0087851 A1 | 3/2022 | Stroebech | |
| 2022/0117771 A1 | 4/2022 | Feam et al. | |
| 2022/0142807 A1 | 5/2022 | Tofte | |
| 2022/0192860 A1 | 6/2022 | Hansen et al. | |
| 2022/0241104 A1 | 8/2022 | Knoedler | |
| 2022/0241105 A1 | 8/2022 | Hansen et al. | |
| 2022/0265458 A1 | 8/2022 | Carlsson et al. | |
| 2022/0378602 A1* | 12/2022 | Hansen | A61F 5/448 |

FOREIGN PATENT DOCUMENTS

| | | | |
|---|---|---|---|
| CN | 104980878 A | 10/2015 | |
| CN | 105588856 A | 5/2016 | |
| CN | 206271160 U | 6/2017 | |
| CN | 206450708 U | 8/2017 | |
| DE | 3437950 A1 | 4/1985 | |
| DE | 3836590 A1 | 5/1990 | |
| DE | 19953062 A1 | 5/2000 | |
| DE | 19900611 C1 | 7/2000 | |
| DE | 102011014321 A1 | 9/2012 | |
| DE | 102011076219 A1 | 11/2012 | |
| EP | 0168967 A1 | 1/1986 | |
| EP | 0373782 B1 | 10/1994 | |
| EP | 0416397 B1 | 5/1995 | |
| EP | 0800804 B1 | 6/2003 | |
| EP | 1188157 B1 | 12/2005 | |
| EP | 2108345 A1 | 10/2009 | |
| EP | 1275357 B1 | 3/2011 | |
| EP | 2601915 A1 | 6/2013 | |
| EP | 2257253 B1 | 1/2014 | |
| EP | 2489561 B1 | 8/2014 | |
| EP | 2451349 B1 | 4/2016 | |
| EP | 2654646 B1 | 7/2016 | |
| EP | 3064179 A1 | 9/2016 | |
| EP | 3213727 A1 | 9/2017 | |
| GB | 2219679 A | 12/1989 | |
| GB | 2343628 B | 10/2000 | |
| GB | 2465742 B | 7/2012 | |
| GB | 2542093 A | 3/2017 | |
| JP | H4074882 A | 3/1992 | |
| JP | H06152077 A | 5/1994 | |
| JP | H0910184 A | 1/1997 | |
| JP | 2000093448 A | 4/2000 | |
| JP | 2001087299 A | 4/2001 | |
| JP | 2002055074 A | 2/2002 | |
| JP | 2002224093 A | 8/2002 | |
| JP | 2005323981 A | 11/2005 | |
| JP | 2007319561 A | 12/2007 | |
| JP | 2014033745 A | 2/2014 | |
| JP | 2014054368 A | 3/2014 | |
| JP | 2014507182 A | 3/2014 | |
| KR | 2012003987 A | 1/2012 | |
| RU | 2527155 C2 | 8/2014 | |
| TW | 201201783 A | 1/2012 | |
| WO | 1994015562 A1 | 7/1994 | |
| WO | 1997010012 A1 | 3/1997 | |
| WO | 1999033037 A1 | 7/1999 | |
| WO | 1999036017 A1 | 7/1999 | |
| WO | 2000079497 A1 | 12/2000 | |
| WO | 2001013830 A1 | 3/2001 | |
| WO | 2001050996 A1 | 7/2001 | |
| WO | 2002052302 A2 | 7/2002 | |
| WO | 2002099765 A1 | 12/2002 | |
| WO | 2005082271 A2 | 9/2005 | |
| WO | 2006008866 A1 | 1/2006 | |
| WO | 2006094513 A2 | 9/2006 | |
| WO | 2007000168 A1 | 1/2007 | |
| WO | 2007059774 A2 | 5/2007 | |
| WO | 2007098762 A1 | 9/2007 | |
| WO | WO-2007098762 A1 * | 9/2007 | A61B 5/746 |
| WO | 2007133555 A2 | 11/2007 | |
| WO | 2008057884 A2 | 5/2008 | |
| WO | 2009006900 A1 | 1/2009 | |
| WO | 2009052496 A1 | 4/2009 | |
| WO | 2009112912 A2 | 9/2009 | |

(56) References Cited

FOREIGN PATENT DOCUMENTS

| | | |
|---|---|---|
| WO | 2011003421 A1 | 1/2011 |
| WO | 2011004165 A1 | 1/2011 |
| WO | 2011061540 A1 | 5/2011 |
| WO | 2011105701 A2 | 9/2011 |
| WO | 2011123018 A1 | 10/2011 |
| WO | 2011139499 A1 | 11/2011 |
| WO | 2011161254 A2 | 12/2011 |
| WO | 2012068386 A1 | 5/2012 |
| WO | 2012076022 A2 | 6/2012 |
| WO | 2012084987 A2 | 6/2012 |
| WO | 2013013197 A1 | 1/2013 |
| WO | 2014004207 A1 | 1/2014 |
| WO | 2014086369 A1 | 6/2014 |
| WO | 2015007284 A1 | 1/2015 |
| WO | 2015014774 A1 | 2/2015 |
| WO | 2015084462 A1 | 6/2015 |
| WO | 2015094064 A1 | 6/2015 |
| WO | 2016166731 A1 | 10/2016 |
| WO | 2017023794 A1 | 2/2017 |
| WO | 2017062042 A1 | 4/2017 |
| WO | 2017067558 A1 | 4/2017 |
| WO | 2017067560 A1 | 4/2017 |
| WO | 2017088153 A1 | 6/2017 |
| WO | 2017136696 A1 | 8/2017 |
| WO | 2017190752 A1 | 11/2017 |
| WO | 2018028756 A1 | 2/2018 |
| WO | 2019094635 A1 | 5/2019 |
| WO | 2019161863 A1 | 8/2019 |

\* cited by examiner

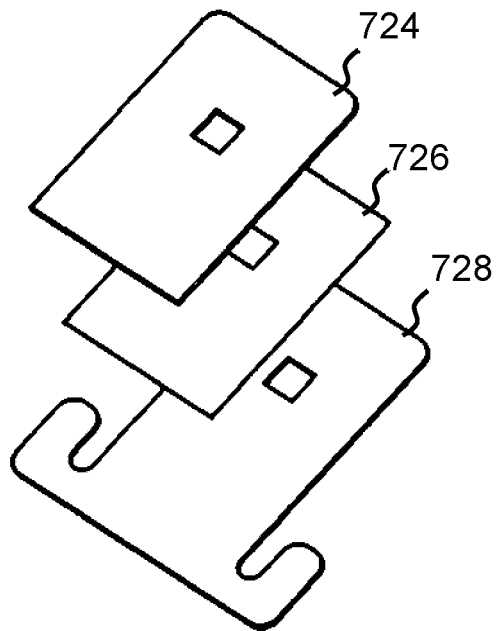
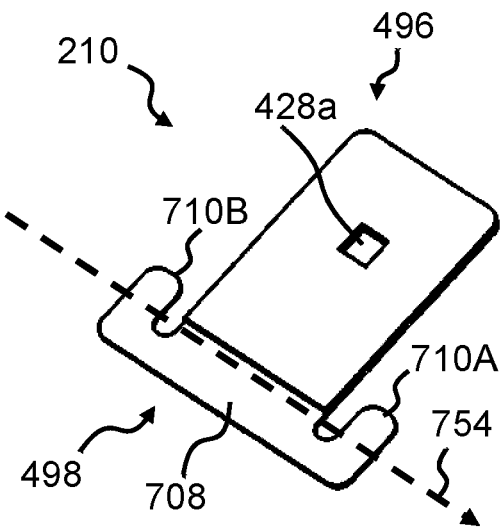
Fig. 31a
Fig. 31b
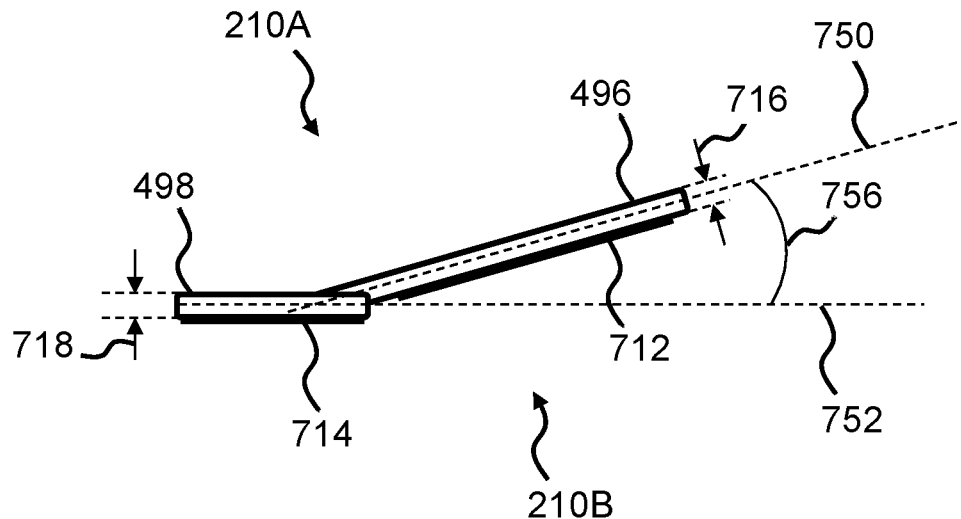
Fig. 32

COUPLING PART WITH A HINGE FOR A MEDICAL BASE PLATE AND SENSOR ASSEMBLY PART

The present disclosure relates to an ostomy system, devices thereof, method of manufacturing and method for monitoring an ostomy appliance. The ostomy appliance system comprises an ostomy appliance and an ostomy monitor device. In particular, the present disclosure relates to leakage classification and/or detection and monitoring of the operation of an ostomy appliance.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
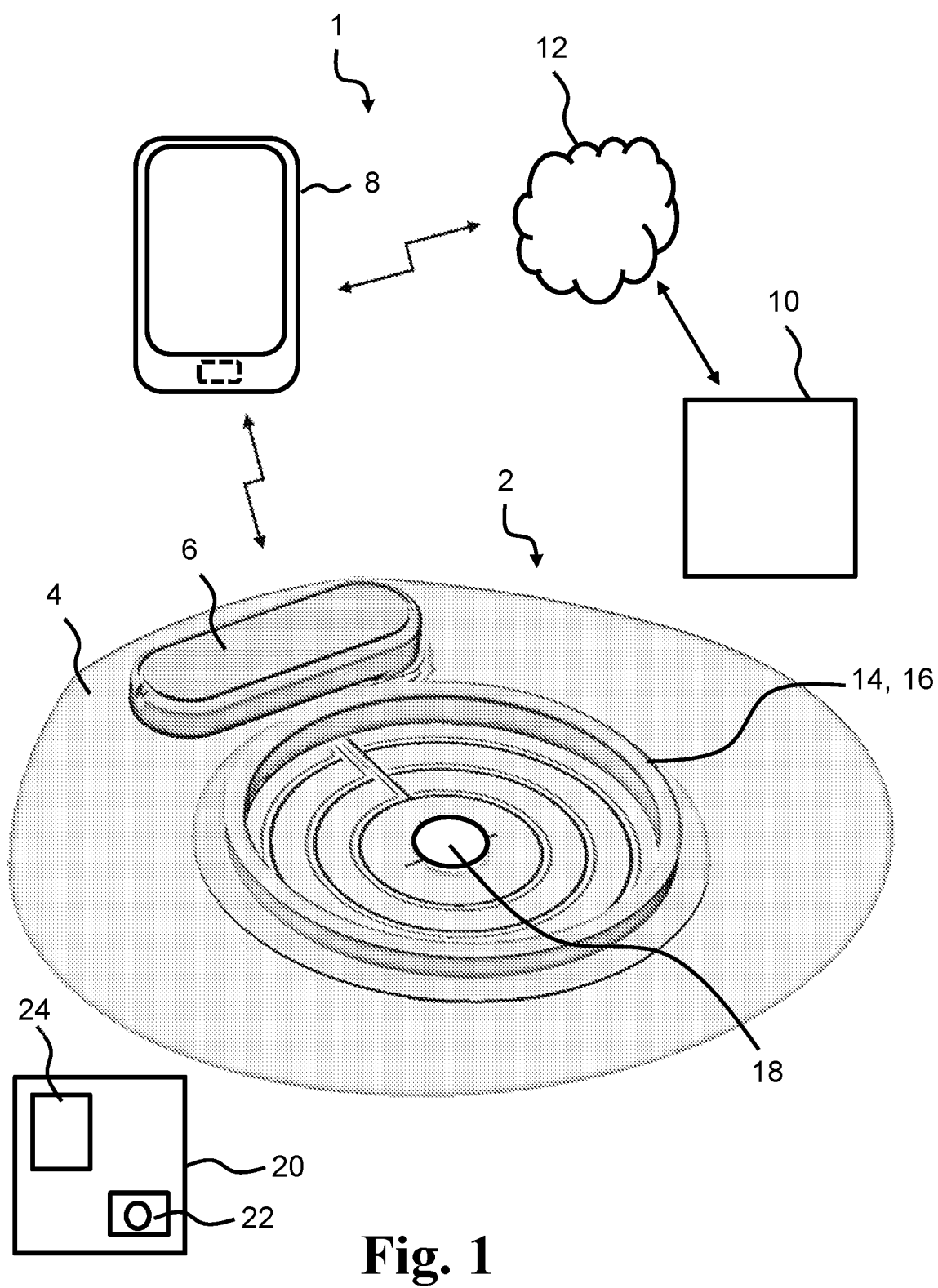
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, severity and rapidness of moisture propagation in the adhesive material provided for attaching the base plate to the skin surface of a user. Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The ostomy appliance includes a base plate, such as a monolithic, one-piece base plate, e.g. integrated with a sensor assembly part, or a base plate and a separate sensor assembly part, such as a sensor assembly part to be subsequently applied to a base plate. For example, to allow an arbitrary base plate, such as a conventional base plate, to achieve the features as described herein. Features as described with respect to the base plate herein may be provided by a sensor assembly part to be applied to a base plate, e.g. by the user. A sensor assembly part may be adapted to adhere to an ostomy plate.

A disclosed method of attaching a base plate to a user's stoma and/or skin surrounding the stoma, such as the peristomal skin area, may comprise attaching a sensor assembly part to a base plate and attaching the base plate, e.g. together with the attached sensor assembly part, to the user's stoma and/or skin surrounding the stoma, such as the peristomal skin area. Alternatively, the method of attaching the base plate to the user's stoma and/or skin surrounding the stoma may comprise attaching the sensor assembly part to the user's stoma and/or skin surrounding the stoma and attaching the base plate to the user's stoma and/or skin surrounding the stoma above the attached sensor assembly part.

The base plate and/or the sensor assembly part may comprise a first adhesive layer, also denoted center adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate and/or the sensor assembly part to the skin surface of a user. The first adhesive layer may have a stomal opening, such as a first adhesive stomal opening, with a center point.

The first adhesive layer may be made of a first composition. The first composition may comprise one or more polyisobutenes and/or styrene-isoprene-styrene. The first composition may comprise one or more hydrocolloids. The first composition may comprise one or more water soluble or water swellable hydrocolloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids and synthetic hydrocolloids. The first composition may comprise 20-60% hydrocolloids. A preferred hydrocolloid is carboxymethylcellulose (CMC). The first composition may optionally contain other components, such as fillers, tackifiers, plasticizers, and other additives.

The first adhesive layer may have a plurality of sensor point openings. A sensor point opening of the first adhesive layer is optionally configured to overlap a part of an electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap parts of an electrode and the primary second sensor point openings configured to overlap parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap parts of an electrode and the secondary second sensor point openings configured to overlap parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap parts of an electrode and the tertiary second sensor point openings configured to overlap parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm.

The secondary radial distance may be in the range from 20 mm to 50 mm, such as in the range from 25 mm to 35 mm, e.g. 30 mm.

The base plate and/or the sensor assembly part may comprise a second layer. The second layer may be a second adhesive layer, also denoted rim adhesive layer. The second layer may have a second radial extension that is larger than a first radial extension of the first adhesive layer at least in a first angular range of the base plate and/or the sensor assembly part. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening, such as a second layer stomal opening and/or a second adhesive stomal opening, with a center point.

The second adhesive layer may be made of a second composition. The second composition may comprise one or more polyisobutenes and/or styrene-isoprene-styrene. The second composition may comprise one or more hydrocolloids. The second composition may comprise one or more water soluble or water swellable hydrocolloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids and synthetic hydrocolloids. The second composition may comprise 20-60% hydrocolloids. A preferred hydrocolloid is carboxymethylcellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively or additionally, the second adhesive layer may be thinner than the first adhesive layer. Alternatively or additionally, the second adhesive layer may be less water and/or sweat absorbing than the first adhesive layer. Alternatively or additionally, the second adhesive layer may be less mouldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate and/or the sensor assembly part may comprise one or more electrodes, such as a plurality of electrodes, such as two, three, four, five, six, seven or more electrodes. The sensor assembly part may be applied to the base plate, such as to provide the base plate with the one or more electrodes.

The electrodes, e.g. some or all the electrodes, may be arranged between the first adhesive layer and the second adhesive layer. The electrodes may be arranged in an electrode assembly, e.g. an electrode layer. An electrode comprises a connection part for connecting the electrodes to other components and/or interface terminals. An electrode may comprise one or more conductor parts and/or one or more sensing parts. The electrode assembly may be arranged between the first adhesive layer and the second adhesive layer. The base plate and/or the sensor assembly part, e.g. the electrode assembly, may comprise a first electrode, a second electrode and optionally a third electrode. The base plate and/or the sensor assembly part, e.g. the electrode assembly, may comprise a fourth electrode and/or a fifth electrode. The base plate and/or the sensor assembly part, e.g. the electrode assembly, optionally comprises a sixth electrode. The base plate and/or the sensor assembly part, e.g. the electrode assembly, may comprise a ground electrode. The ground electrode may comprise a first electrode part. The first electrode part of the ground electrode may form a ground for the first electrode. The ground electrode may comprise a second electrode part. The second electrode part of the ground electrode may form a ground for the second electrode. The ground electrode may comprise a third electrode part. The third electrode part of the ground electrode may form a ground for the third electrode. The ground electrode may comprise a fourth electrode part. The fourth electrode part of the ground electrode may form a ground for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair.

The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The electrode assembly may comprise a support layer, also denoted a support film. One or more electrodes may be formed, e.g. printed, on the proximal side of the support layer. One or more electrodes may be formed, e.g. printed, on the distal side of the support layer. The electrode assembly, such as the support layer of the electrode assembly, may have a stomal opening, such as an electrode assembly stomal opening and/or a support layer stomal opening, with a center point.

The support layer may comprise polymeric (e.g. polyurethane, PTFE, PVDF) and/or ceramic (e.g. alumina, silica) materials. In one or more exemplary base plates and/or sensor assembly parts, the support layer is made of thermoplastic polyurethane (TPU). The support layer material may be made of or comprise one or more of polyester, a thermoplastic elastomer (TPE), polyimide, polyimide, Ethylene-vinyl acetate (EVA), polyurea, and silicones.

Exemplary thermoplastic elastomers of the support layer are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part, such as the electrode assembly may comprise a masking element configured to insulate at least parts of the electrodes from the first adhesive layer of the base plate and/or the sensor assembly part. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s) A sensor point opening of the masking element overlaps at least one electrode of the electrode assembly when seen in the axial direction, e.g. to form a sensor point. For example, a primary sensor point opening may overlap a part of the ground electrode and/or a part of the fourth electrode. A secondary sensor point opening may overlap a part of the fourth electrode and/or a part of the fifth electrode. A tertiary sensor point opening may overlap a part of the fifth electrode and/or a part of the ground electrode.

The masking element may comprise one or more, such as a plurality of, terminal openings. The masking element may comprise polymeric (e.g. polyurethane, PTFE, PVDF) and/or ceramic (e.g. alumina, silica) materials. In one or more exemplary base plates and/or sensor assembly parts, the masking element is made of or comprises thermoplastic polyurethane (TPU). In one or more exemplary base plates and/or sensor assembly parts, the masking element is made of or comprises polyester. The masking element material may be made of or comprise one or more of polyester, a thermoplastic elastomer (TPE), polyimide, polyimide, Ethylene-vinyl acetate (EVA), polyurea, and silicones.

Exemplary thermoplastic elastomers of the masking element are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part may comprise a first intermediate element. The first intermediate element may be arranged between the electrodes/electrode layer and the first adhesive layer and/or between the second layer and the first adhesive layer. The first intermediate layer may be made of an insulating material.

The base plate and/or the sensor assembly part may comprise a release liner. The release liner is a protective layer that protects adhesive layer(s) during transport and storage and is peeled off by the user prior to applying the base plate and/or the sensor assembly part on the skin. The release liner may have a stomal opening, such as a release liner stomal opening, with a center point.

The base plate and/or the sensor assembly part may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening, such as a top layer stomal opening, with a center point. The top layer may have a thickness in the range from 0.01 mm to 1.0 mm, e.g. in the range from 0.02 mm to 0.2 mm, such as 0.04 mm.

The base plate and/or the sensor assembly part comprises a monitor interface. The monitor interface may be configured for electrically and/or mechanically connecting the ostomy appliance (base plate/sensor assembly part) to the monitor device. The monitor interface may be configured for wirelessly connecting the ostomy appliance (base plate/sensor assembly part) to the monitor device. Thus, the monitor interface of the base plate and/or the sensor assembly part is configured to electrically and/or mechanically couple the ostomy appliance and the monitor device.

The monitor interface of the base plate and/or the sensor assembly part may comprise, e.g. as part of a first connector of the monitor interface, a coupling part for forming a mechanical connection, such as a releasable coupling between the monitor device and the base plate and/or the sensor assembly part. The coupling part may be configured to engage with a coupling part of the monitor device for releasably coupling the monitor device to the base plate and/or the sensor assembly part.

The monitor interface of the base plate and/or the sensor assembly part may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes of the base plate and/or the sensor assembly part, such as the electrode assembly. The first intermediate element may be arranged between the terminal elements and the first adhesive layer. The first intermediate element may cover or overlap terminal element(s) of the base plate and/or the sensor assembly part when seen in the axial direction. Thus, the first adhesive layer may be protected or experience more evenly distributed mechanical stress from the terminal elements of the base plate and/or the sensor assembly part, in turn reducing the risk of terminal elements penetrating or otherwise damaging the first adhesive layer. The first intermediate element may protect or mechanically and/or electrically shield the first adhesive layer from the terminal elements of the base plate and/or the sensor assembly part.

A terminal element, such as the ground terminal element, the first terminal element, the second terminal element, the third terminal element, the fourth terminal element, the fifth terminal element and/or the sixth terminal element, may comprise a distal end and a proximal end. A terminal element, such as the ground terminal element, the first terminal element, the second terminal element, the third terminal element, the fourth terminal element, the fifth terminal element and/or the sixth terminal element, may comprise a distal part, a centre part, and/or a proximal part. The distal part may be between the distal end and the centre part. The proximal part may be between the proximal end and the centre part. A terminal element, such as the ground terminal element, the first terminal element, the second terminal element, the third terminal element, the fourth terminal element, the fifth terminal element and/or the sixth terminal element, may be gold plated copper.

The base plate may comprise a coupling ring or other coupling member for coupling an ostomy pouch to the base plate (two-part ostomy appliance). The center point may be defined as a center of the coupling ring.

The base plate and/or the sensor assembly part may have a stomal opening, e.g. with a center point. The stomal opening of the base plate and/or the sensor assembly part may be formed collectively of stomal opening(s) of the layers of the base plate and/or the sensor assembly part, such as of the top layer, the first adhesive layer, the second layer and/or the sensor assembly part. The stomal opening(s) of the layers of the base plate and/or the sensor assembly part, such as of the top layer, the first adhesive layer, the second layer and/or the sensor assembly part may be aligned to form the stomal opening of the base plate and/or the sensor assembly part. The stomal opening may be a through-going passage of the base plate and/or the sensor assembly part. The stomal opening may be arranged substantially in the center of the base plate and/or the sensor assembly part. The stomal opening(s) of the layers of the base plate and/or the sensor assembly part may be arranged substantially in the center of the respective layer. The stomal opening may be configured to receive a stoma of the user and/or the stomal opening may be configured to allow output from the stoma to pass through the stomal opening an into an ostomy pouch attached to the base plate. For example, the stomal opening may be configured to allow passage of output from a proximal side of the base plate and/or sensor assembly part to a distal side of the base plate and/or sensor assembly part. The size and/or shape of the stomal opening is typically adjusted by the user or nurse before application of the ostomy appliance to accommodate the user's stoma. In one or more exemplary base plates and/or sensor assembly parts, the user forms the stomal opening during preparation of the base plate and/or the sensor assembly part for application.

The monitor device comprises a processor and one or more interfaces, such as a first interface and/or a second interface. The monitor device may comprise a memory for storing ostomy data.

In one or more exemplary monitor devices, the processor is configured to apply a processing scheme, the first interface is connected to the processor and the memory, and the first interface is configured for collecting ostomy data from the base plate and/or the sensor assembly part coupled to the first interface. The ostomy data may comprise one or more, such as all, of first ostomy data from a first electrode pair of the base plate and/or the sensor assembly part, second ostomy data from a second electrode pair of the base plate and/or the sensor assembly part, and third ostomy data from a third electrode pair of the base plate and/or the sensor assembly part. A second interface is connected to the processor. To apply a processing scheme may comprise one or more of obtain first parameter data based on the first ostomy data; obtain second parameter data based on the second ostomy data; and obtain third parameter data based on the third ostomy data. To apply a processing scheme may comprise determine an operating state of the base plate of the ostomy appliance based on one or more, such as all, of the first parameter data, the second parameter data and the third parameter data. The operating state may be indicative of a degree of radial erosion of the base plate and/or the sensor assembly part, such as of the first adhesive layer, and/or an acute leakage risk for the ostomy appliance. The monitor device is configured to, in accordance with a determination that the operating state is a first operating state, transmit a first monitor signal comprising monitor data indicative of the first operating state of the base plate via the second interface; and/or in accordance with a determination that the operating state is a second operating state, transmit a second monitor signal comprising monitor data indicative of the second operating state of the base plate via the second interface.

In one or more exemplary monitor devices, the first operating state of the base plate corresponds to a situation wherein the first adhesive layer of the base plate and/or the sensor assembly part has experienced a first degree of radial erosion, e.g. the first adhesive layer is eroded to a first radial distance of the first electrode pair but not to a second radial distance of the second electrode pair.

In one or more exemplary monitor devices, the second operating state of the base plate corresponds to a situation wherein the first adhesive layer of the base plate and/or the sensor assembly part has experienced a second degree of radial erosion, e.g. the first adhesive layer is eroded to the second radial distance of the second electrode pair but not to a third radial distance of the third electrode pair.

To obtain first parameter data based on the first ostomy data may comprise determining one or more first parameters based on the first ostomy data. To obtain second parameter data based on the second ostomy data may comprise determining one or more second parameters based on the second ostomy data. To obtain third parameter data based on the third ostomy data may comprise determining one or more third parameters based on the third ostomy data. In one or more exemplary monitor devices, determination of an operating state may be based on one or more first parameters, such as first primary parameter and/or first secondary parameter of first parameter data. In one or more exemplary monitor devices, determination of an operating state may be based on one or more second parameters, such as second primary parameter and/or second secondary parameter of the second parameter data. In one or more exemplary monitor devices, determination of an operating state may be based on one or more third parameters, such as third primary parameter and/or third secondary parameter of the third parameter data. In one or more exemplary monitor devices, determination of an operating state may be based on one or more fourth parameters, such as fourth primary parameter and/or fourth secondary parameter of the fourth parameter data.

The first parameter data, the second parameter data, and the third parameter data may be indicative of resistance between the first electrode pair, the second electrode pair, and the third electrode pair, respectively.

The first parameter data, the second parameter data, and the third parameter data may be indicative of a rate of change in resistance between the first electrode pair, the second electrode pair, and the third electrode pair, respectively.

In one or more exemplary monitor devices, to determine an operating state of the base plate is based on a first criteria set based on the first parameter data and/or the second parameter data, wherein the operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary monitor devices, to determine an operating state of the base plate may be based on a first threshold set comprising one or a plurality of first threshold values. The first threshold set may comprise one or a plurality of threshold values, e.g. to be applied in the first criteria set. The first threshold set may comprise a first primary threshold value. The first threshold set may comprise a first secondary threshold value.

The first threshold set may comprise a first tertiary threshold value.

The first criteria set may be given by $(P\_1\_1 < TH\_1\_1)$, $(P\_2\_1 > TH\_1\_2)$, and $(P\_3\_1 > TH\_1\_3)$, wherein $P\_1\_1$ is a first primary parameter based on the first parameter data, $TH\_1\_1$ is a first primary threshold value, $P\_2\_1$ is a second primary parameter based on the second parameter data, $TH\_1\_2$ is a first secondary threshold value, $P\_3\_1$ is a third primary parameter based on the third parameter data, and $TH\_1\_3$ is a first tertiary threshold value, and wherein the first operating state is indicative of low degree of radial erosion on the base plate and/or the sensor assembly part. The first threshold values ($TH\_1\_1$, $TH\_1\_2$ and $TH\_1\_3$) may be the same or different, e.g. depending on the electrode configuration of the base plate and/or the sensor assembly part. The first tertiary criterion ($P\_3\_1 < TH\_1\_3$) may be omitted in the first criteria set.

The first primary parameter $P\_1\_1$ may be indicative of the resistance between the first electrode pair (first electrode and first electrode part of the ground electrode) of the base plate and/or the sensor assembly part.

The second primary parameter may be indicative of the resistance between the second electrode pair (second electrode and second electrode part of the ground electrode) of the base plate and/or the sensor assembly part.

The third primary parameter may be indicative of resistance between the third electrode pair (third electrode and third electrode part of the ground electrode) of the base plate and/or the sensor assembly part.

In one or more exemplary monitor devices, to determine an operating state of the base plate is based on a second criteria set based on the second parameter data and/or the third parameter data, wherein the operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary monitor devices, to determine an operating state of the base plate is based on a second threshold set comprising one or a plurality of second threshold values. The second threshold set may comprise one or a plurality of threshold values, e.g. to be applied in the second criteria set. The second threshold set may comprise a second primary threshold value. The second threshold set may comprise a second secondary threshold value. The second threshold set may comprise a second tertiary threshold value.

The second criteria set may be given by $(P\_1\_1 < TH\_2\_1)$, $(P\_2\_1 < TH\_2\_2)$, and $(P\_3\_1 > TH\_2\_3)$ wherein P_1_1 is a first primary parameter based on the first parameter data and indicative of the resistance between the first electrode pair, TH_2_1 is a second primary threshold value, P_2_1 is a second primary parameter based on the second parameter data and indicative of the resistance between the second electrode pair, TH_2_2 is a second secondary threshold value, P_3_1 is a third primary parameter based on the third parameter data and indicative of the resistance between the third electrode pair, TH_2_3 is a second tertiary threshold value, and wherein the second operating state is indicative of medium degree of radial erosion on the base plate and/or the sensor assembly part. The second threshold values (TH_2_1, TH_2_2 and TH_2_3) may be the same or different, e.g. depending on the electrode configuration of the base plate and/or the sensor assembly part. The second primary criterion (P_1_1<TH_2_1) and/or the second tertiary criterion (P_3_1>TH_2_3) may be omitted in the second criteria set.

In one or more exemplary monitor devices, to determine an operating state of the base plate is based on a default criteria set based on the first parameter data, wherein the operating state is determined to be the default operating state if the default criteria set is satisfied, and in accordance with a determination that the operating state is the default operating state, transmit a default monitor signal comprising monitor data indicative of the default operating state of the ostomy appliance.

The default criteria set may be given by $(P\_1\_1 > TH\_D\_1)$, $(P\_2\_1 > TH\_D\_2)$, and $(P\_3\_1 > TH\_D\_3)$ wherein P_1_1 is a first primary parameter based on the first parameter data and indicative of the resistance between the first electrode pair, TH_D_1 is a default primary threshold value, P_2_1 is a second primary parameter based on the second parameter data and indicative of the resistance between the second electrode pair, TH_D_2 is a default secondary threshold value, P_3_1 is a third primary parameter based on the third parameter data and indicative of the resistance between the third electrode pair, TH_D_3 is a default tertiary threshold value, and wherein the default operating state is indicative of very low or no degree of radial erosion on the base plate and/or the sensor assembly part. The default threshold values (TH_D_1, TH_D_2 and TH_D_3) may be the same or different, e.g. depending on the electrode configuration of the base plate and/or the sensor assembly part.

In one or more exemplary monitor devices, to determine an operating state of the base plate is based on a third criteria set based on the third parameter data, wherein the operating state is determined to be the third operating state if the third criteria set is satisfied, and in accordance with a determination that the operating state is the third operating state, transmit a third monitor signal comprising monitor data indicative of the third operating state of the ostomy appliance.

In one or more exemplary monitor devices, the third operating state of the base plate corresponds to a situation wherein the first adhesive layer of the base plate and/or the sensor assembly part has experienced a third degree of radial erosion, e.g. the first adhesive layer is eroded to the third radial distance of the third electrode pair.

The third criteria set may be given by $(P\_1\_1 < TH\_3\_1)$, $(P\_2\_1 < TH\_3\_2)$, and $(P\_3\_1 < TH\_3\_3)$ wherein P_1_1 is a first primary parameter based on the first parameter data and indicative of the resistance between the first electrode pair, TH_3_1 is a third primary threshold value, P_2_1 is a second primary parameter based on the second parameter data and indicative of the resistance between the second electrode pair, TH_3_2 is a third secondary threshold value, P_3_1 is a third primary parameter based on the third parameter data and indicative of the resistance between the third electrode pair, TH_3_3 is a third tertiary threshold value, and wherein the third operating state is indicative of high degree of radial erosion on the base plate and/or the sensor assembly part. The third threshold values (TH_3_1, TH_3_2 and TH_3_3) may be the same or different, e.g. depending on the electrode configuration of the base plate and/or the sensor assembly part. The third primary criterion (P_1_1<TH_3_1) and/or the third secondary criterion (P_2_1<TH_3_2) may be omitted in the third criteria set.

In one or more exemplary monitor devices, the ostomy data comprises fourth ostomy data from a fourth electrode pair of the base plate and/or the sensor assembly part. To apply a processing scheme may comprise to obtain fourth parameter data based on the fourth ostomy data, and determine an operating state of the base plate of the ostomy appliance based on the fourth parameter data. The monitor device may be configured to, in accordance with a determination that the operating state is a fourth operating state, transmit a fourth monitor signal comprising monitor data indicative of the fourth operating state of the ostomy appliance.

In one or more exemplary monitor devices, the fourth operating state of the base plate corresponds to a situation, wherein the fourth electrode pair detects fluid, such as output, between the distal surface of first adhesive layer and the skin of the user at a fourth radial distance, and thus there is a high risk of leakage from the ostomy appliance in the fourth operating state.

The fourth criteria set may be given by $(P\_4\_1 < TH\_4\_4)$ wherein P_4_1 is a fourth primary parameter based on the fourth parameter data and indicative of the resistance between the fourth electrode pair and TH_4_4 is a fourth quaternary threshold value, and wherein the fourth operating state is indicative of high risk of leakage from the ostomy appliance.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and/or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part (may alternatively be denoted a device coupling part or a monitor device coupling part) for forming a mechanical connection, such as a releasable coupling between the monitor device and the base plate and/or the sensor assembly part. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device may comprise a sensor unit with one or more sensor. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively.

In one or more exemplary ostomy systems, the monitor device forms an integrated part of the ostomy appliance, e.g. the monitor device may form an integrated part of a base plate and/or the sensor assembly part of the ostomy appliance.

The ostomy system may comprise a docking station forming an accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

Disclosed is a base plate for an ostomy appliance, such as a base plate as described above. Also, a sensor assembly part for an ostomy appliance is disclosed, such as a sensor assembly part for being applied to a base plate. The base plate and/or the sensor assembly part may comprise: a top layer, a first adhesive layer, an electrode assembly comprising a plurality of electrodes; and a monitor interface configured for connecting the base plate and/or the sensor assembly part to a monitor device. The base plate and/or the sensor assembly part may comprise additional layers and/or features as described above.

The monitor interface may comprise a plurality of terminals electrically connected to the plurality of electrodes and configured to connect with respective terminals of the monitor device.

The monitor interface may comprise a coupling part configured for coupling between the monitor device and the base plate and/or the sensor assembly part. The plurality of terminals may be provided on the coupling part. The coupling part may comprise a locking section, e.g. configured to lock the monitor device in a coupled position with the base plate and/or the sensor assembly part.

Also disclosed is a monitor device, such as a monitor device as described above, such as a monitor device for connecting to a base plate and/or the sensor assembly part of an ostomy appliance, such as the base plate and/or the sensor assembly part as described above. The monitor device may comprise: a monitor device housing; electronic circuitry; and an appliance interface configured for connecting the monitor device to the base plate and/or the sensor assembly part. The monitor device may comprise additional features, such as features described above.

The appliance interface may comprise a plurality of terminals for connecting with a plurality of electrodes of the base plate and/or the sensor assembly part. The appliance interface may comprise a monitor device coupling part configured for coupling between the monitor device and the base plate and/or the sensor assembly part.

The monitor device, such as the appliance interface of the monitor device, may comprise a locking mechanism, e.g. configured to engage with a locking section of the base plate and/or the sensor assembly part, e.g. to lock the monitor device in a coupled position with the base plate and/or the sensor assembly part.

The monitor device may comprise electronic circuitry, e.g. electronic circuitry for receiving, processing, storing and/or transmitting signals and/or data. The electronic circuitry may, for example, include a processor, a wireless communication unit, memory etc. The electronic circuitry may be enclosed by the monitor device housing.

Also disclosed is an ostomy system comprising a base plate and/or a sensor assembly part and a monitor device, such as the base plate and/or the sensor assembly part as disclosed above and the monitor device as disclosed above. The ostomy system may further comprise an ostomy pouch.

The base plate and/or the sensor assembly part, such as the monitor interface, such as the coupling part, may comprise a locking section. Alternatively or additionally, the monitor device, such as the monitor device coupling part may comprise a locking section. The locking section(s) may be configured to cooperate with a respective locking mechanism.

For example a locking section of the base plate and/or the sensor assembly part may be configured to cooperate with the locking mechanism of the monitor device, and/or a locking section of the monitor device may be configured to cooperate with a locking mechanism of the base plate and/or the sensor assembly part.

The locking section(s) may comprise a hole extending through a coupling part, such as the coupling part of the base plate and/or the sensor assembly part and/or the monitor device coupling part of the monitor device. Alternatively or additionally, the locking section(s) may comprise a protrusion protruding from a surface, such as a first surface, of the coupling part and/or monitor device coupling part. Alternatively or additionally, the locking section may comprise an indent in an edge of the coupling part and/or monitor device coupling part. Alternatively or additionally, the locking section may comprise a first indent in a first edge of the coupling part and/or monitor device coupling part and a second indent in a second edge of the coupling part and/or monitor device coupling part. The first edge may be opposite the second edge. Alternatively or additionally, the locking section may comprise a recess in a surface of the coupling part and/or monitor device coupling part.

The coupling part may comprise a snap fastener, such as a first snap fastener. The monitor device coupling part may comprise a snap faster, such as a second snap fastener. The first snap fastener may be configured to cooperate with the second snap fastener.

The coupling part may comprise a protruding part. The protruding part may have concave sides. The protruding part, such as the concave sides of the protruding part, may form the locking section, e.g. of the coupling part. The monitor device coupling part may comprise a cavity. The cavity may be configured to receive the protruding part, e.g. in an engagement direction, e.g. along a protruding direction of the protruding part. The protruding part may be configured to engage with the cavity, e.g. in the engagement direction. The monitor device coupling part may comprise one or more deflectable elements positioned in the cavity, such as on the sides of the cavity. The deflectable elements may form part of the locking mechanism, e.g. of the monitor device. The deflectable elements may be configured to engage with the concave sides of the protruding part, e.g. to retain the protruding part in the cavity. The deflectable elements may be elastically deformable, such as spring elements. Alternatively, the monitor device coupling part may comprise the protruding part and the coupling part may comprise the cavity and optionally the one or more deflectable elements positioned in the cavity.

The monitor device coupling part and/or the coupling part may comprise a protruding element being positioned in the cavity, such as substantially in the centre of the cavity. The protruding part of the coupling part and/or the monitor device coupling part may comprise a socket, e.g. configured to receive the protruding element positioned in the cavity. The protruding element and the socket may be shaped to engage together. The protruding element and the socket may be shaped to limit the possible orientations, e.g. to ensure correct coupling of the monitor device to the base plate and/or the sensor assembly part. For example, the protruding element and the socket may have triangular cross sections. The plurality of terminals of the monitor device and/or the base plate and/or the sensor assembly part may be provided on the protruding element, such as on an end of the protruding element. The plurality of terminals of the base plate and/or the sensor assembly part and/or the monitor device may be provided in the socket, such as in a bottom of the socket The protruding part of the coupling part may protrude in a protruding direction, e.g. an axial direction, e.g. substantially perpendicular to a base plate plane and/or a sensor assembly part plane. The top layer and/or the first adhesive layer may extend in the base plate plane and/or the sensor assembly part plane.

The monitor device may be curved, e.g. to indicate to the user the correct way of orientating the monitor device on the base plate and/or the sensor assembly part.

The coupling part may comprise a first alignment element. The monitor device, such as the monitor device coupling part, may comprise a second alignment element. The second alignment element may be configured to engage with the first alignment element. The first alignment element may form a first alignment edge configured to be received by the second alignment element forming a depression with a second alignment edge. The second alignment element may have an open end towards a rim surface of the monitor device. Thereby, the monitor device may be aligned properly, i.e. the first alignment element and the second alignment element may prevent coupling of the monitor device if not correctly orientated.

The protruding part as described above may be positioned on top of the first alignment element, such as substantially axial to the first alignment element. For example, the first alignment edge may surround the protruding part.

The coupling part may be configured to engage with the monitor device by a linear motion in an engagement direction of the monitor device relative to the base plate and/or the sensor assembly part. The monitor device coupling part may be configured to engage with the base plate and/or the sensor assembly part, such as with the coupling part of the base plate and/or the sensor assembly part, by a linear motion in the engagement direction of the monitor device relative to the base plate and/or the sensor assembly part. For example, the monitor device, such as the monitor device coupling part, and the base plate and/or the sensor assembly part, such as the coupling part of the base plate and/or the sensor assembly part, may be transferred from being decoupled to being coupled by a linear motion, such as a single linear motion, in the engagement direction of the monitor device relative to the base plate and/or the sensor assembly part.

The coupling part may be configured to disengage with the monitor device by a linear motion in a disengagement direction of the monitor device relative to the base plate and/or the sensor assembly part. The monitor device coupling part may be configured to disengage with the base plate and/or the sensor assembly part, such as with the coupling part of the base plate and/or the sensor assembly part, by a linear motion in the disengagement direction of the monitor device relative to the base plate and/or the sensor assembly part. For example, the monitor device, such as the monitor device coupling part, and the base plate and/or the sensor assembly part, such as the coupling part of the base plate and/or the sensor assembly part, may be transferred from being coupled to being decoupled by a linear motion, such as a single linear motion, in the disengagement direction of the monitor device relative to the base plate and/or the sensor assembly part. The disengagement direction may be opposite the engagement direction. Alternatively, the disengagement direction may be perpendicular to the engagement direction.

The top layer and/or the first adhesive layer may be substantially planar, e.g. prior to being applied. The top layer and/or the first adhesive layer may extend in a base plate plane and/or a sensor assembly part plane. The engagement direction and/or the disengagement direction may be substantially parallel and/or perpendicular to the base plate plane and/or the sensor assembly part plane.

The engagement direction and/or the disengagement direction may be towards a stomal opening of the base plate and/or the sensor assembly part. For example, the engagement direction and/or the disengagement direction may be from an edge of the base plate and/or the sensor assembly part, such as from an edge of the top layer and/or the first adhesive layer. The engagement direction and/or the disengagement direction may be a radial direction of the base plate and/or the sensor assembly part. Alternatively, the engagement direction and/or the disengagement direction may be substantially perpendicular to a radial direction of the base plate and/or the sensor assembly part.

The coupling part may be substantially flat. For example, the coupling part may extend substantially in a plane, such as the base plate plane and/or the sensor assembly part plane.

The coupling part may comprise a first surface and a second surface. The second surface may be opposite the first surface. The second surface may be facing the top layer, such as in a proximal direction, e.g. the second surface may be facing the skin of the user. The first surface may be facing away from the top layer, such as in a distal direction, e.g. the first surface may be facing away from the skin of the user.

The electrode assembly may be provided between the top layer and the first adhesive layer. A distal side of the electrode assembly may be facing the top layer. A proximal side of the electrode assembly may be facing the first adhesive layer.

The electrode assembly may comprise a support layer. The plurality of electrodes may be provided on a proximal side of the support layer. The plurality of electrodes may face the first adhesive layer. The plurality of electrodes may contact the first adhesive layer.

The coupling part may be formed, at least partly, by a first electrode assembly part of the electrode assembly and/or a first top layer part of the top layer.

The first electrode assembly part may extend through an opening in the top layer to form at least part of the coupling part. The first electrode assembly part and/or a first top layer part may be cut from the electrode assembly and/or the top layer, respectively, e.g. by a U-shaped cut, to allow forming at least part of the coupling part. The first electrode assembly part and/or the first top layer part may be a part near an edge of the first electrode assembly and the top layer, respectively, to allow forming at least part of the coupling part.

The plurality of terminals may be provided on the second surface of the coupling part. Alternatively or additionally, the plurality of terminals may be provided on the first side of the coupling part.

The second surface of the coupling part and the top layer may be separated, e.g. to allow at least a part of the monitor device to be positioned between the second surface of the coupling part and the top layer, such as when the monitor device is connected to the base plate and/or the sensor assembly part.

The coupling part may comprise a first coupling part section and a second coupling part section. The coupling part may be configured to receive at least a part of the monitor device between the first coupling part section and the second coupling part section. The first coupling part section and the second coupling part section may be biased towards each other. For example, the first coupling part section may be biased towards the second coupling part section and/or the second coupling part section may be biased towards the first coupling part section. The first coupling part section may be deflectable from the second coupling part section. Alternatively or additionally, the second coupling part section may be deflectable from the first coupling part section.

The coupling part may be positioned such that the monitor device is coupled to the base plate on a distal side of the top layer. The coupling part may be positioned distal to the top layer. The coupling part may be positioned such that upon coupling the monitor device to the base plate and/or the sensor assembly part the top layer is disposed between the monitor device and the skin of the user. The monitor device may be configured such that upon coupling the monitor device to the base plate and/or the sensor assembly part a top layer of the base plate and/or the sensor assembly part is disposed between the monitor device and the skin of the user.

The monitor device may be a source of skin irritation, e.g. if the skin is touching the monitor device and/or if the monitor device is moving against the skin. Thus, it may be an advantage of the present disclosure, that the monitor device may be positioned, such that the base plate and/or the sensor assembly part creates a protective layer between the skin and the monitor device. Hence, skin irritation caused by the monitor device, may be reduced or avoided.

The monitor device, such as the monitor device housing, may have a first surface and a second surface. The first surface may be opposite the second surface. The first surface and/or the second surface may be substantially flat. The monitor device may comprise a rim surface between the first surface and the second surface. The rim surface may be substantially perpendicular to the first surface and/or the second surface.

The monitor device coupling part may be provided at the rim surface, such as at a first part of the rim surface. For example, the monitor device coupling part may be provided by an opening in the rim surface, such as in the first part of the rim surface. Alternatively, the monitor device coupling part may be provided at the first surface and/or the second surface, such as an opening or a recess in the first surface and/or the second surface.

The plurality of terminals of the monitor device may be configured for electrically connecting with the plurality of electrodes of the base plate and/or the sensor assembly part, such as by electrically connecting with the plurality of terminals of the base plate and/or the sensor assembly part.

The base plate and/or the sensor assembly part, such as the monitor interface, such as the coupling part, may comprise a locking mechanism. Alternatively or additionally, the monitor device may comprise a locking mechanism. The locking mechanism(s) may be configured to lock the monitor device in a coupled position with the base plate and/or the sensor assembly part. For example, the locking mechanism(s) may provide that the monitor device is maintained in the coupled position with the base plate and/or the sensor assembly part. The locking mechanism(s) may be configured to automatically lock the monitor device in the coupled position with the base plate and/or the sensor assembly part. For example, the locking mechanism(s) may be biased, e.g. spring biased, towards locking of the locking mechanism(s). For example, the locking mechanism may comprise biasing means, e.g. a spring, that biases the locking mechanism towards a locked position. The locking mechanism(s) may be configured to unlock the monitor device from the coupled position with the base plate and/or the sensor assembly part upon user interaction. Alternatively or additionally, the locking mechanism(s) may be configured to lock the monitor device in the coupled position with the base plate and/or the sensor assembly part upon user interaction.

The monitor device may comprise an opening for receiving the coupling part of the base plate and/or the sensor assembly part. For example, the monitor device coupling part may be provided by the opening for receiving the coupling part of the base plate and/or the sensor assembly part. The locking mechanism may comprise a locking component positioned inside the opening, such as a pin configured to engage a hole of the locking section. Alternatively or additionally, the monitor device may comprise a recess for receiving the coupling part of the base plate and/or the sensor assembly part. For example, the monitor device coupling part may be provided by the recess for receiving the coupling part of the base plate and/or the sensor assembly part. The locking mechanism may comprise a locking component positioned inside the recess, such as a pin configured to engage a hole of the locking section.

The base plate and/or the sensor assembly part and/or the monitor device may comprise a locking element (may alternatively be denoted an unlocking element). The locking element(s) may form part of the locking mechanism(s). The locking element(s) may be configured to unlock and/or lock the locking mechanism(s), e.g. upon user interaction with the locking element(s). For example, the locking element(s) may comprise button(s) for user interaction. For example, the locking element(s) may be engaged to lock the locking mechanism and/or the locking element(s) may be engaged to unlock the locking mechanism. User interaction with the locking element(s) may comprise deflection of one or more buttons or sliding of a slider etc.

The locking element(s), such as each of the locking elements, may comprise a first button. The first button may be deflectable in a first direction.

The first direction may be substantially perpendicular to the engagement direction, and/or the first direction may be substantially perpendicular to the disengagement direction. Alternatively, the first direction may be substantially parallel to the engagement direction, and/or the first direction may be substantially parallel to the disengagement direction. For example, the first direction may be substantially the same as the engagement direction and/or the disengagement direction. Alternatively, the first direction may be substantially opposite the engagement direction and/or the disengagement direction.

The locking element(s) may comprise a second button, such as a first button and a second button. The second button may be deflectable in a second direction.

The first direction may be substantially opposite the second direction. The first direction and the second direction being opposite may provide that the first button and the second button may be deflected, e.g. engaged, simultaneously by the user pinching the monitor device.

The first direction and/or the second direction may be substantially perpendicular to the engagement direction, and/or the first direction may be substantially parallel to the disengagement direction. Thereby, the user may pinch the monitor device and push/pull in the engagement direction and/or the disengagement direction.

The locking element(s) may comprise a slider. The slider may be slidable in a first slider direction. The slider may be spring loaded and biased towards a second slider direction. The first slider direction may be opposite the second slider direction. The first slider direction and/or the second slider direction may be substantially perpendicular to the engagement direction and/or the disengagement direction. Alternatively, the first slider direction and/or the second slider direction may be substantially parallel to the engagement direction and/or the disengagement direction, such as opposite the engagement direction and/or the disengagement direction.

The monitor device may comprise a clamp, such as a clamp configured to clamp the coupling part of the base plate and/or the sensor assembly part between a first clamp surface and a second clamp surface. The locking mechanism may comprise a locking component positioned between the first clamp surface and the second clamp surface. The locking component may be configured to engage the locking section. For example, the locking component may be a pin to engage a hole of the locking section.

The first clamp surface and the second clamp surface may be biased towards each other, such as by a spring and/or by magnetic elements, e.g. provided on the first clamp surface and/or on the second clamp surface. The monitor device may comprise a clamp lock, e.g. configured to lock the first clamp surface and the second clamp surface in a closed clamp position. The clamp lock may be configured to be locked and/or unlocked by user interaction. The locking element, as described above, may function to lock and/or unlock the clamp lock.

The plurality of terminals may be provided on the first clamp surface. Alternatively or additionally, the plurality of terminals may be provided on the second clamp surface. The first clamp surface and/or the second clamp surface may be formed by the monitor device housing.

Also disclosed is a coupling part, such as a coupling part for a base plate and/or a sensor assembly part for an ostomy appliance, such as a coupling part being configured for coupling a monitor device to the base plate and/or the sensor assembly part. The coupling part may be for a base plate and/or a sensor assembly part according to any of the disclosed base plates and/or sensor assembly parts.

The coupling part may comprise a first coupling part section and a second coupling part section. The first coupling part section may be substantially planar in a first coupling part plane and the second coupling part section may be substantially planar in a second coupling part plane.

The first coupling part section may be configured for attachment to a first part of the base plate and/or the sensor assembly part, e.g. a distal side of the first part of the base plate and/or the sensor assembly part, such as a distal side of a first part of the electrode assembly of the base plate and/or the sensor assembly part and/or a distal side of a first part of the top layer of the base plate and/or the sensor assembly part. The first part of the electrode assembly and/or the first part of the top layer may be a first part of the base plate and/or the sensor assembly part comprising connection parts of a plurality of electrodes.

The second coupling part section may be configured for attachment to a second part of the base plate and/or the sensor assembly part, e.g. a distal side of the second part of the base plate and/or the sensor assembly part, such as a distal side of the top layer of the base plate and/or the sensor assembly part and/or a distal side of a second part of the top layer of the base plate and/or the sensor assembly part.

Also disclosed is a base plate and a sensor assembly part, e.g. according to any of the disclosed base plates and sensor assembly parts, comprising a coupling part, e.g. according to the disclosed coupling part, such as a coupling part being configured for coupling a monitor device to the base plate and/or the sensor assembly part. For example, a base plate and/or a sensor assembly part for an ostomy appliance comprising: a top layer; a first adhesive layer; an electrode assembly comprising a plurality of electrodes having connection parts and sensing parts; and a monitor interface configured for connecting the base plate and/or the sensor assembly part to a monitor device. The monitor interface may comprise the coupling part configured for coupling between the monitor device and the base plate and/or the sensor assembly part.

The coupling part may comprise a first coupling part section and a second coupling part section. The first coupling part section may be substantially planar in a first coupling part plane and the second coupling part section may be substantially planar in a second coupling part plane. The first coupling part section may be attached to a first part of the base plate and/or the sensor assembly part comprising the connection parts of the plurality of electrodes, e.g. a first part of the electrode assembly comprising the connection parts and/or a first part of the top layer comprising the connection parts, such as overlaying the first part of the electrode assembly. The first coupling part section may be attached to the first part of the electrode assembly with first parts of other layers in between. A proximal side of the first coupling part section may be attached to a distal side of the top layer, such as a distal side of a first part of the top layer. Alternatively, the proximal side of the first coupling part section may be attached to a distal side of the electrode assembly, such as a distal side of a first part of the electrode assembly.

The second coupling part section may be attached to a second part of the base plate and/or the sensor assembly part, such as a second part of the top layer, such as a distal side of the top layer, e.g. a distal side of the second part of the top layer of the base plate and/or the sensor assembly part. A proximal side of the second coupling part section may be attached to the distal side of the top layer, such as the distal side of a second part of the top layer. The second coupling part section may be, at least partly, attached to a second part of the electrode assembly, such as a distal side of the second part of the electrode assembly of the base plate and/or the sensor assembly part. The proximal side of the second coupling part section may be, at least partly, attached to the distal side of the second part of the electrode assembly.

It is an advantage of the disclosed coupling part and the associated base plate and/or sensor assembly part comprising the disclosed coupling part, that coupling of a monitor device to the base plate and/or the sensor assembly part may be easier and more convenient for the user. Furthermore, coupling of the monitor device to the base plate and/or the sensor assembly part may be made more durable with the disclosed coupling part.

The first coupling part section may be hingedly attached to the second coupling part section allowing a rotational movement of the first coupling part section relative to the second coupling part section about a hinge-axis. The hinge axis may be parallel to the first coupling part plane and the second coupling part plane. The allowed rotational movement may include a position wherein the first coupling part section and the second coupling part section are substantially parallel and/or wherein the first coupling part section and the second coupling part section are substantially in continuation.

The allowed rotational movement of the first coupling part section relative to the second coupling part section about the hinge-axis may be limited. For example, the allowed rotation may be between a first coupling part angle and a second coupling part angle. The first coupling part angle may be between 0 and 10 degrees, such as between 0 and 5 degrees, such as 0 degrees. The second coupling part angle may be between 10 and 90 degrees, such as between 15 and 45 degrees, such as between 25 and 40 degrees, such as 30 degrees or 35 degrees.

In a resting state the first coupling part section and the second coupling part section and/or the top layer may form a resting angle. The resting state may be a state wherein no force is applied to the first coupling part, and/or the second coupling part. For example, a state where the base plate and/or the sensor assembly part is unpacked and lying flat. Providing the coupling part with a resting angle may aid the user in attaching the monitor device, since the coupling part, e.g. the first coupling part section, is easy to access because it is lifted away from the distal side of the top layer. The resting angle may be more than 0 degrees, such as more than 1 degrees, such as more than 5 degrees, such as more than 10 degrees, such as more than 15 degrees, such as more than 20 degrees. The resting angle may be less than 80 degrees, such as less than 70 degrees, such as less than 60 degrees, such as less than 50 degrees. A larger resting angle may facilitate coupling of the monitor device, while a lower resting angle may provide for optimizing storing of the base plate and/or the sensor assembly part as it provides for a more flat base plate and/or the sensor assembly part assembly.

Angles between the first coupling part section and the second coupling part section, such as the first coupling part angle, the second coupling part angle, and/or the resting angle may be measure relative to a position wherein the first coupling part section and the second coupling part section are substantially parallel and/or wherein the first coupling part section and the second coupling part section are substantially in continuation.

The second coupling part section may comprise a primary second coupling part section and one or more secondary second coupling part sections, e.g. including a first secondary second coupling part section and/or second secondary second coupling part section. The primary second coupling part section may be located on a primary side of the hinge-axis. The one or more secondary second coupling part sections may be located on a secondary side of the hinge-axis. The secondary side of the hinge-axis may be opposite the primary side of the hinge-axis. The second coupling part section extending on both sides of the hinge-axis facilitates increased stability of the coupling part, e.g. when rotating the first coupling part section about the hinge-axis. Furthermore, reduced risk of damaging the electrode assembly during use of the base plate and/or the sensor assembly part is provided.

The first coupling part section may comprise a locking section and/or a plurality of locking sections, e.g. configured to lock a monitor device in a coupled position with the base plate and/or the sensor assembly part. The locking section(s) may be configured to cooperate with a respective locking mechanism, e.g. a locking mechanism of the monitor device.

The locking section(s) may comprise a hole extending through the coupling part, such as the first coupling part section. Alternatively or additionally, the locking section(s) may comprise a protrusion protruding from a surface, such as a first surface, of the coupling part, such as of the first coupling part section. Alternatively or additionally, the locking section(s) may comprise an indent in an edge of the coupling part, such as of the first coupling part section. Alternatively or additionally, the locking section(s) may comprise a first indent in a first edge of the coupling part, such as the first coupling part section, and a second indent in a second edge of the coupling part, such as the first coupling part section. The first edge may be opposite the second edge. Alternatively or additionally, the locking section(s) may comprise a recess in a surface of the coupling part, such as the first coupling part section.

The coupling part, such as the coupling part sections, such as the first coupling part section and/or the second coupling part section may be attached to the electrode assembly and/or the top layer by an adhesive and/or by welding. For example, the first coupling part section may be attached to the first part of the base plate and/or the sensor assembly part, such as the first part of the electrode assembly and/or the first part of the top layer, by a first coupling part section adhesive. Alternatively or additionally, the first coupling part section may be attached to the first part of the base plate and/or the sensor assembly part, such as the first part of the electrode assembly and/or the first part of the top layer, by welding together the first coupling part section and the first part of the base plate and/or the sensor assembly part. The second coupling part section may be attached to the second part of the base plate and/or the sensor assembly part, such as the second part of the top layer, by a second coupling part section adhesive. Alternatively or additionally, the second coupling part section may be attached to the second part of the base plate and/or the sensor assembly part, such as the second part of the top layer, by welding together the second coupling part section and the second part of the base plate and/or the sensor assembly part.

The first coupling part section may comprise a first coupling part section adhesive, e.g. configured for attachment to the first part of the base plate and/or the sensor assembly part, such as the first part of the electrode assembly and/or the first part of the top layer. The second coupling part section may comprise a second coupling part section adhesive, e.g. configured for attachment to the second part of the base plate and/or the sensor assembly part, such as the second part of the top layer.

The coupling part may have one or more thicknesses. The thickness of the first coupling part section may be substantially uniform. The thickness of the second coupling part section may be substantially uniform. The first coupling part section may have a first coupling part thickness. The second coupling part section may have a second coupling part thickness. The first coupling part thickness may be less than 2 mm, such as less than 1 mm, such as 0.6 mm. The second coupling part thickness may be less than 2 mm, such as less than 1 mm, such as 0.6 mm or 0.3 mm. The first coupling part thickness may be more than the second coupling part thickness.

The coupling part may comprise one or more lines of reduced thickness along the hinge-axis, e.g. to allow the rotational movement of the first coupling part section relative to the second coupling part section about the hinge-axis. The thinner thickness along the hinge-axis may facilitate the rotational movement between the first coupling part section and the second coupling part section. The one or more lines of reduced thickness may be provided on a distal side of the coupling part, e.g. to provide for rotational movement in one direction, e.g. in a distal direction for the first coupling part section, and/or to restrict rotational movement in an opposite direction, e.g. in a proximal direction for the first coupling part section. The one or more lines of reduced thickness may include a plurality of lines of reduced thickness, such as two lines of reduced thickness, three lines of reduced thickness, or more than three lines of reduced thickness. The one or more lines of reduced thickness may for example, be provided by kiss-cutting or laser engraving.

Additionally or alternatively, the coupling part may comprise one or more holes along the hinge-axis, e.g. to allow the rotational movement of the first coupling part section relative to the second coupling part section about the hinge-axis. The one or more holes along the hinge-axis may facilitate the rotational movement between the first coupling part section and the second coupling part section. The one or more holes may include a plurality of holes, such as two holes, three holes, four holes, or more than four holes. The one or more holes may for example, be provided by laser cutting or punching.

The base plate and/or the sensor assembly part may comprise a back element. The back element may be provided between the first adhesive layer and the electrode assembly and/or the plurality of electrodes of the electrode assembly. The back element may be provided between the first adhesive layer and the first part of the electrode assembly. The back element may facilitate that a part of the electrode assembly, such as the first part of the electrode assembly is not adhering to the first adhesive layer, such as to allow the part, such as the first part, of the electrode assembly (e.g. together with the first coupling part section of the coupling part) to be turned. Alternatively or additionally, the back element may be used as a stop for cutting of an opening, such as a U-shaped cut.

FIG. 1 illustrates an exemplary ostomy system. The ostomy system 1 comprises an ostomy appliance 2 including a base plate 4. The base plate 4 is adapted to support and an ostomy pouch (not shown). Further, the ostomy system 1 comprises a monitor device 6 and an accessory device 8 (mobile telephone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data to determine monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate has a stoma-receiving opening 18 with a stoma center point. The size and/or shape of the stomal opening 18 is typically adjusted by the user or nurse before application of the ostomy appliance to accommodate the user's stoma.

Figure 2:
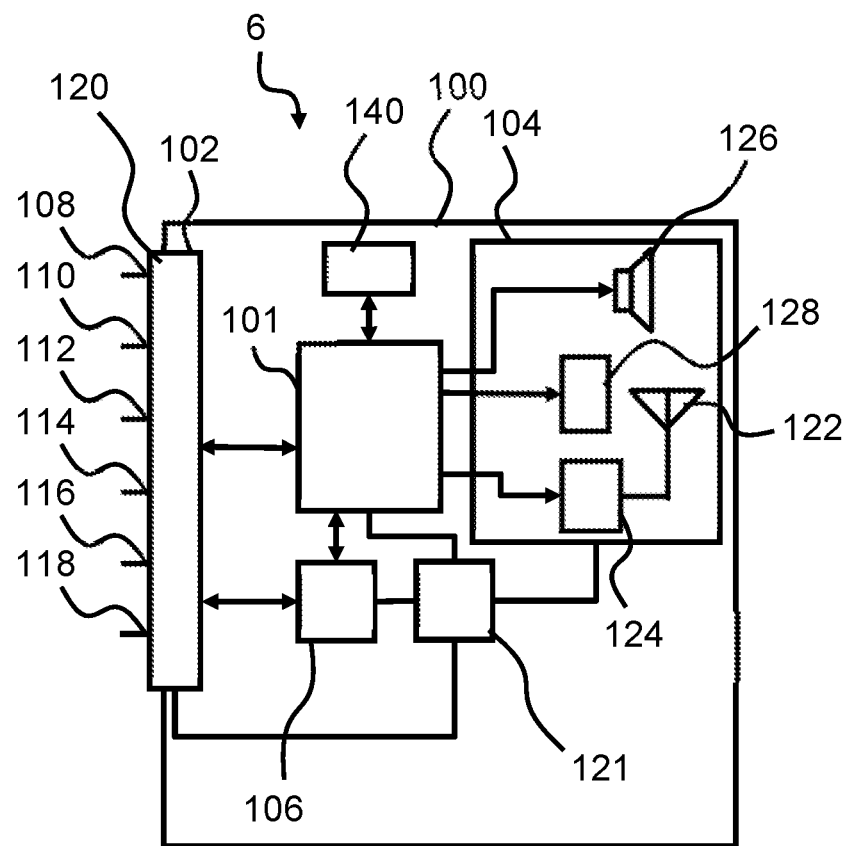
FIG. 2 illustrates an exemplary monitor device of the ostomy system.

The ostomy system 1 optionally comprises a docking station 20 forming an accessory device of the ostomy system 1. The docking station 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes, FIG. 2 is a schematic block diagram of an exemplary monitor device. The monitor device 6 comprises a monitor device housing 100, a processor 101 and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 comprises a sensor unit 140 connected to the processor 101. The sensor unit 140 comprises a temperature sensor for feeding temperature data to the processor and a G-sensor or accelerometer for feeding acceleration data to the processor 101.

The processor 101 is configured to apply a processing scheme, and the first interface 102 is configured for collecting ostomy data from the base plate coupled to the first interface, the ostomy data comprising first ostomy data from a first electrode pair of the base plate, second ostomy data from a second electrode pair of the base plate, and third ostomy data from a third electrode pair of the base plate. The ostomy data may be stored in the memory 106 and/or processed in the processor 101 in order to obtain parameter data. The parameter data may be stored in the memory 106. The processor 101 is configured to apply a processing scheme, wherein to apply a processing scheme comprises obtain first parameter data based on the first ostomy data; obtain second parameter data based on the second ostomy data; obtain third parameter data based on the third ostomy data. In other words, the processor 101 is configured to obtain first, second and third parameter data based on respective first, second and third ostomy data. To apply a processing scheme comprises to determine an operating state of the base plate of the ostomy appliance based on one or more, e.g. all, of the first parameter data, the second parameter data and the third parameter data, wherein the operating state is indicative of a degree of radial erosion of the base plate and/or acute leakage risk for the ostomy appliance. The monitor device 6 is configured to, in accordance with a determination that the operating state is a first operating state, transmit a first monitor signal comprising monitor data indicative of the first operating state of the base plate via the second interface; and in accordance with a determination that the operating state is a second operating state, transmit a second monitor signal comprising monitor data indicative of the second operating state of the base plate via the second interface.

Figure 3:
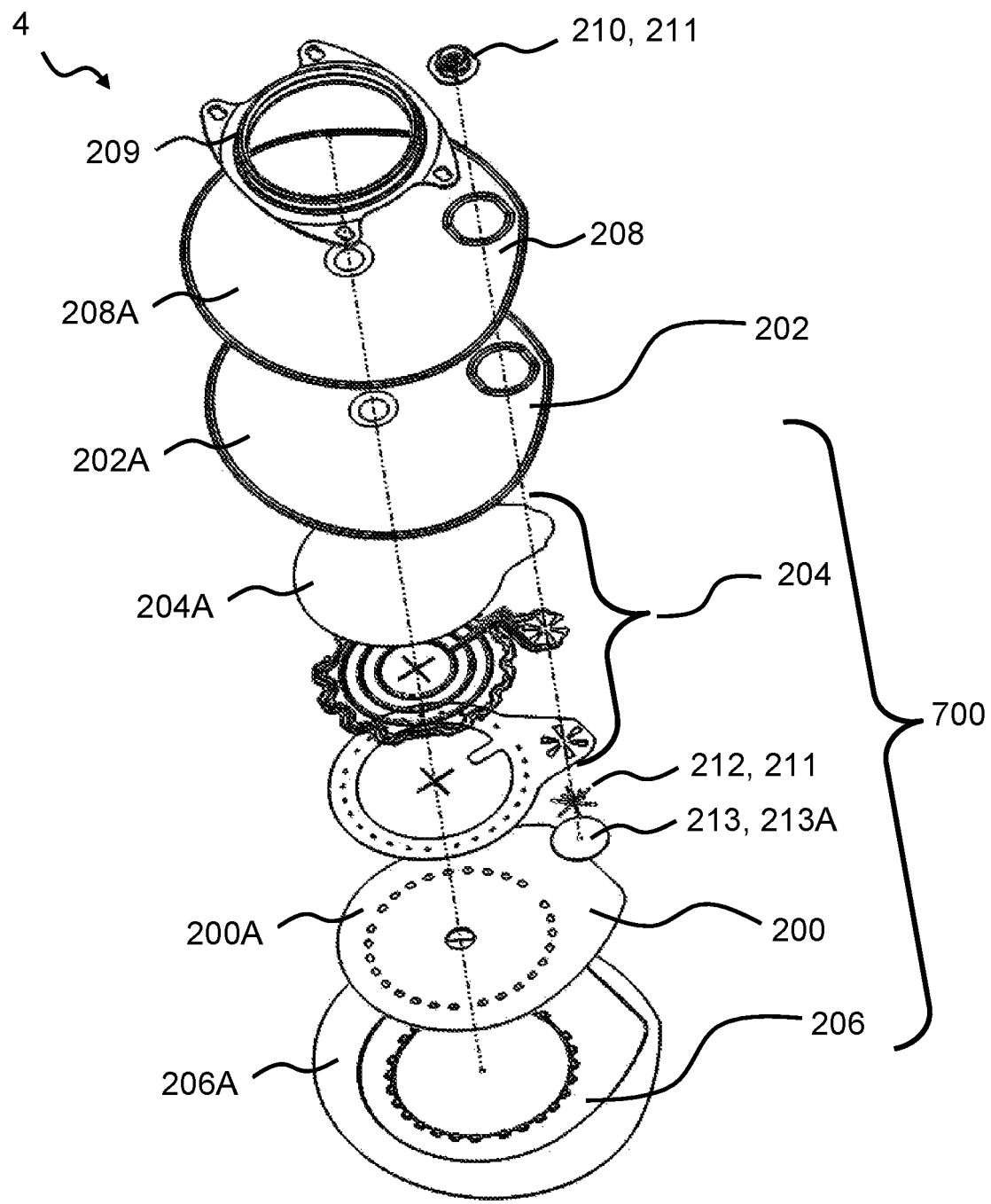
FIG. 3 is an exploded view of a base plate of an ostomy appliance.

FIG. 3 illustrates an exploded view of an exemplary base plate of an ostomy appliance. The base plate 4 comprises a first adhesive layer 200. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with electrodes formed on a proximal surface of the support layer. The base plate 4 comprises a release liner 206 that is peeled off by the user prior to applying the base plate 4 on the skin. The base plate 4 comprises a top layer 208 and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the proximal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

As previously described, some parts of the illustrated base plate 4, may be provided as a separate assembly to be applied to an existing base plate, e.g. comprising one or more of the components as described, such as to provide a base plate like the base plate 4 as described. For example, a sensor assembly part 700 may be provided, e.g. comprising the electrode assembly 204, the first connector 211, the first intermediate element 213, the first adhesive layer 200 and the release liner 206. Additionally, the sensor assembly part 700 may also comprise the second adhesive layer 202 and/or the top layer 208. It may be envisioned that the user may provide a hole in layers of the base plate whereto the sensor assembly part 700 is to be applied, to allow for the first connector 211 of the sensor assembly part 700 to protrude through layers of the base plate whereto the sensor assembly part 700 is applied. Alternatively, the sensor assembly part 700 may be applied to the base plate such that the first connector 211 is positioned outside the periphery of the base plate.

Figure 4:
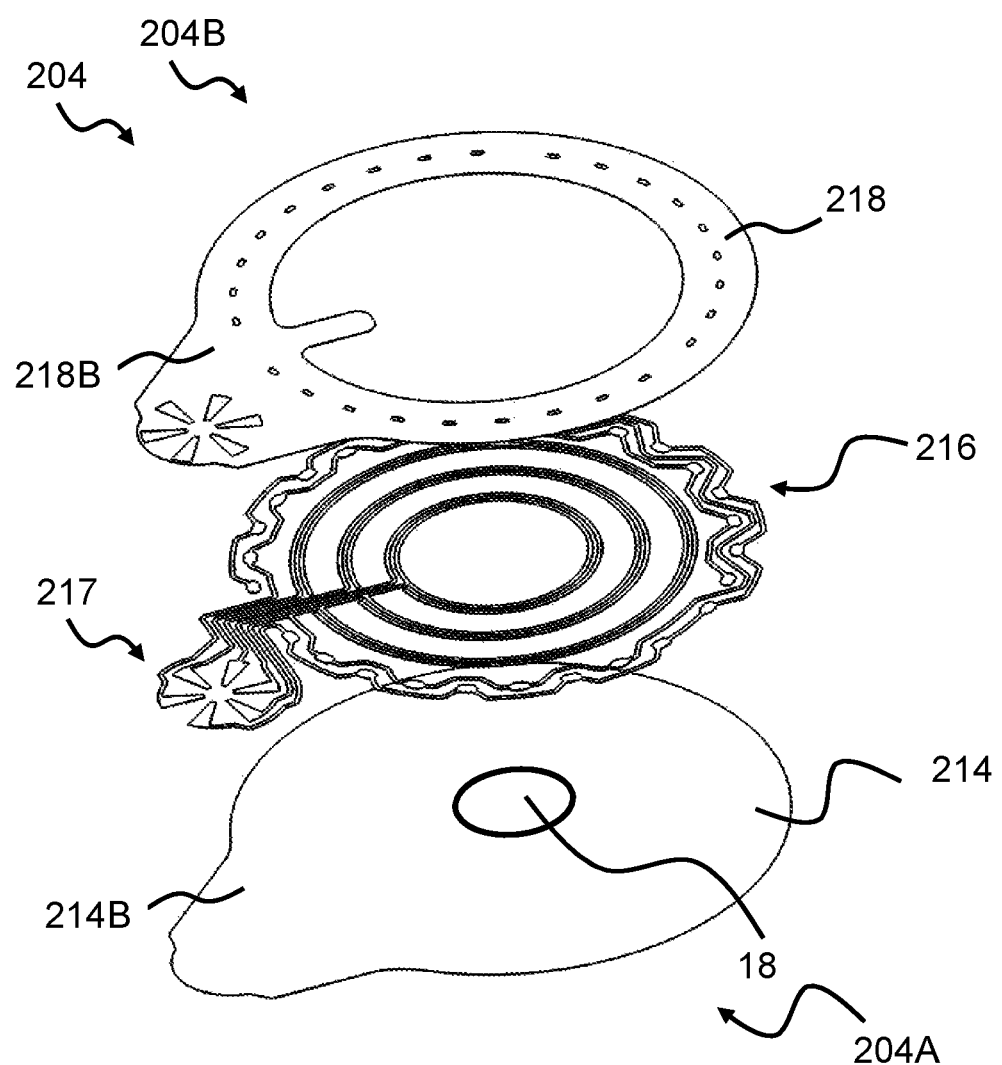
FIG. 4 is an exploded view of an exemplary electrode assembly.

FIG. 4 illustrates an exploded view of an exemplary electrode assembly 204 of a base plate and/or a sensor assembly part. The electrode assembly 204 has a distal side 204A and a proximal side 204B. The electrode assembly comprises a support layer 214 with proximal surface 214B and electrodes 216 including a ground electrode, a first electrode, a second electrode, a third electrode, a fourth electrode, and a fifth electrode, wherein each electrode has a respective connection part 217 for connecting the electrodes 216 to respective terminal elements of the monitor interface. The electrodes 216 are provided, such as formed, on a proximal side 214B of the support layer 214, e.g. the electrodes 216 may be positioned on the proximal side 214B of the support layer. Further, electrode assembly 204 comprises a masking element 218 with proximal surface 218B and configured to insulate electrode parts of electrodes 216 from the first adhesive layer of the base plate and/or the sensor assembly part. The masking element 218 covers or overlap with parts of the electrodes 216 when seen in the axial direction.

Figure 5:
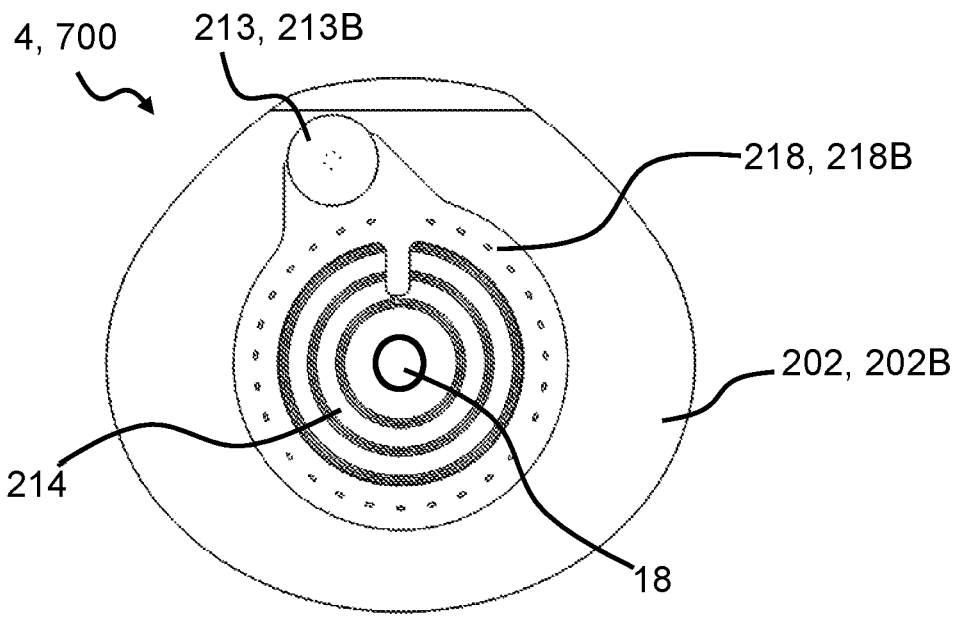
FIG. 5 is a proximal view of parts of a base plate and/or sensor assembly part.

FIG. 5 is a proximal view of proximal surfaces of parts of the base plate and/or the sensor assembly part without the first adhesive layer and the release liner. The base plate 4 and/or the sensor assembly part 700 comprises a first intermediate element 213 on the proximal side of the electrode assembly, i.e. between the electrode assembly 204 and the first adhesive layer (not shown). The first intermediate element 213 covers the terminal elements of the base plate 4 and/or the sensor assembly part 700 when seen in the axial direction and protects the first adhesive layer from mechanical stress from the terminal elements of the base plate and/or the sensor assembly part.

Figure 6:
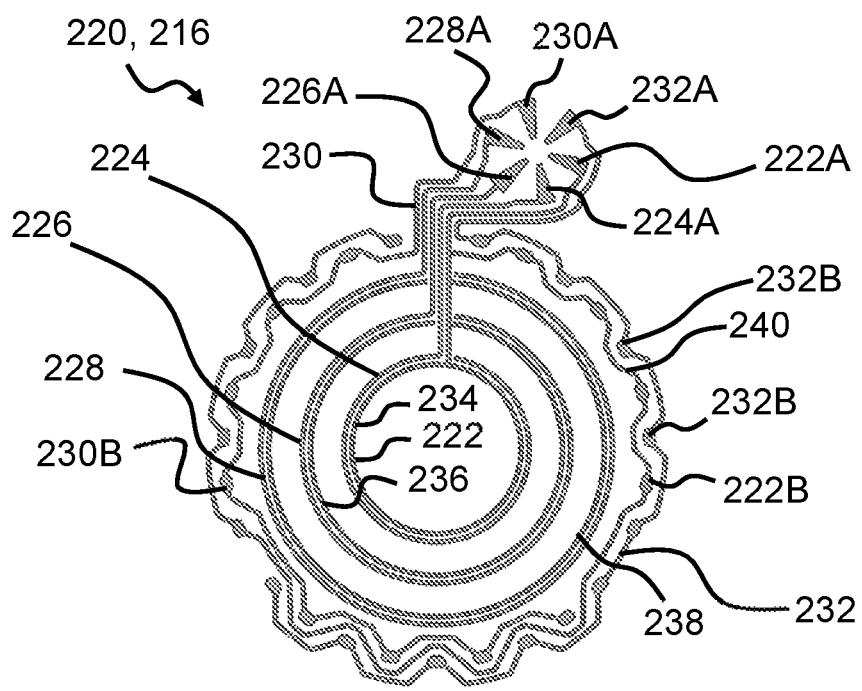
FIG. 6 is a distal view of an exemplary electrode configuration.

FIG. 6 is a distal view of an exemplary electrode configuration 220 of electrodes 216 of the electrode assembly 204. The electrode assembly 204, such as the electrode configuration 220 of the electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode 230 comprises fourth sensing parts 230B. The fifth electrode 232 comprises fifth sensing parts 232B.

Figure 7:
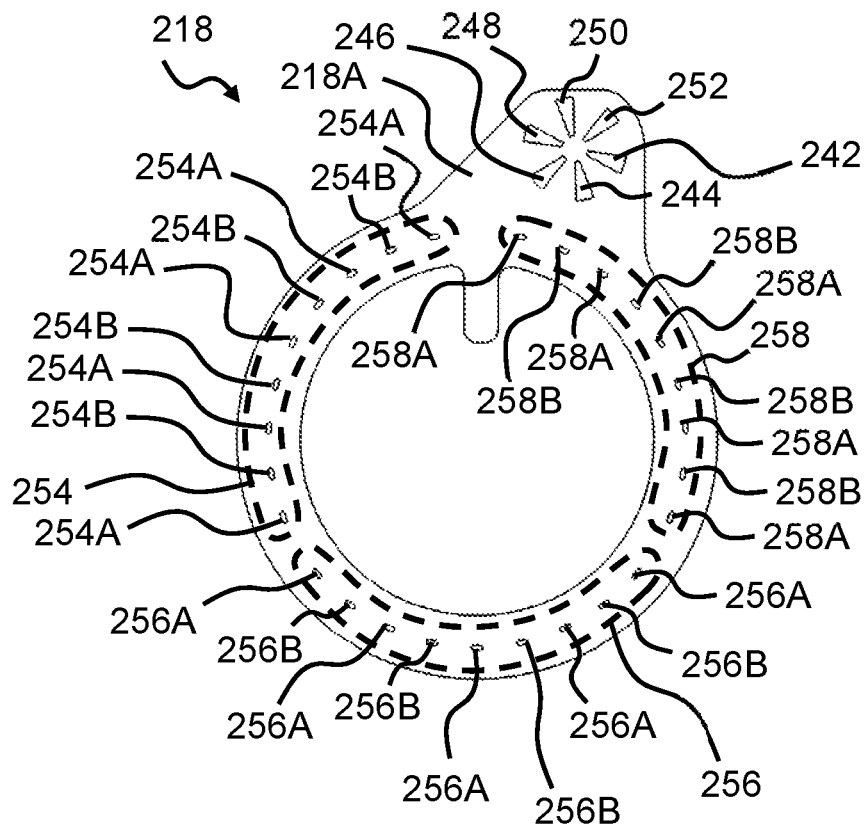
FIG. 7 is a distal view of an exemplary masking element.

The ground electrode 222 comprises a first electrode part 234 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary masking element, four tertiary second sensor point openings 258B each configured to overlap a part of the ground electrode 222.

Figure 8:
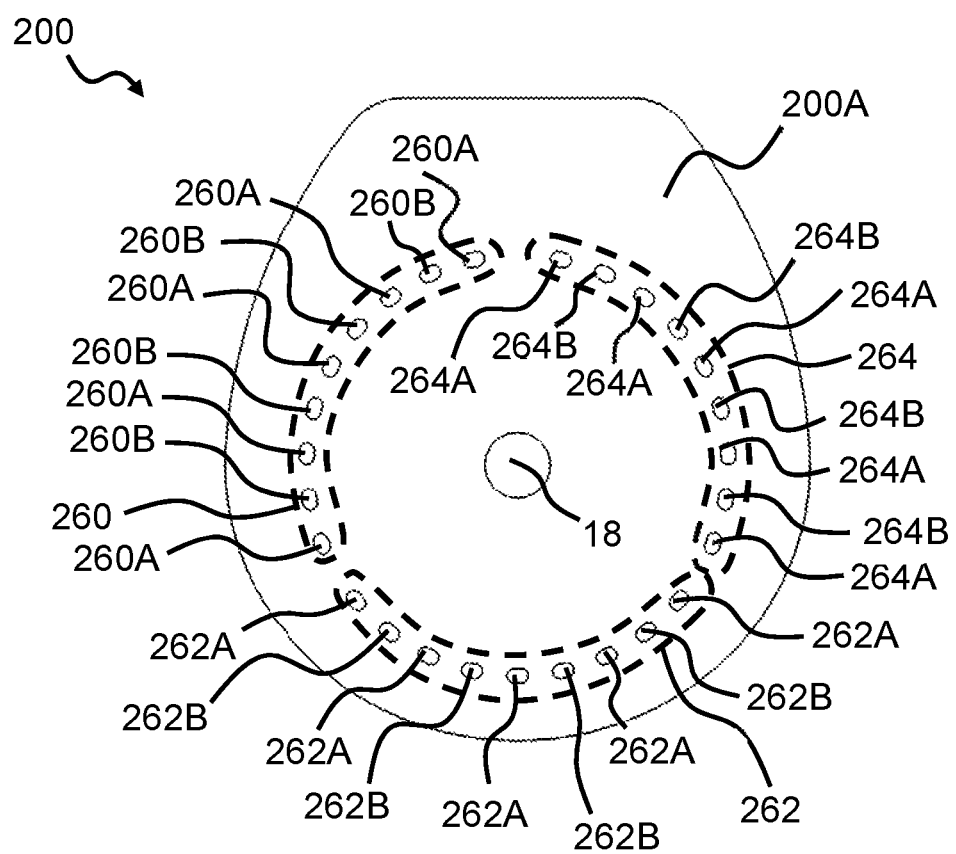
FIG. 8 is a distal view of an exemplary first adhesive layer.
Figure 9:
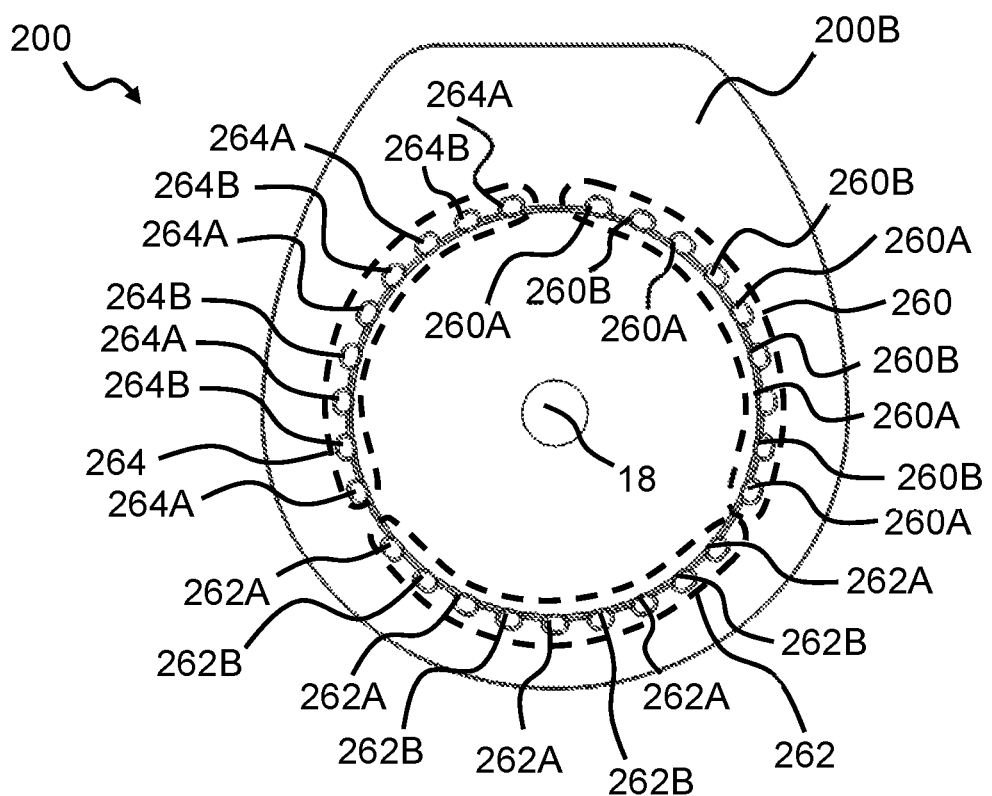
FIG. 9 is a proximal view of the first adhesive layer of FIG. 8.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings 260 comprise, in the illustrated exemplary first adhesive layer, five primary first sensor point openings 260A each configured to overlap a part of the ground electrode 222. The primary sensor point openings 260 comprise, in the illustrated exemplary first adhesive layer, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings 262 comprise, in the illustrated exemplary first adhesive layer, five secondary first sensor point openings 262A each configured to overlap a part of the fifth electrode 232. The secondary sensor point openings 262 comprise, in the illustrated exemplary first adhesive layer, four secondary second sensor point openings 262B each configured to overlap a part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings 264 comprise, in the illustrated exemplary first adhesive layer, five tertiary first sensor point openings 264A each configured to overlap a part of the fifth electrode 232. The tertiary sensor point openings 264 comprise, in the illustrated exemplary first adhesive layer, four tertiary second sensor point openings 264B each configured to overlap a part of the ground electrode 222. FIG. 9 is a proximal view of the first adhesive layer of FIG. 8.

Figure 10:
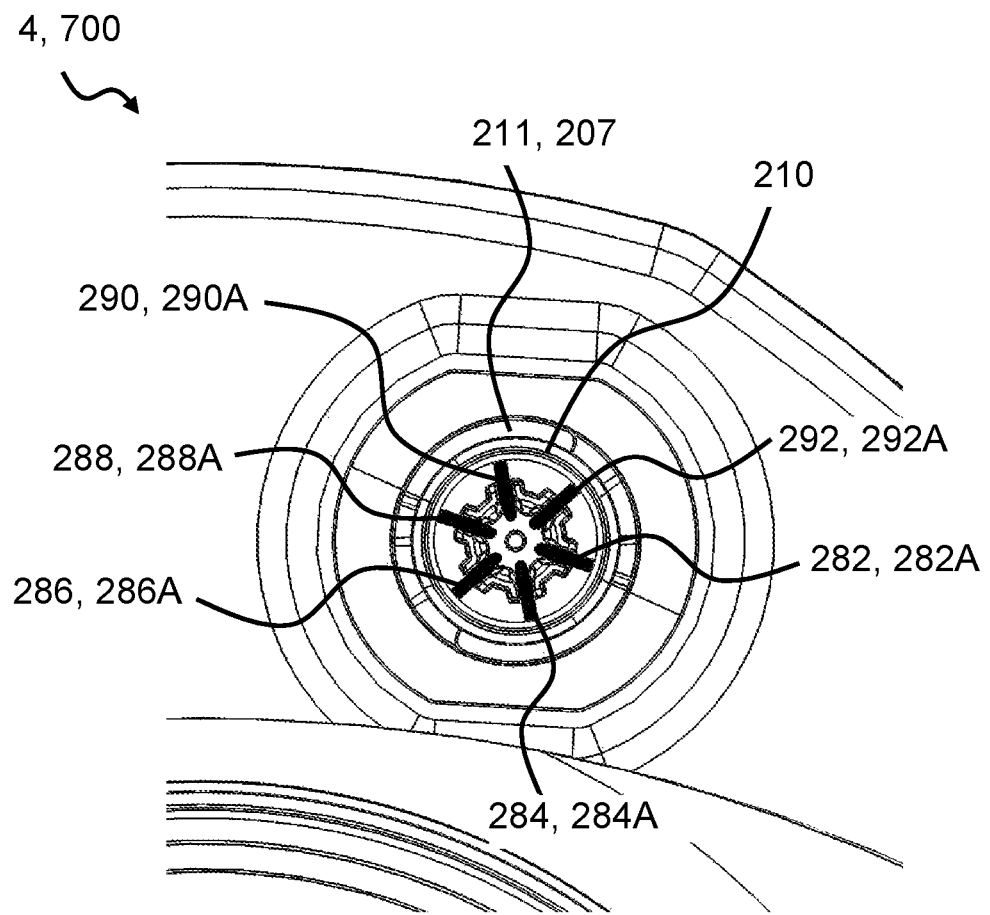
FIG. 10 is a distal view of a part of the base plate and/or sensor assembly part including a monitor interface.

FIG. 10 is a more detailed distal view of a part of the base plate 4 and/or the sensor assembly part 700. The base plate 4 and/or the sensor assembly part 700 comprises a monitor interface 207. The monitor interface 207 of the base plate comprises the first connector 211. The first connector 211 comprises coupling part 210 configured to releasably couple the monitor device to the base plate and/or the sensor assembly part and thus forming a releasable coupling. The first connector 211 of the monitor interface 207 comprises a plurality of terminals formed by respective terminal elements for forming respective electrical connections with respective terminals of the monitor device.

The plurality of terminals of the first connector 211 of the monitor interface 207 comprises a ground terminal element 282 forming a ground terminal 282A, a first terminal element 284 forming a first terminal 284A, a second terminal element 286 forming a second terminal 286A, and a third terminal element 288 forming a third terminal 288A. The monitor interface optionally comprises a fourth terminal element 290 forming a fourth terminal 290A and/or a fifth terminal element 292 forming a fifth terminal 292A. The terminal elements 282, 284, 286, 288, 290, 292 contact respective connection parts 222A, 224A, 226A, 228A, 230a, 232A of electrodes 222, 224, 226, 228, 230, 232.

Figure 11A:
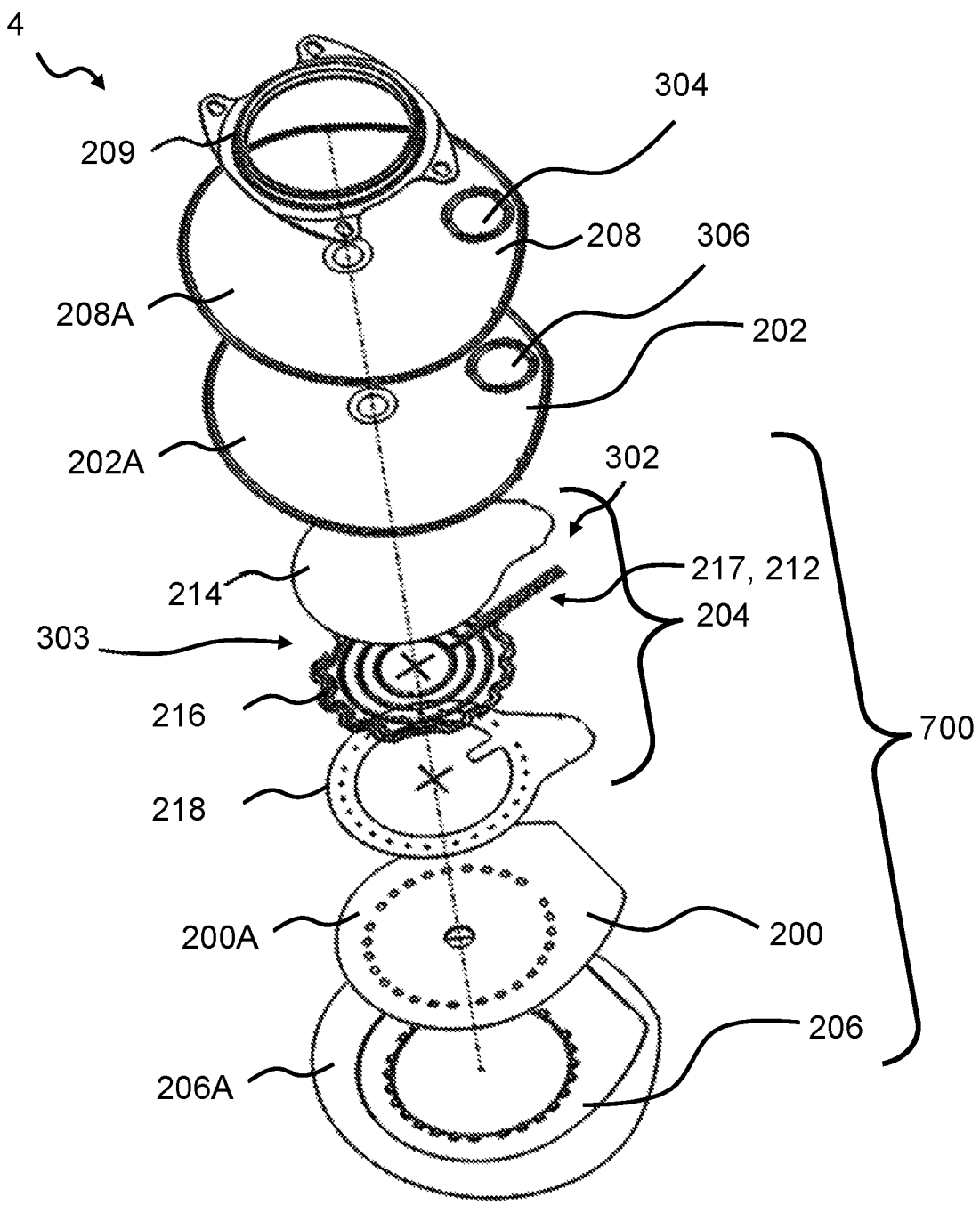
FIG. 11a illustrates an exploded view of an exemplary base plate.

FIG. 11a illustrates an exploded view of an exemplary base plate 4 of an ostomy appliance. The base plate 4 comprises a first adhesive layer 200. The base plate 4 optionally comprises a second adhesive layer 202, also denoted rim adhesive layer. The base plate 4 comprises a plurality of electrodes 216 arranged in an electrode assembly 204. The electrode assembly 204 is arranged between the first adhesive layer 200 and the second adhesive layer 202. The electrode assembly 204 optionally comprises a support layer 214. The electrodes may be formed on a proximal side of the support layer 214, such as by printing of conductive ink. The electrode assembly 204 optionally comprises a masking element 218, e.g. covering or overlapping with parts of the electrodes 216 when seen in the axial direction, e.g. from a proximal side of the electrodes 216. The electrode assembly has a first part 302 comprising connection parts 217 of the plurality of electrodes 216. The electrode assembly has a second part 303. The base plate 4 comprises a release liner 206. The base plate 4 comprises a top layer 208. The base plate 4 optionally comprises a coupling ring 209 for coupling an ostomy pouch to the base plate 4. Alternatively, e.g. for a one-part ostomy appliance, an ostomy pouch may be directly fastened to the base plate 4.

The base plate 4 comprises a monitor interface configured for connecting, such as mechanically and/or electronically connecting, the base plate to a monitor device. The monitor interface comprises a plurality of terminals 212 configured to form electrical connections with respective terminals of the monitor device. For example, as illustrated, the connection parts 217 may form the plurality of terminals 212 of the monitor interface. Alternatively, e.g. as shown in FIG. 3, terminal elements may be provided to form the plurality of terminals.

The top layer 208 comprises a top layer opening 304. The second adhesive layer 202 comprises a second adhesive layer opening 306. The top layer opening 304 and the second adhesive layer opening 306 are configured to allow for connection between the plurality of electrodes 216 of the electrode assembly 204 and terminals of a monitor device being coupled to the base plate 4. For example, the first part 302 of the electrode assembly 216 may extend through the top layer opening 304 and the second adhesive layer opening 306.

Figure 11B:
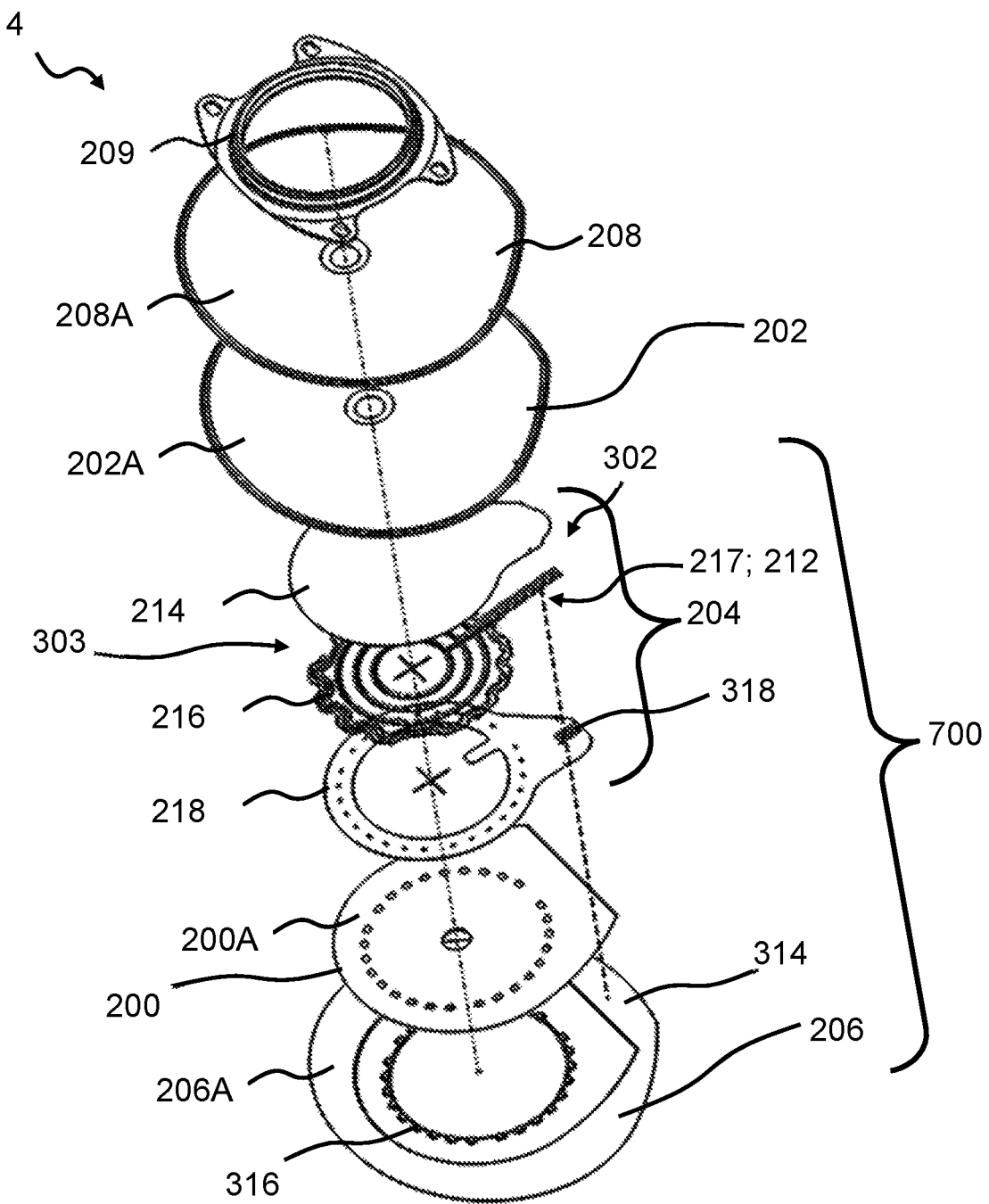
FIG. 11b illustrates an exploded view of an exemplary base plate.

FIG. 11b illustrates an exploded view of an exemplary base plate 4 of an ostomy appliance. The base plate 4 comprises a first adhesive layer 200. The base plate 4 optionally comprises a second adhesive layer 202, also denoted rim adhesive layer. The base plate 4 comprises a plurality of electrodes 216 arranged in an electrode assembly 204. The electrode assembly 204 is arranged between the first adhesive layer 200 and the second adhesive layer 202. The electrode assembly 204 optionally comprises a support layer 214. The electrodes 216 may be formed on a proximal side of the support layer 214, such as by printing of conductive ink on the proximal side of the support layer 214. The electrode assembly 204 optionally comprises a masking element 218, e.g. covering or overlapping with parts of the electrodes 216 when seen in the axial direction, e.g. from a proximal side of the electrodes 216. The electrode assembly 204 has a first part 302 comprising connection parts 217 of the plurality of electrodes 216. The electrode assembly 204 has a second part 303. The second part 303 comprises sensing parts of the plurality of electrodes 216. The base plate 4 comprises a release liner 206. The base plate 4 comprises a top layer 208. The base plate 4 optionally comprises a coupling ring 209 for coupling an ostomy pouch to the base plate 4. Alternatively, e.g. for a one-part ostomy appliance, an ostomy pouch may be directly fastened to the base plate 4.

The base plate 4 comprises a monitor interface configured for connecting, such as mechanically and/or electronically connecting, the base plate 4 to a monitor device. The monitor interface comprises a plurality of terminals 212 configured to form electrical connections with respective terminals of the monitor device. For example, as illustrated, the connection parts 217 may form the plurality of terminals 212 of the monitor interface. Alternatively, e.g. as shown in FIG. 3, terminal elements may be provided to form the plurality of terminals 212.

As illustrated by the dashed line, the layers are aligned such that the first adhesive layer 200 is not covering a primary side, such as a distal side, of the first part 302 of the electrode assembly 204.

The release liner 206 comprises a first elevated part 314 and a plurality of protrusions 316. The first adhesive layer 200 may be provided by scraping a layer of a first composition, such as a first adhesive composition, onto the release liner 206. The increased height of the protrusions 316 and elevated part(s) 314 minimizes the distance between the scraping apparatus and the release liner 206 such that the first composition is not deposited in these areas. Thereby, the protrusions 316 accounts for the sensor point openings (e.g. sensor point openings 260, 262, 264 of FIG. 8) of the first adhesive layer 200, and the first elevated part 314 accounts for the first part 302, such as the primary side of the first part 302, of the electrode assembly 204 not being covered by the first adhesive layer 200.

Furthermore, the first adhesive layer 200 may typically show viscous properties, and the release liner 206 having the protrusions 316 and the first elevated part 314 provides that shape of the first adhesive layer 200, including the sensor point openings, is maintained while the release liner 206 is maintained.

The optional masking element 218 may be provided to insulate the plurality of electrodes 216, or parts of the plurality of electrodes 216. The masking element 218 has a plurality of terminal openings 318 to allow connection to the connecting parts 217 of the plurality of electrodes 216, e.g. from a proximal side of the electrode assembly 204.

As described in respect to FIG. 3, similarly, some parts of the illustrated base plate 4 of FIGS. 11a and 11b, may be provided as a separate assembly, such as a sensor assembly part 700 to be applied to an existing base plate, e.g. comprising one or more of the components as described, such as to provide a base plate like the base plate 4 as described.

Figure 12:
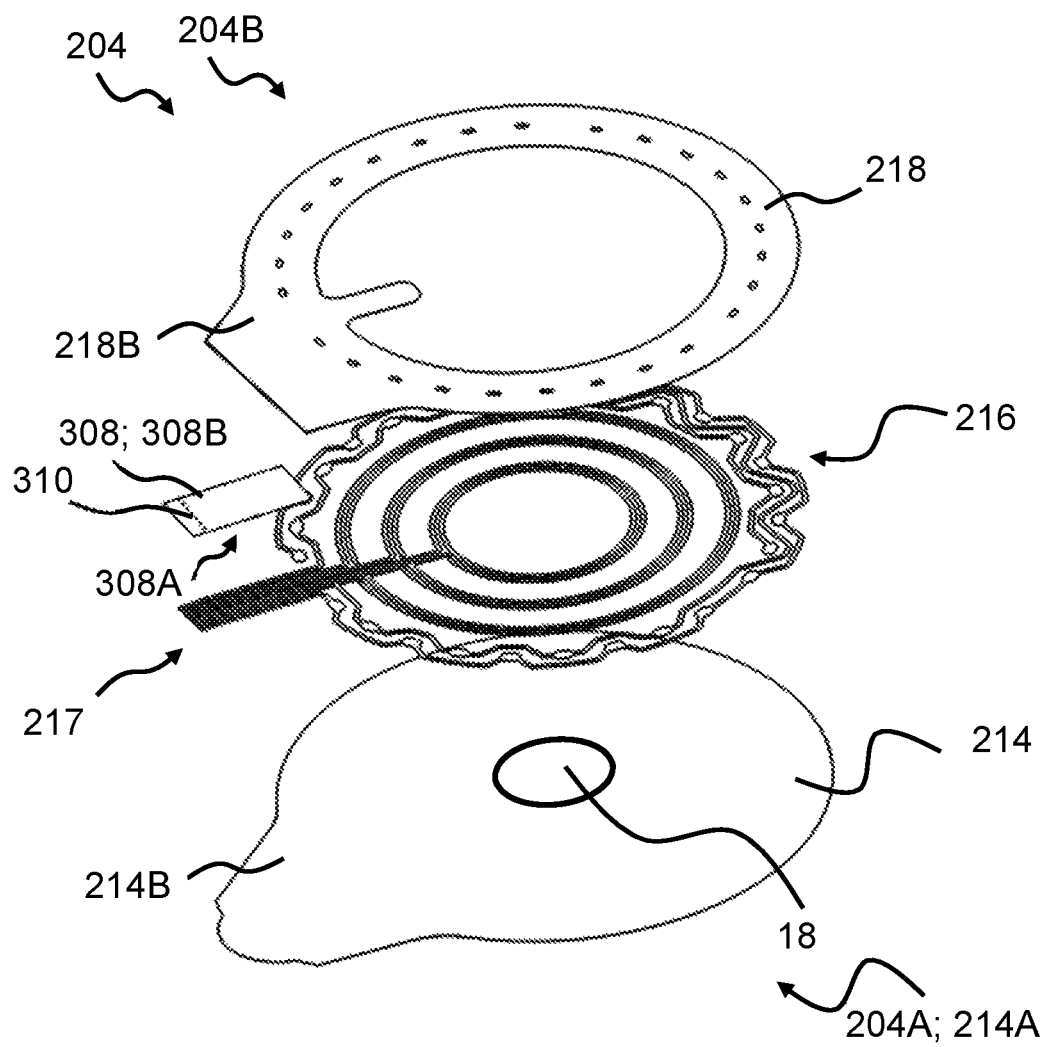
FIG. 12 illustrates an exploded view of an exemplary electrode assembly.

FIG. 12 illustrates an exploded view of an exemplary electrode assembly 204, e.g. of a base plate, such as the base plate 4 of FIG. 11a or FIG. 11b. The electrode assembly 204 has a distal side 204A and a proximal side 204B. The electrode assembly 204 comprises a support layer 214 with a proximal side 214B and a distal side 214A. The electrode assembly 204 comprises a plurality of electrodes 216. Each electrode of the plurality of electrodes 216 has a respective connection part 217 for connecting the electrodes 216 to respective terminal elements of the monitor interface. The electrodes 216 are provided, such as formed, on the proximal side 214B of the support layer 214, e.g. the electrodes 216 may be positioned on the proximal side 214B of the support layer 214. Further, electrode assembly 204 optionally comprises a masking element 218 with proximal side 218B and configured to insulate electrode parts of electrodes 216 from the first adhesive layer 200 of the base plate 4 (see FIG. 11a or FIG. 11b). The masking element 218 covers or overlap with parts of the electrodes 216 when seen in the axial direction, e.g. from the proximal side 204B. The masking element 218 may be configured not to cover or overlap the connecting parts 217 of the plurality of electrodes.

In some exemplary electrode assembly 204, such as the electrode assembly 204 of FIG. 12, the electrode assembly 204 comprises a reinforcement element 308. The reinforcement element 308 may be positioned proximal to the electrode assembly 216, such as proximal to the plurality of electrodes 216, such as proximal to the plurality of connection parts 217 of the plurality of electrodes 216. The reinforcement element 308 may form at least part of a first part of the electrode assembly 204. The reinforcement element 308 may be provided with openings 310 to provide conductive pathways between sides of the reinforcement element 308, such as between a proximal side 308B and a distal side 308A of the reinforcement element 308.

Figure 13:
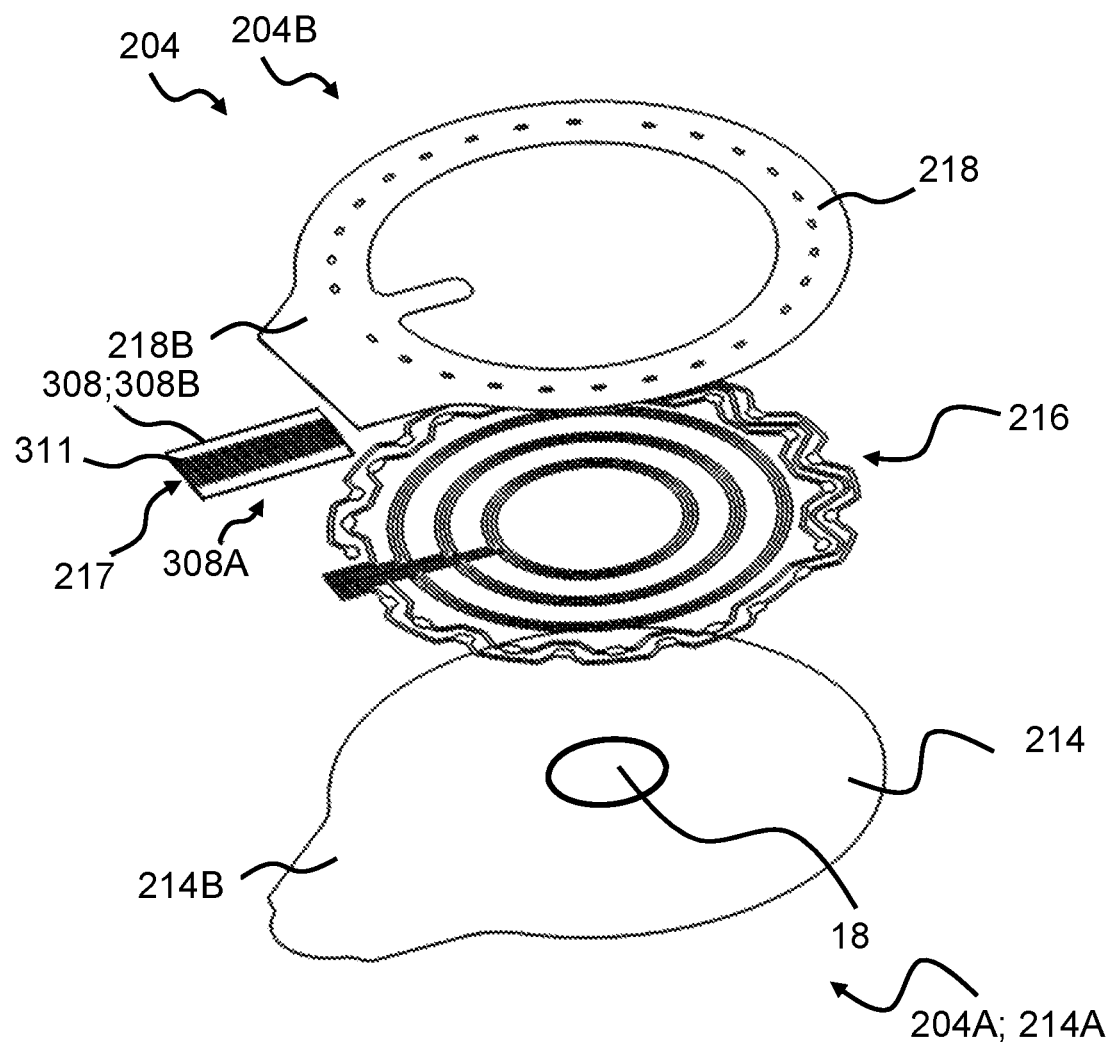
FIG. 13 illustrates an exploded view of an exemplary electrode assembly.

FIG. 13 shows an alternative to FIG. 12, wherein the reinforcement element 308 comprises a plurality of conductive paths 311. For example, the reinforcement element 308 may be a flex circuit. The plurality of conductive paths 311 may be connected to the plurality of electrodes 216. The plurality of conducive paths 311 thereby may form the connection parts 217 of the plurality of electrodes 216. The plurality of conductive paths 311 may provide conductive pathways between the proximal side 308B and the distal side 308A of the reinforcement element 308.

Figure 14:
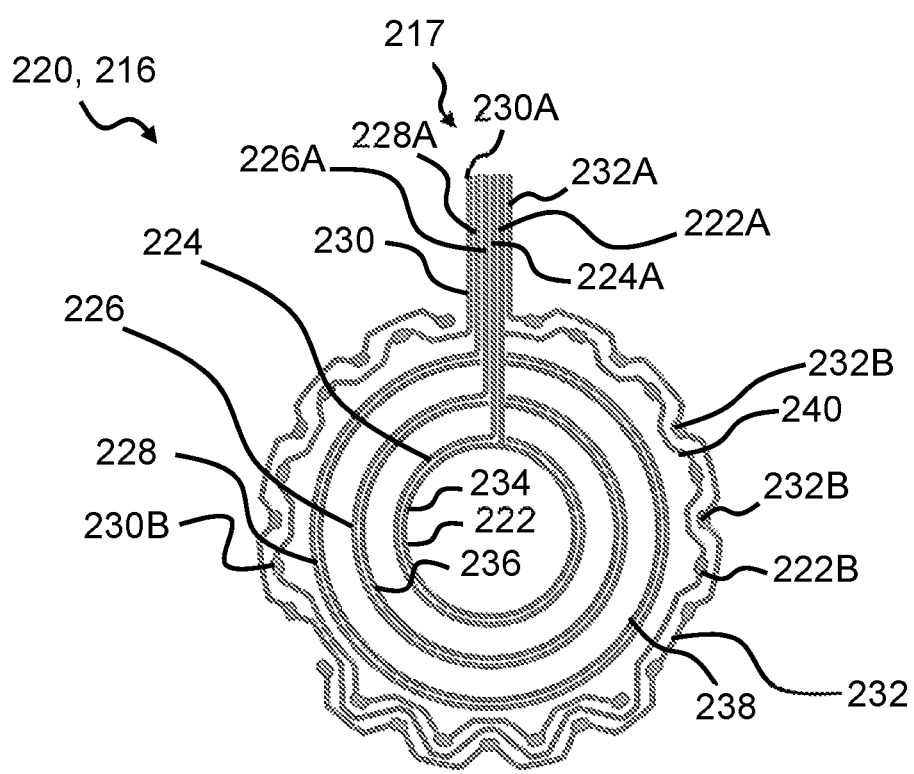
FIG. 14 shows an exemplary electrode configuration.

FIG. 14 shows an exemplary electrode configuration 220 of the plurality of electrodes 216, like the electrode configuration 220 as shown in FIG. 6, with the difference that the connection parts 217, such as the ground connection part 222A, the first connection part 224A, the second connection part 226A, the third connection part 228A, the fourth connection part 230A and/or the fifth connection part 232A, are straight connector parts.

Figure 15:
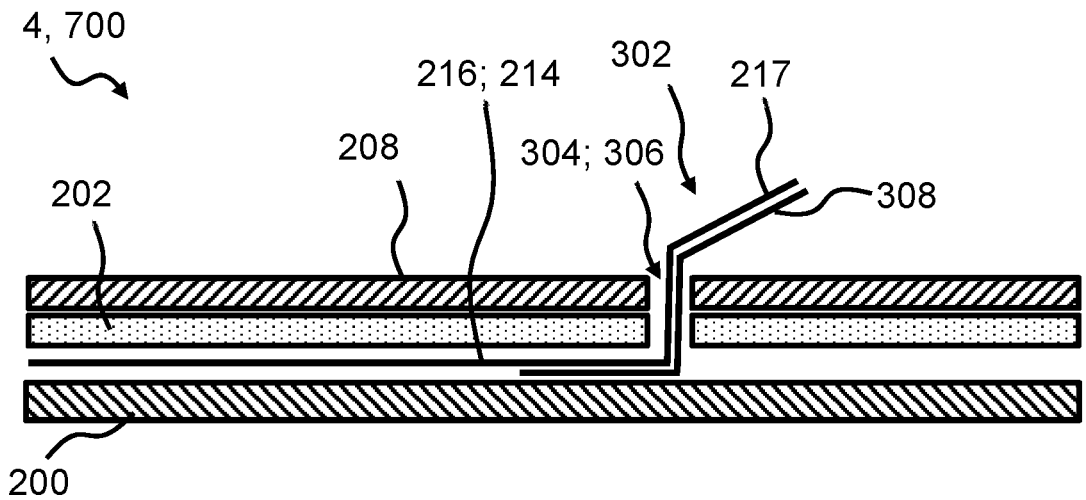
FIG. 15 shows a schematic representation of part of a base plate and/or a sensor assembly part.

FIG. 15, shows a sectional schematic representation of part of a base plate 4 and/or a sensor assembly part 700. The base plate 4 and/or the sensor assembly part 700. comprises a first adhesive layer 200, an optional second adhesive layer 202, and a top layer 208. An electrode assembly comprising a plurality of electrodes 216 is arranged between the first adhesive layer 200 and the top layer 208, such as between the first adhesive layer 200 and the second adhesive layer 202. For example, a second part of the electrode assembly is arranged between the first adhesive layer and the second adhesive layer 202 and/or the top layer 208. The electrode assembly further comprises an optional reinforcement element 308.

The top layer 208 and the second adhesive layer 202 comprise openings 304; 306. The top layer 208 comprises a top layer opening 304. The second adhesive layer 202 comprises a second adhesive layer opening 306. A first part 302 of the electrode assembly extends through the top layer opening 304 and the second adhesive layer opening 306. The first part 302 includes the connection parts of the plurality of electrodes and the reinforcement element 308. The first part 302 may include the support layer 214 or a part of the support layer. Connection to the connection parts 217 of the plurality of electrodes may be provided through the reinforcement element 308 and/or through the support layer 214.

Figure 16:
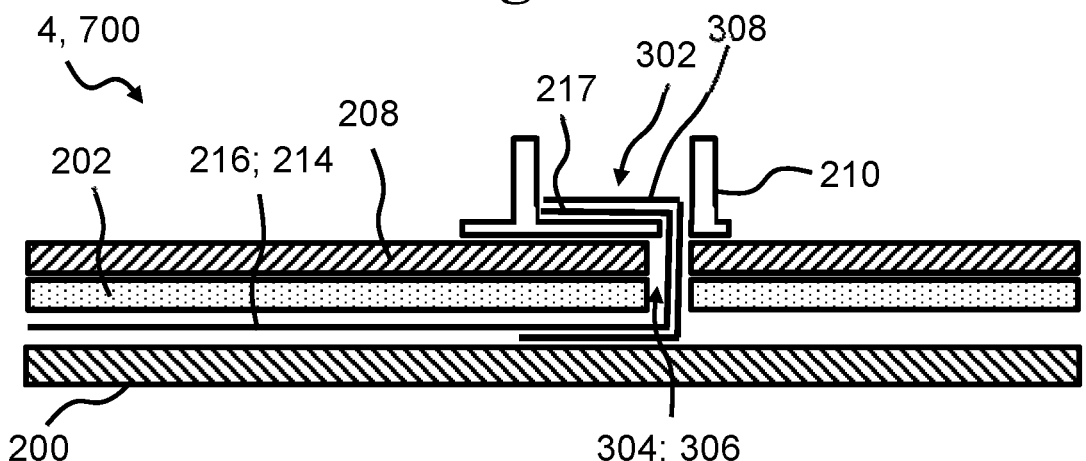
FIG. 16 shows a schematic representation of part of a base plate and/or a sensor assembly par.

FIG. 16, shows a sectional schematic representation of part of a base plate 4 and/or a sensor assembly part 700 as shown in FIG. 15, wherein the base plate 4 and/or the sensor assembly part 700 comprises a coupling part 210. The coupling part 210 is configured for forming a mechanical connection between the monitor device and the base plate 4 and/or the sensor assembly part 700. The first part 302 of the electrode assembly is extending into the coupling part 210, e.g. to allow the monitor device, such as terminals of the monitor device to connect to the electrodes 216 of the base plate 4 and/or the sensor assembly part 700.

In the example shown, the coupling part 210 is attached to the top layer 208. However, in an alternative example, the coupling part 210 is attached to the electrode assembly, in such situation the coupling part 210 may extend through the top layer opening 304 and the second adhesive layer opening 306.

Figure 17:
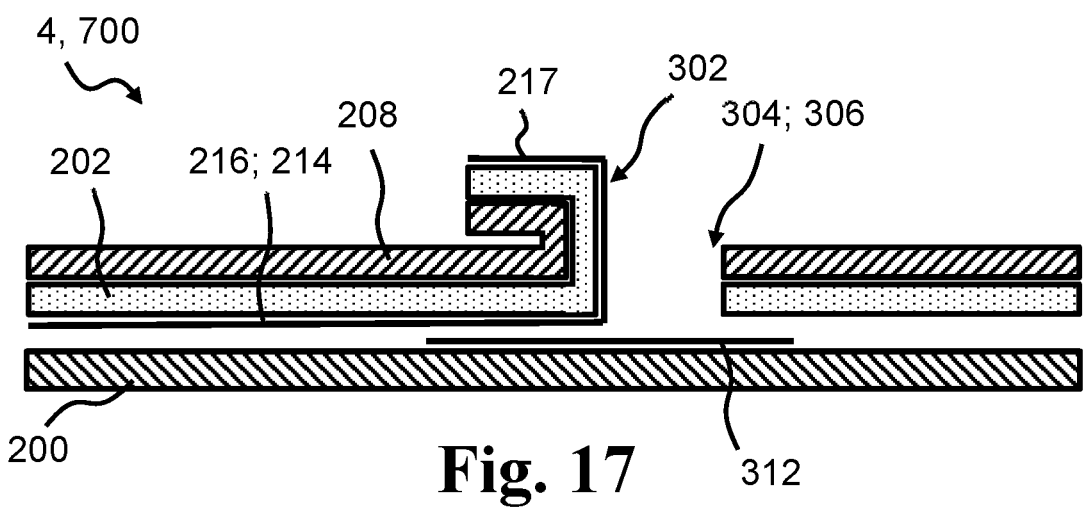
FIG. 17 shows a schematic representation of part of a base plate and/or a sensor assembly par.

FIG. 17, shows a sectional schematic representation of part of a base plate 4 and/or a sensor assembly part 700. The base plate 4 and/or the sensor assembly part 700 comprises a first adhesive layer 200, an optional second adhesive layer 202, and a top layer 208. An electrode assembly comprising a plurality of electrodes 216 is arranged between the first adhesive layer 200 and the top layer 208, such as between the first adhesive layer 200 and the second adhesive layer 202. For example, a second part of the electrode assembly is arranged between the first adhesive layer and the second adhesive layer 202 and/or the top layer 208.

The top layer 208 comprises a top layer opening 304. The second adhesive layer 202 comprises a second adhesive layer opening 306. The top layer opening 304 and the second adhesive layer opening 306 is provided by a U-shaped cut. A first part 302 of the electrode assembly is turned over, together with a part of the top layer 208 and the second adhesive layer 202 inside the U-shaped cut, to expose the connection parts 217 of the plurality of electrodes 216 on a distal side of the base plate 4 and/or the sensor assembly part 700. The first part 302 includes the connection parts 217 of the plurality of electrodes and extends through the top layer opening 304 and the second adhesive layer opening 306. The monitor device may thereby connect to the plurality of connection parts 217. Although not shown in FIG. 17, the electrode assembly may further comprise an optional reinforcement element 308, e.g. as illustrated in FIGS. 15 and 16 and/or the base plate 4 and/or the sensor assembly part 700 may be provided with a coupling part 210, e.g. as shown in FIG. 16.

The base plate 4 and/or the sensor assembly part 700 comprises a back element 312. The back element 312 is provided between the first adhesive layer 200 and the electrode assembly and/or the plurality of electrodes 216 of the electrode assembly, such as between the first adhesive layer 200 and the first part 302 of the electrode assembly. The back element 312 may facilitate that the first part 302 of the electrode assembly is not adhering to the first adhesive layer, such as to allow the first part 302 of the electrode assembly to be turned. A back element 312 may similarly be applied to the exemplary base plates and/or sensor assembly parts as described in relation to FIGS. 15 and/or 16.

Figure 18:
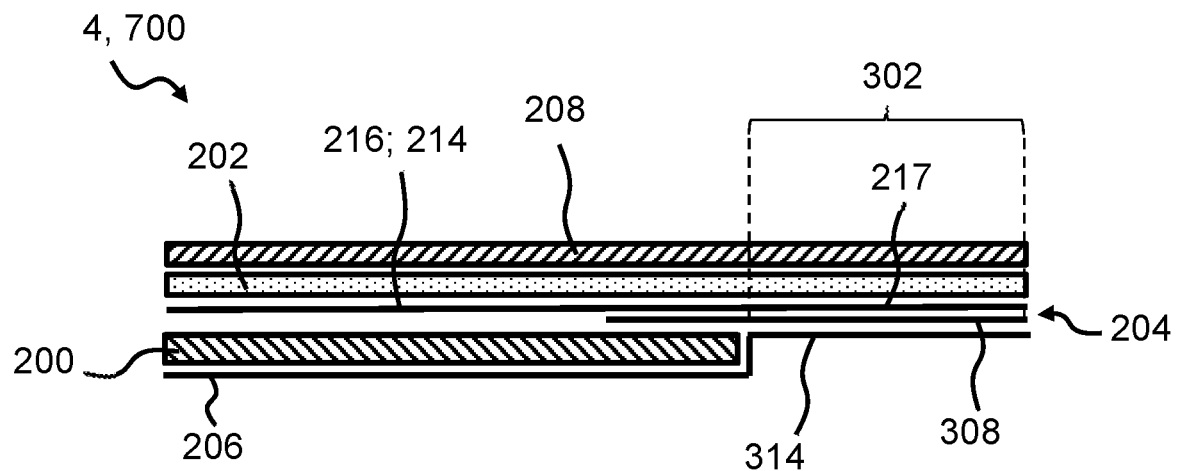
FIG. 18 shows a schematic representation of part of a base plate and/or a sensor assembly par.

FIG. 18, shows a sectional schematic representation of part of a base plate 4 and/or a sensor assembly part 700. The base plate 4 and/or the sensor assembly part 700 comprises a first adhesive layer 200, an optional second adhesive layer 202, and a top layer 208. An electrode assembly 204 comprising a plurality of electrodes 216 is arranged between the first adhesive layer 200 and the top layer 208, such as between the first adhesive layer 200 and the second adhesive layer 202. For example, a second part of the electrode assembly 204 is arranged between the first adhesive layer 200 and the second adhesive layer 202 and/or the top layer 208. The electrode assembly 204 further comprises an optional reinforcement element 308 and an optional release liner 206.

The first adhesive layer 200 is provided such that it does not cover a primary side of a first part 302 of the electrode assembly 204. For example, the release liner 206 comprises a first elevated part 314 such as to facilitate the formation of the first adhesive layer 202 to not cover the primary side of the first part 302 of the electrode assembly 204. The primary side of the first part 302 may be a proximal side of the first part 302. The first part 302 includes the connection parts of the plurality of electrodes 216 and the reinforcement element 308 or part of the reinforcement element 308. The first part 302 may include part of the support layer 214.

Figure 19:
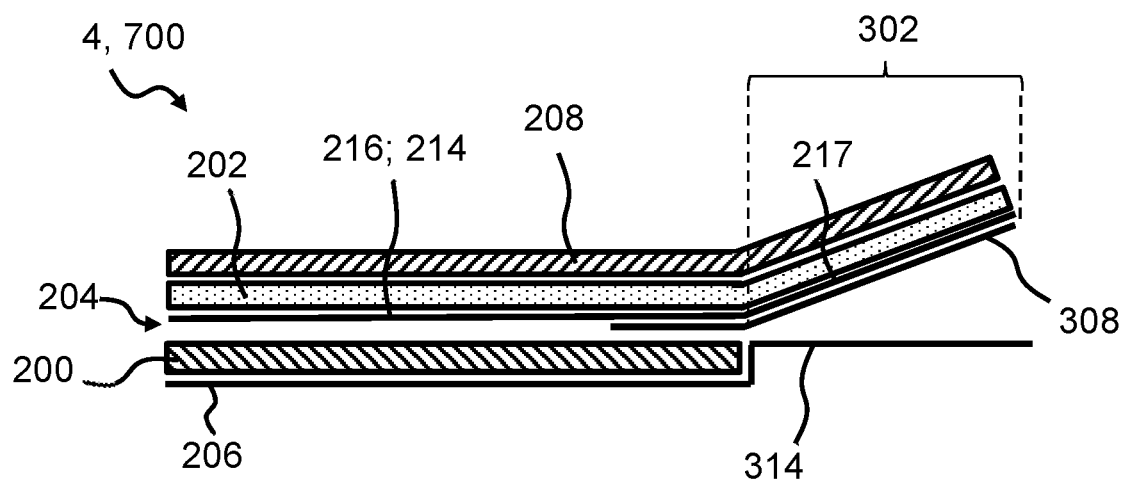
FIG. 19 shows a schematic representation of part of a base plate and/or a sensor assembly par.

FIG. 19, shows a sectional schematic representation of part of a base plate 4 and/or a sensor assembly part 700 as shown in FIG. 18, further illustrating that the connection parts 217 may be accessible, e.g. by slightly bending the first part 302 of the electrode assembly 204 in a distal direction. Alternatively, the release liner 206 may be removed so the first part 302 of the electrode assembly 204 is accessible from a proximal side.

Because the first adhesive layer 200 is not covering the first part 302 of the electrode assembly 204, the first part 302 is not adhered to the release liner or any other proximally positioned layers. Therefore, the connection parts 217 may be accessible, e.g. for connection with a monitor device. Connection to the connection parts 217 of the plurality of electrodes 216 may be provided through the reinforcement element 308, or the connection parts 217 may be formed by conductive paths of the reinforcement element 308.

Figure 20:
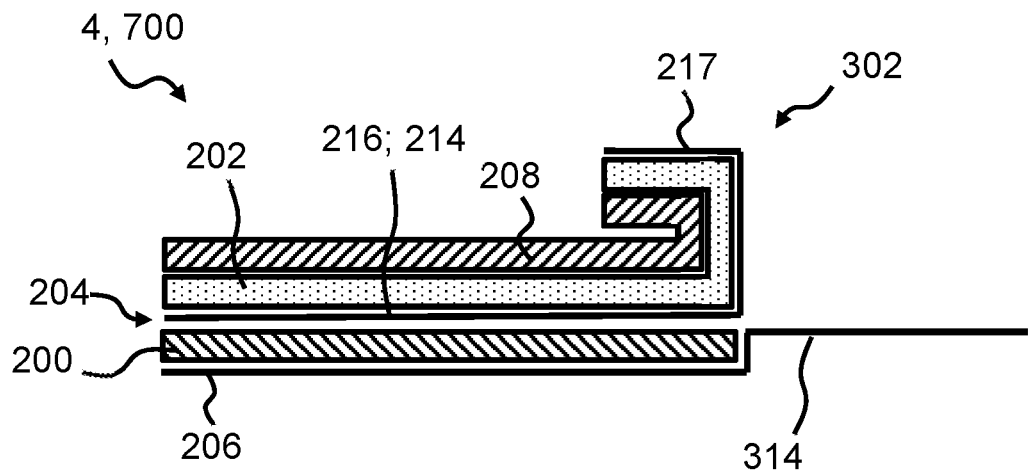
FIG. 20 shows a schematic representation of part of a base plate and/or a sensor assembly par.

FIG. 20, shows a sectional schematic representation of part of a base plate 4 and/or a sensor assembly part 700. The base plate 4 and/or the sensor assembly part 700 comprises a first adhesive layer 200, an optional second adhesive layer 202, and a top layer 208. An electrode assembly 204 comprising a plurality of electrodes 216 is arranged between the first adhesive layer 200 and the top layer 208, such as between the first adhesive layer 200 and the second adhesive layer 202. For example, a second part of the electrode assembly 204 is arranged between the first adhesive layer and the second adhesive layer 202/the top layer 208. Although not illustrated, the electrode assembly 204 may comprise a reinforcement element 308, e.g. as illustrated in FIGS. 18 and 19. Thus, the base plate 4 and/or the sensor assembly part 700 of FIG. 20 may correspond to the base plate 4 and/or the sensor assembly part 700 of FIGS. 18 and 19.

The first part 302 of the electrode assembly 204, together with the top layer 208 and the optional second adhesive layer, has been turned over to expose the connection parts 217 of the plurality of electrodes 216 on a distal side of the base plate 4 and/or the sensor assembly part 700. Thus, the primary side of the first part 302 initially being a proximal side (as shown in FIG. 18) is, after the first part 302 has been turned, facing distally.

Figure 21:
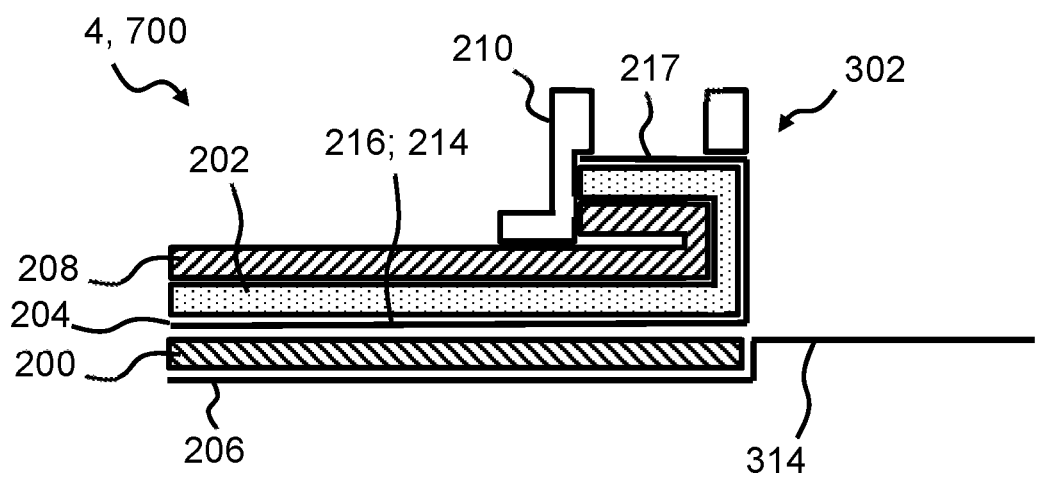
FIG. 21 shows a schematic representation of part of a base plate and/or a sensor assembly par, FIG. 22 schematically illustrates an exemplary base plate and monitor device, FIG. 23 schematically illustrates part of an exemplary base plate and monitor device, FIG. 24 schematically illustrates an exemplary monitor device, FIG. 25 schematically illustrates an exemplary base plate and monitor device, FIG. 26 schematically illustrates part of an exemplary base plate and monitor device, FIG. 27 schematically illustrates an exemplary base plate, FIG. 28 schematically illustrates an exemplary base plate and monitor device, FIG. 29 schematically illustrates an exemplary coupling part, FIG. 30 schematically illustrates an exemplary coupling part, FIG. 31 schematically illustrates an exemplary coupling part, FIG. 32 schematically illustrates an exemplary coupling part, FIG. 33 schematically illustrates an exploded view of an exemplary base plate, and FIG. 34 schematically illustrates an exemplary coupling part and part of an electrode assembly.

FIG. 21, shows a sectional schematic representation of part of a base plate 4 and/or a sensor assembly part 700 as shown in FIG. 20, wherein the base plate 4 and/or the sensor assembly part 700 comprises a coupling part 210. The coupling part 210 is configured for forming a mechanical connection between the monitor device and the base plate 4 and/or the sensor assembly part 700. The first part 302 of the electrode assembly 204 is extending into the coupling part 210, e.g. to allow the monitor device, such as terminals of the monitor device to connect to the electrodes 216 of the base plate 4 and/or the sensor assembly part 700. The coupling part 210 is positioned to cover the connection parts 217 of the plurality of electrodes 216. The coupling part 210 may be attached to the top layer 208 and/or the coupling part 210 may be attached to the electrode assembly 204.

Figure 22:
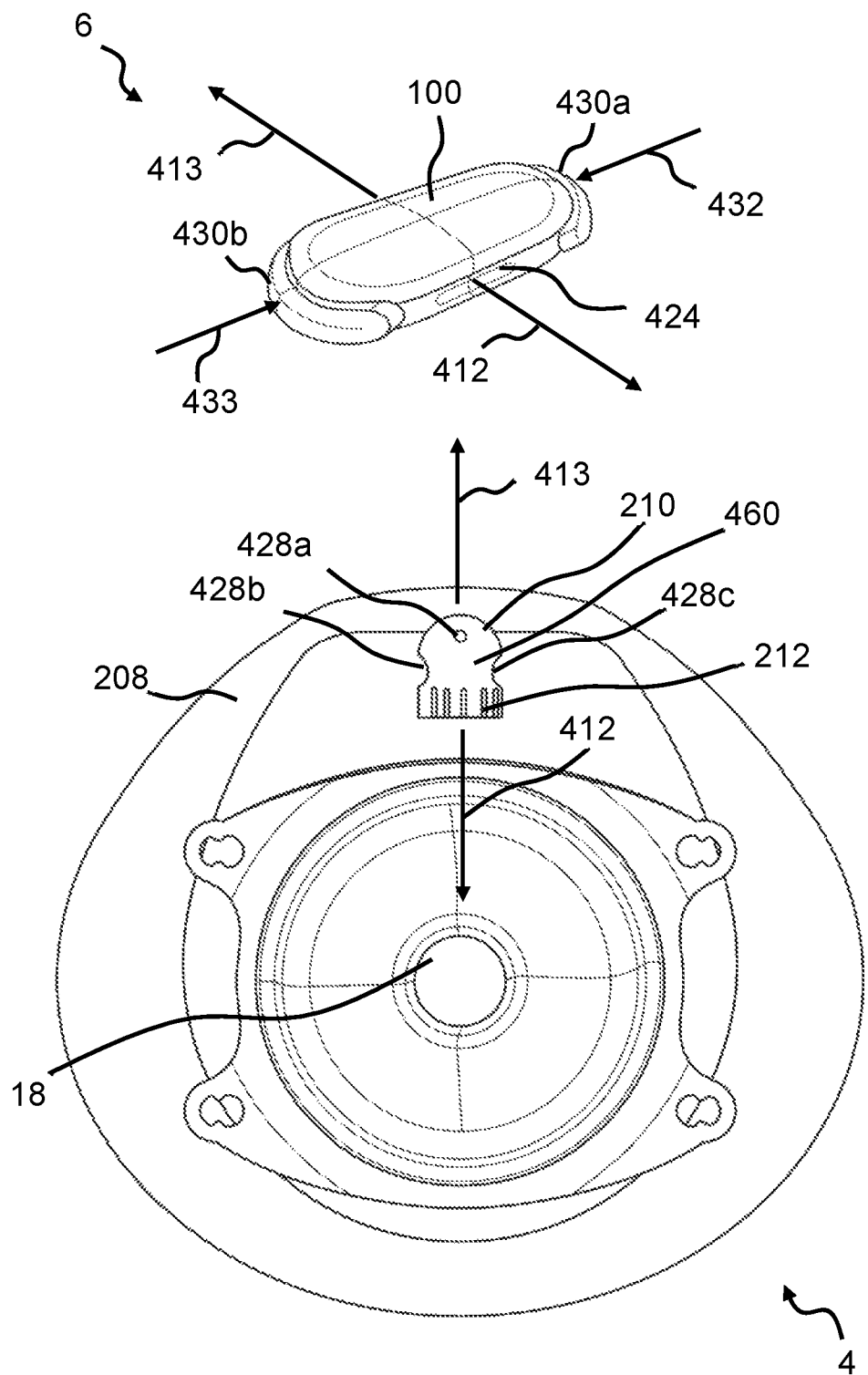

FIG. 22 schematically illustrates an exemplary base plate 4, such as the base plate as illustrated in FIG. 11a or FIG. 11b, and a monitor device 6, such as the monitor device as illustrated in FIG. 2.

The base plate comprises a coupling part 210 configured for coupling between the monitor device 6 and the base plate 4. The coupling part 210 is configured to engage with the monitor device 6 by a linear motion in an engagement direction 412 of the monitor device 6 relative to the base plate 4. The monitor device 6 comprises an opening 424, e.g. in a rim surface of the monitor device 6. The opening 424 may form a monitor device coupling part. The opening 424 is configured to receive the coupling part 210 of the base plate 4. The monitor device 6 is configured to engage with the coupling part 210 of the base plate 4 by the linear motion in the engagement direction 412 of the monitor device 6 relative to the base plate 4. The engagement direction 412 may be towards a stomal opening 18 of the base plate 4.

The plurality of terminals 212 of the base plate is provided on the coupling part 210. The plurality of terminals of the monitor device 6 may be provided inside the opening 424, such as to connect to the plurality of terminals 212 of the base plate 4 when the monitor device 6 is coupled to the base plate 4.

The coupling part 210 is configured to disengage with the monitor device by a linear motion in a disengagement direction 413 of the monitor device 6 relative to the base plate 4. The monitor device 6 is configured to disengage with the coupling part 210 of the base plate 4 by the linear motion in the disengagement direction 413 of the monitor device 6 relative to the base plate 4. The disengagement direction 413 may be away from the stomal opening 18 of the base plate 4.

The top layer 208 and the first adhesive layer 200 are substantially planar, e.g. prior to being applied to a user's skin, and extending in a base plate plane. The engagement direction 412 and the disengagement direction 413 are substantially parallel to the base plate plane.

The monitor device 6 and/or the base plate 4 comprises a locking mechanism configured to lock the monitor device 6 in a coupled position with the base plate 4. The locking mechanism comprises a locking element 430 comprising a first button 430a and a second button 430b.

The first button 430a is deflectable in a first direction 432 and the second button 430b is deflectable in a second direction 433. The first direction 432 is substantially opposite the second direction 433. The first direction 432 and the second direction 433 are substantially perpendicular to the engagement direction 412 and the disengagement direction 413, such as to allow the user to pinch the first button 430a and second button 430b while engaging or disengaging the monitor device 6 to the base plate 4.

The locking element 430 is configured to unlock and/or lock the locking mechanism, such as to unlock the monitor device 6 in the coupled position with the base plate 4 and/or to lock the monitor device 6 in the coupled position with the base plate 4. For example, the first button 430a and the second button 430b is to be pressed simultaneously to lock and/or unlock the monitor device 6 in the coupled position with the base plate 4. For example, the first button 430a and the second button 430b may be pressed in order to lock the monitor device 6 in the coupled position with the base plate 4, and subsequently the first button 430a and the second button 430b may be pressed again to unlock the monitor device 6 in the coupled position with the base plate 4. Alternatively, the locking mechanism may be biased, such as spring biased, towards locking of the monitor device 6 in the coupled position with the base plate 4, e.g. the locking mechanism may be biased towards locking of the locking mechanism, and the first button 430a and the second button 430b may be pressed to unlock the monitor device 6 in the coupled position with the base plate 4. The locking element 430 is, in the illustrated example, provided on the monitor device 6. However, in another exemplary monitor device and/or base plate, the locking element 430 may be provided on the base plate 4, such as on the coupling part 210 of the base plate 4.

The locking mechanism of the monitor device 6 is configured to cooperate with a locking section 428 of the base plate 4. The locking section 428 in the illustrated example comprises a hole 428a extending through the coupling part 210, a first indent 428b in a first edge of the coupling part 210 and a second indent 428c in a second edge of the coupling part 210. For example, the locking mechanism of the monitor device 6 may comprise a locking component, e.g. a pin, positioned inside the opening 424 and being configured to protrude through the hole 428a. Thus, for example, the locking mechanism of the monitor device 6 may comprise a pin to engage with the hole 428a of the coupling part 210 of the base plate 4, and/or the locking mechanism of the monitor device 6 may comprise elements being deflectable perpendicular to the engagement direction 412, such as to engage with the first indent 428b and/or the second indent 428c.

Figure 23:
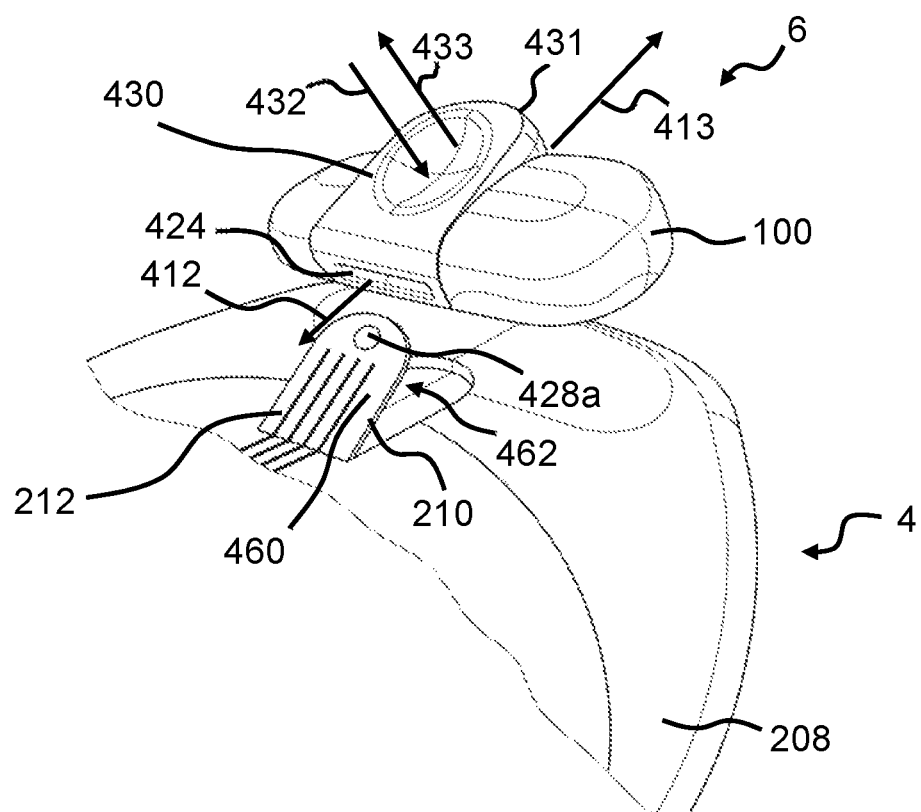

The coupling part 210 is substantially flat and comprises a first surface 460 and a second surface 462 (see FIG. 23). The second surface 462 is facing the top layer 208 and the first surface is facing away from the top layer 208. The second surface 462 may be facing substantially in a proximal direction and the first surface 460 may be facing substantially in a distal direction. The plurality of terminals 212 may be provided on the first surface 460 and/or on the second surface 462 of the coupling part 210.

The second surface of the coupling part 210 and the top layer 208 are separated, such as to allow at least a part of the monitor device 6 to be positioned between the second surface of the coupling part 210 and the top layer 208, e.g. to allow the coupling part 210 to be received by the opening 424 of the monitor device 6.

FIG. 23 schematically illustrates part of an exemplary base plate 4, such as the base plate as illustrated in FIG. 11a or FIG. 11b, and a monitor device 6, such as the monitor device as illustrated in FIG. 2. The base plate 4 of FIG. 23 is similar to the base plate 4 as illustrated in relation to FIG. 22.

The monitor device 6 as shown in FIG. 23 comprises an opening 424, e.g. in a rim surface of the monitor device 6. The opening 424 is configured to receive the coupling part 210 of the base plate 4. The monitor device 6 is configured to engage with the coupling part 210 of the base plate 4 by a linear motion in the engagement direction 412 of the monitor device 6 relative to the base plate 4. The monitor device 6 is configured to disengage with the coupling part 210 of the base plate 4 by a linear motion in the disengagement direction 413 of the monitor device 6 relative to the base plate 4.

The plurality of terminals 212 of the base plate is provided on the coupling part 210. The plurality of terminals of the monitor device 6 may be provided inside the opening 424, such as to connect to the plurality of terminals 212 of the base plate 4 when the monitor device 6 is coupled to the base plate 4.

The monitor device 6 comprises a locking mechanism configured to lock the monitor device 6 in a coupled position with the base plate 4. The locking mechanism of the monitor device 6 is configured to cooperate with the locking section 428 of the base plate 4. The locking section 428 in the illustrated example comprises a hole 428a extending through the coupling part 210. For example, the locking mechanism of the monitor device 6 may comprise a locking component, e.g. a pin, positioned inside the opening 424 and being configured to protrude through the hole 428a. As opposed to the example shown in FIG. 22, the locking section 428 of FIG. 23 does not comprise the indentations 428b, 428c. However, it is noted that the locking section 428 of FIG. 22 may optionally comprise the indentations 428b, 428c, as shown in FIG. 22.

The locking mechanism comprises a locking element 430 comprising a first button 430a. The locking element 430, such as the first button 430a, further comprises a locking element protrusion 431. The first button 430a is deflectable in a first direction 432 and the locking element protrusion 431 is configured for the user to pull/push the first button 430a in a second direction 433, opposite the first direction 432. The locking element 430 may be configured for a rotational movement about an axis substantially perpendicular to the engagement direction 412 and the disengagement direction 413 and substantially parallel to a base plate plane.

The locking element 430 is configured to unlock and/or lock the locking mechanism, such as to unlock the monitor device 6 in the coupled position with the base plate 4 and/or to lock the monitor device 6 in the coupled position with the base plate 4. For example, the user may push the first button 430a in the first direction, e.g. to lock the locking mechanism, and the user may subsequently push/pull the first button 430a by the locking element protrusion 431 in the second direction, e.g. to unlock the locking mechanism.

Hence, the user may linearly move the monitor device 6 in the engagement direction 412, such that the coupling part 210 is received in the opening 424, and hereafter, the user may push the first button 430a in the first direction to lock the locking mechanism, and the monitor device is locked, such as retained, in the coupled position with the base plate. Subsequently, in order to remove the monitor device 6 from the base plate 4, the user may push/pull the locking element protrusion 431 in the second direction 433 to unlock the locking mechanism, and the user may disengage the monitor device 6 from the base plate 4 by moving the monitor device 6 in the disengagement direction 413.

The locking element 430 may be configured to be positioned in a plurality of predefined positions, e.g. including a locked position and a first unlocked position. The predefined positions may be positions of the locking element 430 where a greater force is needed to change the position of the locking element 430. The plurality of predefined positions may include a second unlocked position, such as a cleaning position, where the locking element 430 is opened to allow cleaning of the interior of the opening 424. The locking element may be brought from the locked position to the first unlocked position by movement in the second direction 433, e.g. by an angular movement of the locking element 430 of between 10-75 degrees. The locking element may be brought from the first unlocked position to the second unlocked position by (further) movement in the second direction 433, e.g. by an angular movement of the locking element 430 of between 90-170 degrees. The locking element 430 may be brought from the second unlocked position to the first unlocked position by movement in the first direction 432, e.g. by an angular movement of the locking element 430 of between 90-170 degrees. The locking element 430 may be brought from the first unlocked position to the locked position by (further) movement in the first direction 432, e.g. by an angular movement of the locking element 430 of between 10-75 degrees. An angular distance between the locked position to the second unlocked position may be between 100-200 degrees.

Figure 24:
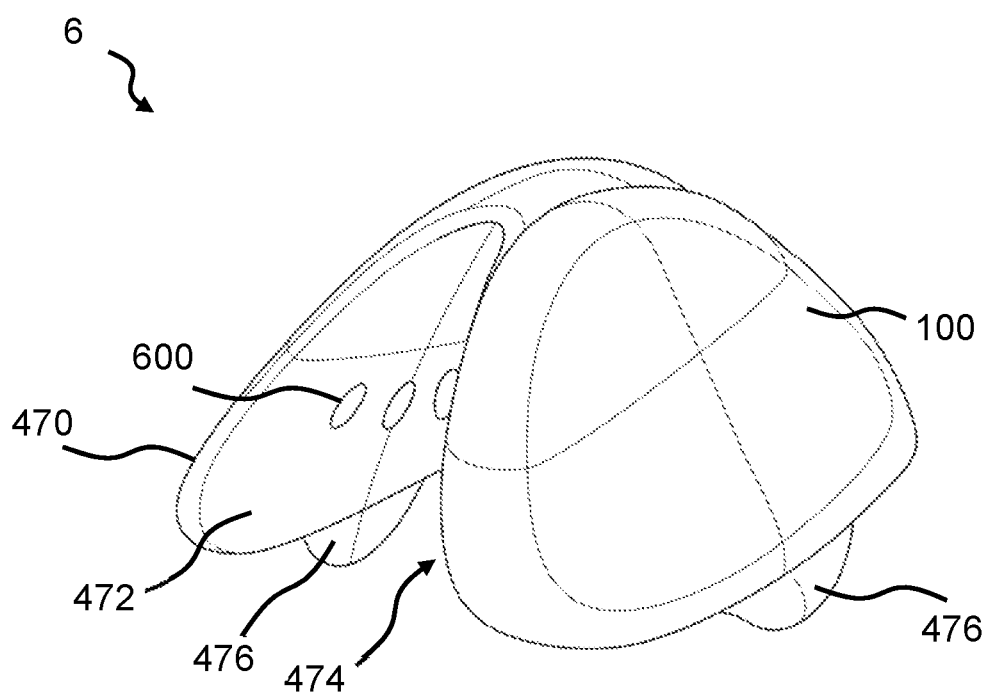

FIG. 24 schematically illustrates an exemplary monitor device 6, such as the monitor device as illustrated in FIG. 2. The monitor device 6 is comprises a monitor device housing 100, and a plurality of terminals 600 for connecting with a plurality of electrodes of the base plate. The monitor device 6 further comprise a monitor device coupling part configured for coupling between the monitor device 6 and a base plate. The monitor device coupling part and the plurality of terminals 600 (one or more of terminals 108, 110, 112, 114, 116, 118 of FIG. 2) may form part of an appliance interface of the monitor device 6.

The monitor device 6 comprises a locking mechanism configured to engage with a locking section of the base plate to lock the monitor device 6 in a coupled position with the base plate. The monitor device 6 comprises a clamp 470 configured to clamp a coupling part of the base plate between a first clamp surface 472 and a second clamp surface 474

The locking mechanism may comprise a locking component (not shown) positioned between the first clamp surface 472 and the second clamp surface 474. The locking component may be configured to engage with the locking section of the base plate. For example, the locking component may be a pin configured to engage a hole of the locking section of the base plate.

The plurality of terminals 600 is provided on the first clamp surface 472. The plurality of terminals 600 may additionally and/or alternatively be provided on the second clamp surface 472.

The first clamp surface 472 and the second clamp surface 474 may be biased towards each other, e.g. spring biased or magnetically biased. Alternatively, the first clamp surface 472 and the second clamp surface 474 may be biased away from each other, e.g. spring biased or magnetically biased. The monitor device 6 comprises a clamp lock 476 configured to lock the first clamp surface 472 and the second clamp surface 474 in a closed clamp position. The clamp lock 476 may be configured to be unlocked by user interaction.

Figure 25:
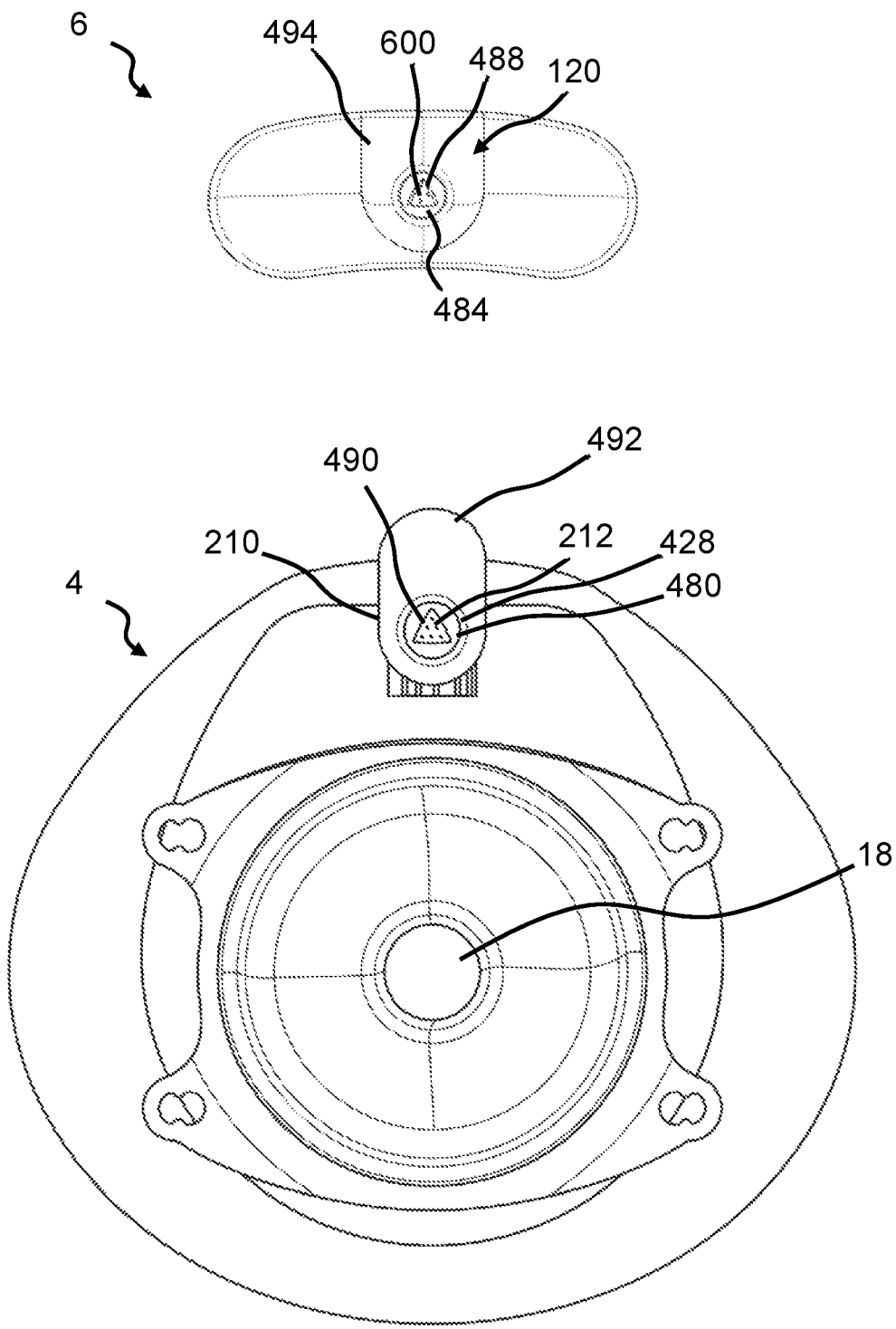
Figure 26:
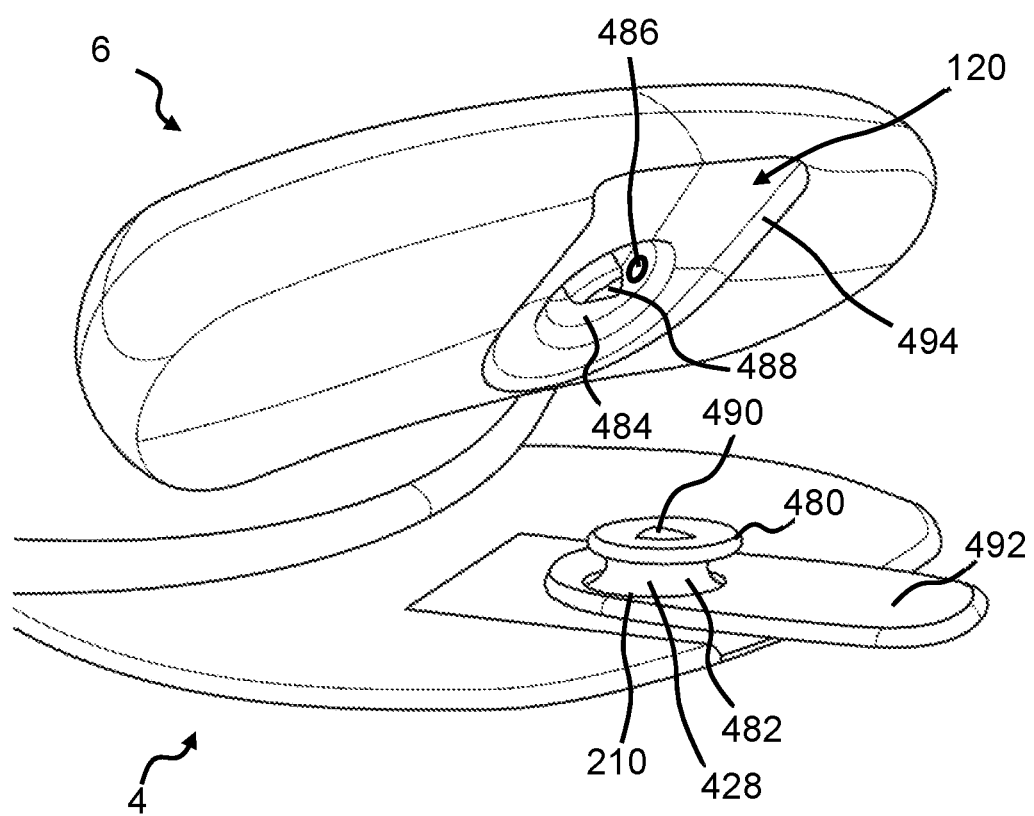

FIGS. 25 and 26 schematically illustrates an exemplary base plate 4, such as the base plate as illustrated in FIG. 11a or FIG. 11b, and a monitor device 6, such as the monitor device as illustrated in FIG. 2. FIG. 26 only show part of the exemplary base plate 4.

The base plate 4 comprises a coupling part 210. The coupling part 210 comprises a protruding part 480. The protruding part 480 has concave sides 482, e.g. the protruding part 480 may be substantially a cylinder with a concave side wall. The protruding part 480 and/or the concave sides 482 form a locking section 428 of the coupling part 210.

The monitor device coupling part 120 comprises a cavity 484. The cavity 484 is configured to receive the protruding part 480, and the protruding part 480 is configured to engage with the cavity 484. The monitor device coupling part 120 comprises one or more deflectable elements 486 positioned on the sides of the cavity 484. The deflectable elements 486 form part of the locking mechanism of the monitor device 6 and are configured to engage with the concave sides 482 of the protruding part 480. Thereby the protruding part 480 may be retained in the cavity 484.

Furthermore, the monitor device coupling part 120 comprises a protruding element 488 being positioned substantially in the centre of the cavity 484. The protruding part 480 of the coupling part 210 comprise a corresponding socket 490 configured to receive the protruding element 488. The protruding element 488 and the socket 490 have triangular cross sections to limit the possible orientations for engagement and to ensure correct coupling of the monitor device 6 to the base plate 4.

The plurality of terminals 600 of the monitor device 6 is provided on the end of the protruding element 488, and the plurality of terminals 212 of the base plate 4 is provided in the bottom of the socket 490.

It is furthermore illustrated that the monitor device 6 is curved to indicate to the user the correct way of orientating the monitor device 6. The curvature of the monitor device 6 is curved to have a concave side configured to face the ostomy opening 18 of the base plate 4.

The coupling part 210 further comprises a first alignment element 492, and the monitor device coupling part 120 comprises a second alignment element 494. The protruding part 480 is positioned on top of the first alignment element 492. The first alignment element 492 and the second alignment element 494 are configured to engage for further ensuring correct alignment of the monitor device 6 relative to the base plate 4. The first alignment element 492 forms a first alignment edge configured to be received by the second alignment element 494 forming a depression with a second alignment edge. The second alignment element 494 has an open end towards a rim surface of the monitor device 6, and a closed opposite end, to ensure that the first alignment element 492 is only able to be received in the second alignment element 494 when the monitor device 6 is orientated correctly, e.g. when the concave side of the monitor device 6 is facing the stomal opening 18.

Figure 27:
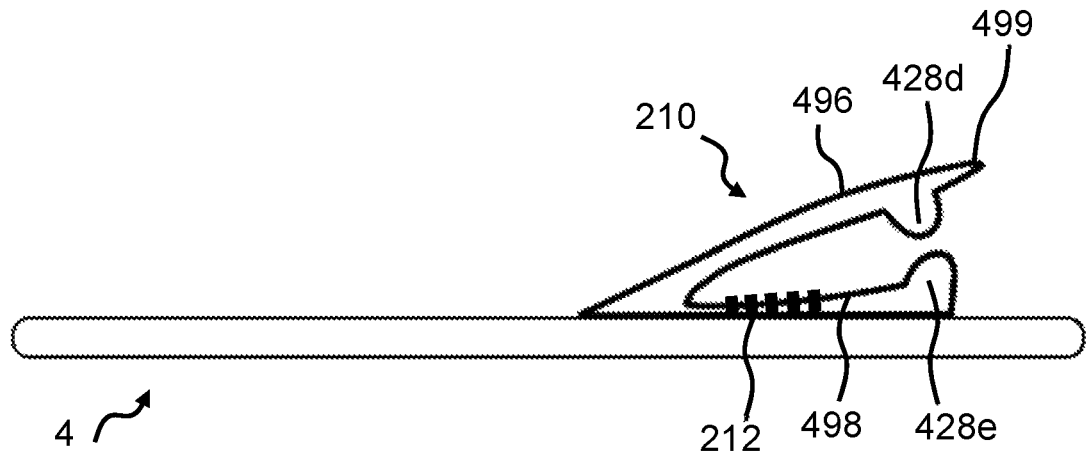
Figure 28:
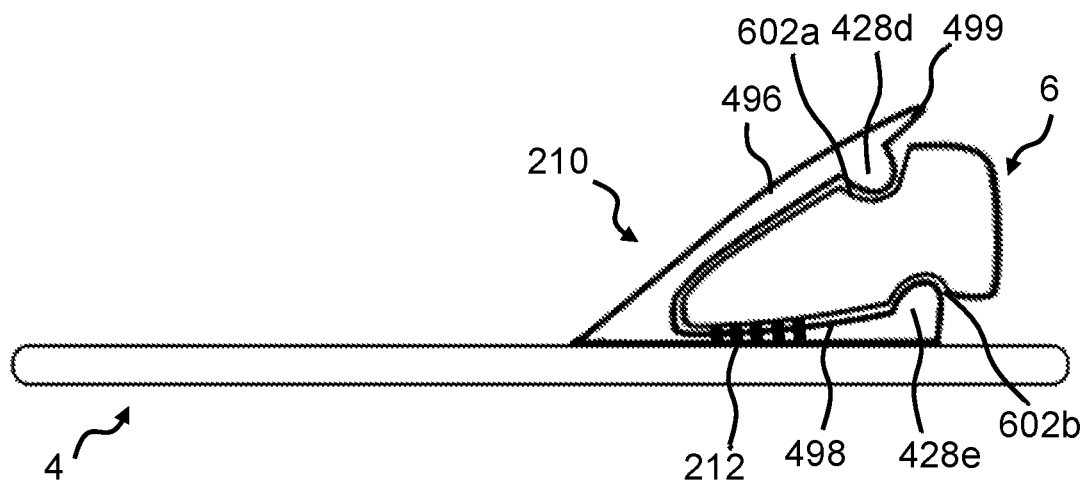

FIGS. 27 and 28 schematically illustrates an exemplary base plate 4, such as the base plate as illustrated in FIG. 11a or FIG. 11b. The base plate 4 comprises a coupling part 210 comprising a first coupling part section 496 and a second coupling part section 498. The coupling part 210 is configured to receive at least a part of the monitor device 6 between the first coupling part section 496 and the second coupling part section 498, as illustrated in FIG. 28. The first coupling part section 496 and the second coupling part section 498 are biased towards each other, e.g. by the elastic property of the coupling part 210 and/or by spring means. In the illustrated example, the first coupling part section 496 is deflectable from the second coupling part section 498. The first coupling part section 496 comprises a lever 499 to allow a user to bend the first coupling part section 496 away from the second coupling part section 498, such as to release the monitor device 6 from the coupling part 210. The monitor device 6 is wedge shaped to allow easy insertion between the first coupling part section 496 and the second coupling part section 498.

The coupling part 210 comprises a locking section 428 comprising a first protrusion 428d protruding from the first coupling part section 496 and a second protrusion 428e protruding from the second coupling part section 498. The monitor device 6 may comprise corresponding indents 602, such as a first indent 602a to receive the first protrusion 428d and a second indent 602b to receive the second protrusion 428e.

The plurality of terminals 212 of the base plate 4 is provided in coupling part 210, such as between the first coupling part section 496 and the second coupling part section 498.

Figure 29:
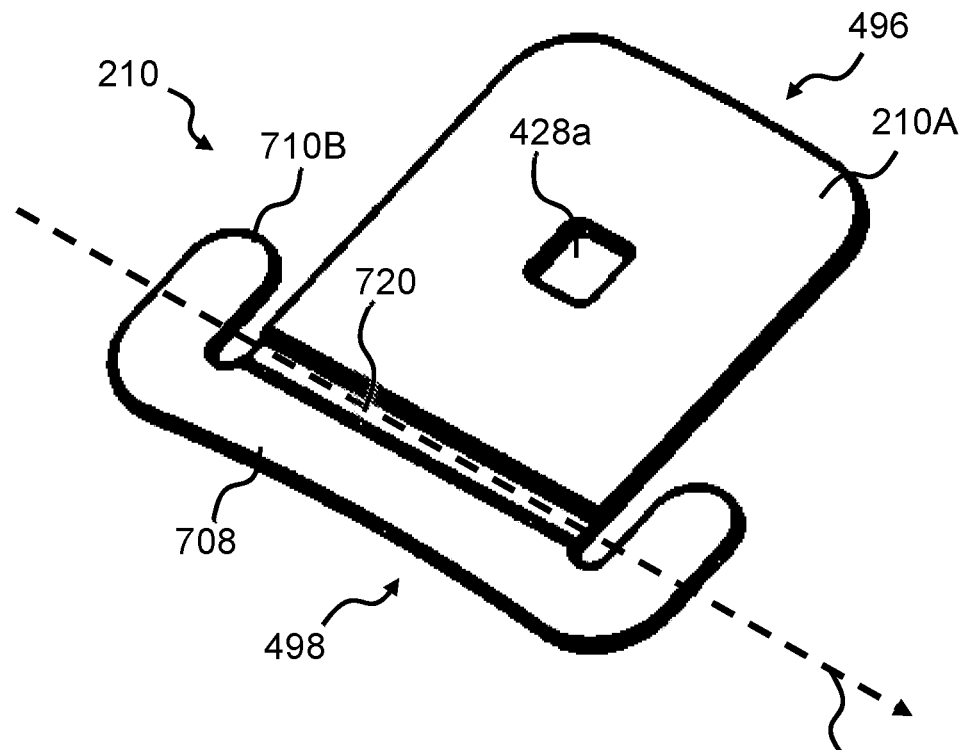

FIG. 29 schematically illustrates an exemplary coupling part 210, e.g. the distal side 210A of the coupling part 210, comprising a first coupling part section 496 and a second coupling part section 498. As seen, the first coupling part section 496 and the second coupling part section are substantially planar. The first coupling part section 496 is configured for attachment to a first part of the base plate, such as the first part 302 of the electrode assembly, e.g. as explained in relation to FIGS. 15-21. The second coupling part section 496 is configured for attachment to a second part of the base plate, such as a second part of a top layer of the base plate.

The first coupling part section 496 is hingedly attached to the second coupling part section 498. Thereby allowing rotational movement of the first coupling part section 496 relative to the second coupling part section 498 about a hinge-axis 702. The hinge axis 702 is parallel to the first coupling part section 496 and the second coupling part section 498.

For example, with reference to FIG. 17, the coupling part 210 of FIG. 29 may be attached to top layer 208 prior to turning over the first part 302 of the electrode assembly, such that the first coupling part section 496 is attached to a first part of the top layer 208 above the first part 302 of the electrode assembly, and such that the second coupling part section 498 is attached to a second part of the top layer 208 not being turned over. The hinged attachment between the first coupling part section 496 and the second coupling part section 498 allows the first part 302 of the electrode assembly to be lifted, together with the first coupling part section 496, to allow access to the distal side of the electrode assembly with the connection parts 217.

The coupling part 210 comprises a line 720 of reduced thickness along the hinge-axis 754 allowing the rotational movement of the first coupling part section 496 relative to the second coupling part section 498 about the hinge-axis. The line 720 of reduced thickness is provided on the distal side of the coupling part 210 such as to allow for rotation of the first coupling part section in a distal direction. The flexibility providing for the hingedly attachment between the first coupling part section 496 and the second coupling part section 498 may be provided by other means, such as described with respect to FIGS. 30 and 31.

The second coupling part section 498 comprises a primary second coupling part section 708 and two secondary second coupling part sections 710A; 710B. In another exemplary coupling part (not shown) the second coupling part section 498 comprises only one secondary second coupling part section, e.g. extending all the way along the periphery of the first coupling part section 496.

The primary second coupling part section 708 is located on a primary side of the hinge-axis. The secondary second coupling parts sections 710A; 710B are located on a secondary side of the hinge-axis 754, opposite the primary side of the hinge-axis 754. Thereby, the second coupling part section 498 provides increased stability of the coupling part 210 when rotating the first coupling part section 496 about the hinge-axis 754.

The coupling part 210, such as the first coupling part section 496 of the coupling part 210, comprises a locking section comprising a hole 428a. The locking section 428a is configured to lock a monitor device in a coupled position with the base plate. The hole 428a extends through the coupling part 210, e.g. through the first coupling part section 496. A locking mechanism of the monitor device may comprise a locking component, e.g. a pin, positioned inside an opening for receiving the coupling part 210, and being configured to protrude through the hole 428a.

Figure 30:
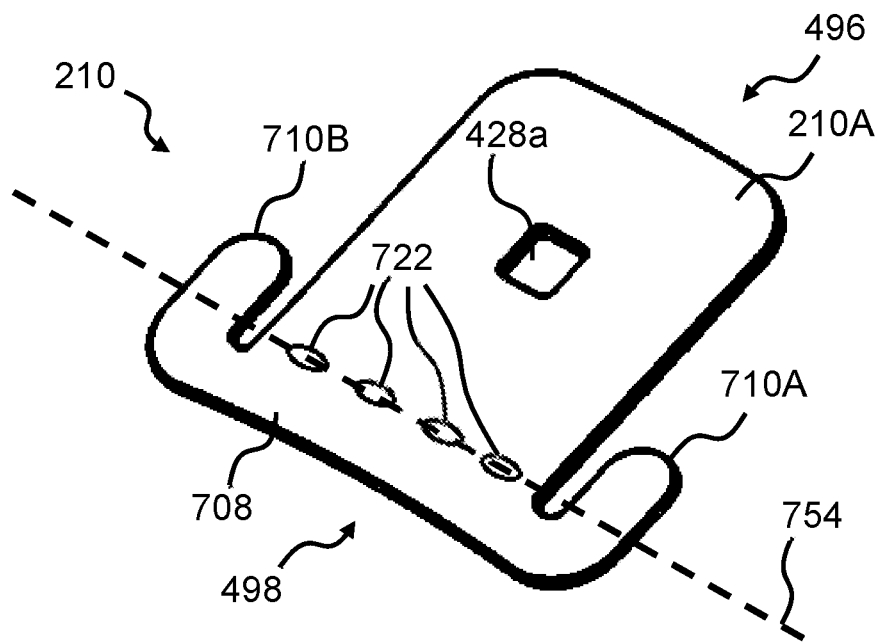

FIG. 30 schematically illustrates an exemplary coupling part 210 similar to the exemplary coupling part 210 of FIG. 29. However, with the difference that the hingedly attachment between the first coupling part section 496 and the second coupling part section 498 is provided by providing holes 722 in the coupling par 210 along the hinge-axis 754. The holes 722 along the hinge-axis 754 allows the rotational movement of the first coupling part section 496 relative to the second coupling part section 498 about the hinge-axis 754.

FIGS. 31a and 31b schematically illustrates an exemplary coupling part 210 similar to the exemplary coupling part 210 of FIG. 29. However, with the differences that the coupling part 210 of FIGS. 31a and 31b is made from laminating a plurality of laminates 724; 726; 728 and that the hingedly attachment between the first coupling part section 496 and the second coupling part section 498 is provided by the laminate layers 724; 726; 728.

FIG. 31a shows an exploded view of the exemplary coupling part 210, showing the laminated layers making up the coupling part 210. The coupling part 210 is made of a first laminate 724 being laminated with a second laminate 726, and a third laminate 728 being laminated with the second laminate 726 and the first laminate 724. The laminating process may be provided in several steps, e.g. the first laminate 724 may be laminated with the second laminate 726 in a first step, and optionally cut to a certain shape, before being laminated with the third laminate 728. After laminating the laminates 724; 726; 728, the coupling part 210 may be cut or stamped out.

FIG. 31b shows the exemplary coupling part 210. As is seen the hinged attachment between the first coupling part section 496 and the second coupling part section 498 is provided by letting only the third laminate 728 extend across the hinge-axis. The third laminate 728 may be chosen to have a thickness thin enough to allow rotation of the first coupling part section 496 relative to the second coupling part section 498. Also, the material of the third laminate may be chosen to be a non-rigid material. The first laminate 724 and the second laminate 726 may provide increased strength to the first coupling part section 496.

FIG. 32 schematically illustrates an exemplary coupling part 210, such as the coupling part 210 of any of FIGS. 29-31, seen from the side. As shown, the first coupling part section 496 is substantially planar in a first coupling part plane 750 and the second coupling part section 498 is substantially planar in a second coupling part plane 752. Thus, the hinge-axis 754 (see FIG. 29-31) is parallel to the first coupling part plane 750 and the second coupling part plane 752.

To facilitate easier coupling of the monitor device to the coupling part 210, the coupling part 210 may be configured such that the first coupling part section 496 is biased towards a position where it is lifted a small amount from the base plate. Thus, in a resting state, i.e. a state wherein no force is applied to the first coupling part, e.g. a state where no pressure is applied to the distal side of the first coupling part section 496, the first coupling part section and the second coupling part section forms a resting angle 756. The resting angle may be more than 5 degrees, such as more than 10 degrees, such as more than 15 degrees, such as more than 20 degrees.

Also illustrated in FIG. 32 is that the coupling part 210 comprises adhesives 712; 714 for attachment to the layers of a base plate, such as to a top layer of the base plate. For example, the first coupling part section 496 comprises a first coupling part section adhesive 712 configured for attachment to the first part of the base plate, such as the first part of the electrode assembly. The second coupling part section 498 comprises a second coupling part section adhesive 714 configured for attachment to a second part of the base plate, such as a second part of the top layer. Alternatively, the first coupling part section 496 and/or the second coupling part section 498 may be welded to their respective parts of the base plate.

The first coupling part section 496 has a first coupling part thickness 716 and the second coupling part section has a second coupling part thickness 718. The first coupling part thickness 716 and the second coupling part section 718 may be the same. Alternatively, the first coupling part thickness may be more than the second coupling part section 718, e.g. as is the case for the exemplary coupling part 210 illustrated in FIG. 31b. For example, the first coupling part thickness may be 0.6 mm and the second coupling part thickness may be 0.3 mm.

Figure 33:
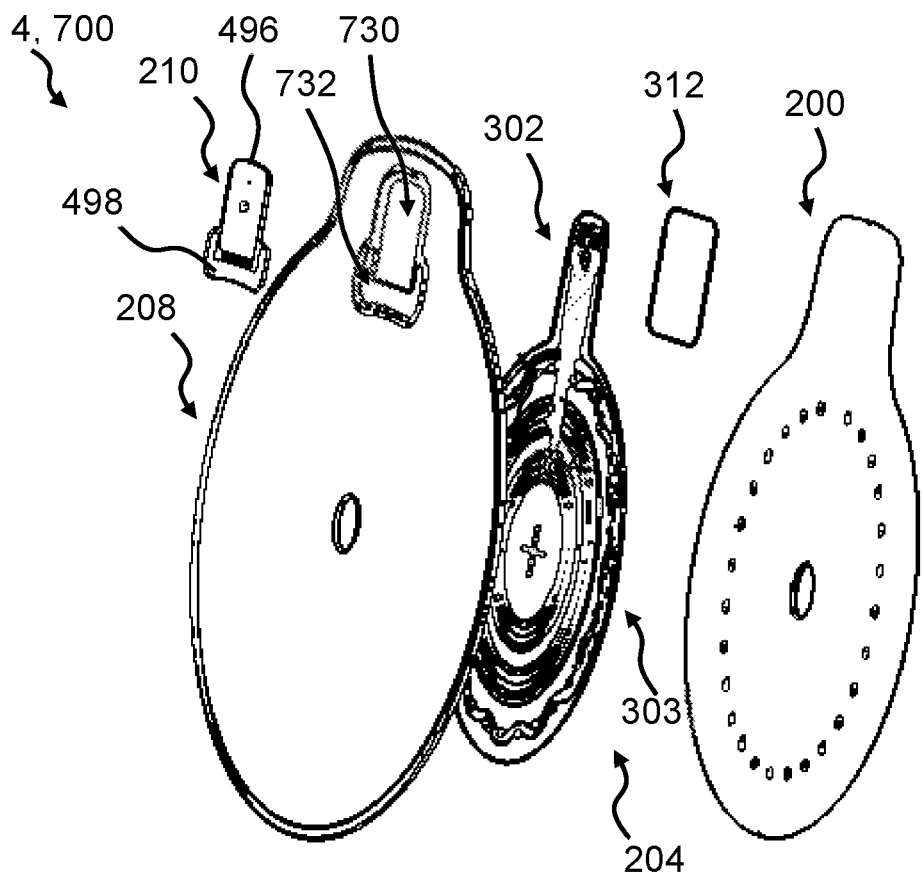

FIG. 33 schematically illustrates an exploded view of an exemplary base plate 4 and/or a sensor assembly part 700, such as a base plate 4 and/or a sensor assembly part 700 for an ostomy appliance as also described in relation to previous figures. The base plate 4 and/or the sensor assembly part 700 comprises a top layer 208, a first adhesive layer 200, and an electrode assembly 204. The electrode assembly 204 comprises a plurality of electrodes having connection parts and sensing parts. However, although visible on FIG. 33 it will be understood that the electrodes of the electrode assembly 204 are located on the proximal side of the electrode assembly 204, i.e. facing the first adhesive layer 200.

The first adhesive layer 200 is closest to the skin, i.e. the most proximal layer of the shown layers. The top layer 208 is the most distal layer of the shown layers.

The base plate 4 and/or the sensor assembly part 700 also comprises a monitor interface for connecting the base plate 4 and/or the sensor assembly part 700 to a monitor device (see e.g. FIGS. 22 and 23). The monitor interface comprises a coupling part 210, as exemplified and described in relation to any of FIGS. 29-32. The coupling part 210 is configured for coupling between the monitor device and the base plate 4 and/or the sensor assembly part 700.

The first coupling part section 496 of the coupling part 210 is attached to a first part of the base plate and/or the sensor assembly part comprising the connection parts of the plurality of electrodes, such as the first part 302 of the electrode assembly 204 and/or a first part 730 of the top layer 208. A hole may be provided in the top layer 208 and the second adhesive layer if present, such as to allow direct attachment between the first coupling part section 496 and the first part 302 of the electrode assembly 204. Alternatively, U-shaped contour may be cut around the first part 730 of the top layer 208, such that the attached first coupling part section 496, first part 730 of the top layer 208, and the first part 302 of the electrode assembly may be rotationally movable about the hinge-axis. The first coupling part section 496 may be attached to the first part 730 of the top layer 208 and/or to the first part 302 of the electrode assembly 204 by a first coupling part section adhesive or by welding together the first coupling part section 496 and the first part 730 of the top layer 208 and/or to the first part 302 of the electrode assembly 204.

A back element 312 is provided between the first part 302 of the electrode assembly 204 and the first adhesive layer 200, such as between the proximal side of the first part 302 of the electrode assembly 204 and the distal side of the first adhesive layer 200. The back element 312 facilitates that the first part 302 of the electrode assembly is not adhering to the first adhesive layer 200, such as to allow the first part 302 of the electrode assembly 204 (e.g. together with the first coupling part section) to be turned. The back element 312 may further provide a stop for a stamping process for providing the hole or U-shaped cut in the top layer 208.

The second coupling part section 498 is attached to a second part of the base plate and/or the sensor assembly part, such as a second part 732 of the top layer 208. The second coupling part section 498 may be attached to the second part 732 of the top layer 208 by a second coupling part section adhesive or by welding together the second coupling part section 498 and the second part 732 of the top layer 208.

When attached to the top layer 208, the second coupling part section 498 may be parallel to the top layer 208. Hence, the resting angle 756 as described in relation to FIG. 32 may be formed between the first coupling part section 496 and the top layer 208.

Although not specifically shown in FIG. 33, the base plate 4 and/or the sensor assembly part 700 may comprise additional layers, such as those shown in FIG. 11a.

Figure 34:
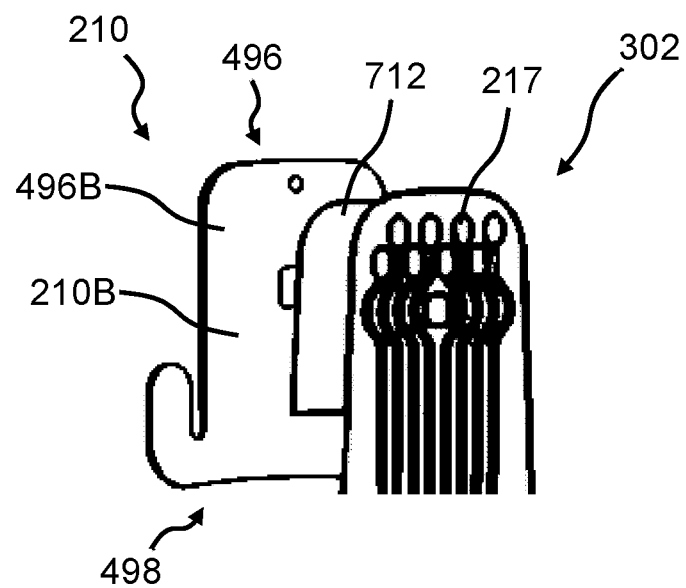

FIG. 34 schematically illustrates an exemplary coupling part 210, e.g. the proximal side 210B of the coupling part 210, and an exemplary first part 302 of an electrode assembly, as described in relation to previous figures, e.g. FIG. 33. FIG. 34 illustrates a first coupling part section adhesive 712 being positioned between the first coupling part section 496 and the first part 302 of the electrode assembly. The first coupling part section adhesive 712 is provided between the proximal side 496B of the first coupling part section 496 and a distal side of the first part 302 of the electrode assembly, such as to attach the proximal side 496B of the first coupling part section 496 to the distal side of the first part 302 of the electrode assembly.

The position of the first connector on the base plate and/or the sensor assembly part, the number of terminals and the position of the terminals in the coupling part may be adapted to the electrode configuration used in the electrode assembly of the base plate and/or the sensor assembly part.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering.

Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

Exemplary base plates and monitor devices are set out in the following items:

Item 1. A base plate for an ostomy appliance, the base plate comprising:
- a top layer;
- a first adhesive layer;
- an electrode assembly comprising a plurality of electrodes; and
- a monitor interface configured for connecting the base plate to a monitor device, the monitor interface comprising a plurality of terminals electrically connected to the plurality of electrodes and configured to connect with respective terminals of the monitor device and the monitor interface comprising a coupling part configured for coupling between the monitor device and the base plate, wherein the plurality of terminals is provided on the coupling part, and wherein the coupling part comprises a locking section configured to lock the monitor device in a coupled position with the base plate.

Item 2. Base plate according to item 1, wherein the locking section comprises a hole extending through the coupling part.

Item 3. Base plate according to any of the preceding items, wherein the locking section comprises a protrusion protruding from a surface of the coupling part.

Item 4. Base plate according to any of the preceding items, wherein the locking section comprises an indent of an edge of the coupling part and/or a recess in a surface of the coupling part.

Item 5. Base plate according to any of the preceding items, wherein the coupling part comprises a first surface and a second surface, the second surface being opposite the first surface, the second surface facing the top layer.

Item 6. Base plate according to item 5, wherein the plurality of terminals is provided on the second surface of the coupling part.

Item 7. Base plate according to any of items 5-6, wherein the second surface of the coupling part and the top layer are separated to allow at least a part of the monitor device to be positioned between the second surface of the coupling part and the top layer when the monitor device is connected to the base plate.

Item 8. Base plate according to any of the preceding items, wherein the coupling part is substantially flat.

Item 9. Base plate according to any of the preceding items, wherein the coupling part comprises a first coupling part section and a second coupling part section, wherein the coupling part is configured to receive at least a part of the monitor device between the first coupling part section and the second coupling part section.

Item 10. Base plate according to item 9, wherein the first coupling part section and the second coupling part section are biased towards each other.

Item 11. Base plate according to any of the preceding items, wherein the coupling part comprises a protruding part protruding in a protruding direction being substantially perpendicular to a base plate plane, the protruding part having concave sides forming the locking section of the coupling part, the protruding part being configured to engage with a cavity of the monitor device.

Item 12. Base plate according to item 11, wherein the protruding part comprises a socket configured to receive a protruding element positioned in the cavity of the monitor device.

Item 13. Base plate according to item 12, wherein the socket has a triangular cross section.

Item 14. A monitor device for connecting to a base plate of an ostomy appliance, the monitor device comprising:
 a monitor device housing;
 electronic circuitry; and
 an appliance interface configured for connecting the monitor device to the base plate, the appliance interface comprises a plurality of terminals for connecting with a plurality of electrodes of the base plate, the appliance interface comprises a monitor device coupling part configured for coupling between the monitor device and the base plate;
wherein the monitor device comprises a locking mechanism configured to engage with a locking section of the base plate to lock the monitor device in a coupled position with the base plate.

Item 15. Monitor device according to item 14, wherein the monitor device coupling part is configured to engage with the base plate by a linear motion in an engagement direction of the monitor device relative to the base plate.

Item 16. Monitor device according to any of items 14-15, wherein the locking mechanism is biased towards locking of the locking mechanism.

Item 17. Monitor device according to any of items 14-16 comprising a locking element configured to unlock or lock the locking mechanism upon user interaction with the locking element.

Item 18. Monitor device according to item 17 as dependent on item 15, wherein the locking element comprises a first button being deflectable in a first direction, wherein the first direction is substantially parallel or perpendicular to the engagement direction.

Item 19. Monitor device according to item 17, wherein the locking element comprises a first button and a second button, the first button being deflectable in a first direction and the second button being deflectable in a second direction, wherein the first direction is substantially opposite the second direction.

Item 20. Monitor device according to item 19 as dependent on item 15, wherein the first direction and the second direction are substantially perpendicular to the engagement direction.

Item 21. Monitor device according to any of items 17-20, wherein the locking element comprises a slider being slidable in a first slider direction, and wherein the slider is spring loaded and biased towards a second slider direction, wherein the first slider direction is opposite the second slider direction.

Item 22. Monitor device according to item 21 as dependent on item 15, wherein the first slider direction and the second slider direction are substantially perpendicular to the engagement direction.

Item 23. Monitor device according to any of items 14-22 comprising an opening for receiving a coupling part of the base plate, and wherein the locking mechanism comprises a locking component positioned inside the opening.

Item 24. Monitor device according to item 14-22 comprising a clamp configured to clamp a coupling part of the base plate between a first clamp surface and a second clamp surface, and wherein the locking mechanism comprises a locking component positioned between the first clamp surface and the second clamp surface.

Item 25. Monitor device according to item 24, wherein the plurality of terminals is provided on the first clamp surface.

Item 26. Monitor device according to any of items 24-25, wherein the first clamp surface and the second clamp surface is biased towards each other.

Item 27. Monitor device according to any of items 24-26 comprising a clamp lock configured to lock the first clamp surface and the second clamp surface in a closed clamp position.

Item 28. Monitor device according to item 27, wherein the clamp lock is configured to be unlocked by user interaction.

Item 29. Monitor device according to any of items 11-28, wherein the monitor device coupling part comprises a cavity and one or more deflectable elements positioned in the cavity, the cavity being configured to receive a protruding part of the base plate, and the deflectable elements forming part of the locking mechanism being configured to engage with concave sides of the protruding part.

Item 30. Monitor device according to item 29, wherein the monitor device coupling part comprises a protruding element being positioned in the cavity.

Item 31. Monitor device according to item 30, wherein the protruding element has a triangular cross section.

Item 32. Monitor device according to any of items 30-31, wherein the plurality of terminals is provided on the protruding element.

Further exemplary embodiments of the disclosure are set out in the following second items:

Second item 1. A coupling part for a base plate and/or a sensor assembly part for an ostomy appliance, the coupling part comprising a first coupling part section and a second coupling part section, the first coupling part section being substantially planar in a first coupling part plane and the second coupling part section being substantially planar in a second coupling part plane,
 the first coupling part section being configured for attachment to a first part of the base plate and/or sensor assembly part;
 the second coupling part section being configured for attachment to a second part of the base plate and/or sensor assembly part;
 the first coupling part section being hingedly attached to the second coupling part section allowing a rotational movement of the first coupling part section relative to the second coupling part section about a hinge-axis;
 the hinge axis being parallel to the first coupling part plane and the second coupling part plane.

Second item 2. Coupling part according to second item 1, wherein in a resting state the first coupling part section and the second coupling part section forms a resting angle, wherein the resting state is a state wherein no force is applied to the first coupling part.

Second item 3. Coupling part according to second item 2, wherein the resting angle is more than 5 degrees, such as more than 10 degrees, such as more than 15 degrees, such as more than 20 degrees.

Second item 4. Coupling part according to any of the preceding second items, wherein the second coupling part section comprises a primary second coupling part section and one or more secondary second coupling part sections, wherein the primary second coupling part section is located on a primary side of the hinge-axis, and wherein the one or more secondary second coupling part sections are located on a secondary side of the hinge-axis, wherein the secondary side of the hinge-axis is opposite the primary side of the hinge-axis.

Second item 5. Coupling part according to any of the preceding second items, wherein the first coupling part section comprises a locking section configured to lock a monitor device in a coupled position with the base plate and/or the sensor assembly part.

Second item 6. Coupling part according to second item 5, wherein the locking section comprises a hole extending through the first coupling part section.

Second item 7. Coupling part according to any of the preceding second items, wherein the first coupling part section is configured for attachment to a distal side of the first part of the base plate and/or the sensor assembly part.

Second item 8. Coupling part according to any of the preceding second items, wherein the second coupling part section is configured for attachment to a distal side of the second part of the base plate and/or the sensor assembly part.

Second item 9. Coupling part according to any of the preceding second items, wherein the first coupling part section comprises a first coupling part section adhesive configured for attachment to the first part of the base plate and/or the sensor assembly part.

Second item 10. Coupling part according to any of the preceding second items, wherein the second coupling part section comprises a second coupling part section adhesive configured for attachment to the second part of the base plate and/or the sensor assembly part.

Second item 11. Coupling part according to any of the preceding second items, wherein the first coupling part section has a first coupling part thickness and the second coupling part section has a second coupling part thickness, the first coupling part thickness and/or the second coupling part thickness being less than 2 mm, such as less than 1 mm, such as 0.6 mm.

Second item 12. Coupling part according to second item 11, wherein the first coupling part thickness is more than the second coupling part thickness.

Second item 13. Coupling part according to any of the preceding second items comprising one or more lines of reduced thickness along the hinge-axis allowing the rotational movement of the first coupling part section relative to the second coupling part section about the hinge-axis.

Second item 14. Coupling part according to second item 13, wherein the one or more lines of reduced thickness is provided on a distal side of the coupling part.

Second item 15. Coupling part according to any of the preceding second items comprising one or more holes along the hinge-axis allowing the rotational movement of the first coupling part section relative to the second coupling part section about the hinge-axis.

Second item 16. A base plate for an ostomy appliance, the base plate comprising:
 a top layer;
 a first adhesive layer;
 an electrode assembly comprising a plurality of electrodes having connection parts and sensing parts; and
 a monitor interface configured for connecting the base plate to a monitor device, the monitor interface comprising a coupling part configured for coupling between the monitor device and the base plate,
wherein the coupling part comprises a first coupling part section and a second coupling part section, the first coupling part section being substantially planar in a first coupling part plane and the second coupling part section being substantially planar in a second coupling part plane,
the first coupling part section being attached to a first part of the base plate comprising the connection parts of the plurality of electrodes,
the second coupling part section being attached to a second part of the base plate, the first coupling part section being hingedly attached to the second coupling part section allowing a rotational movement of the first coupling part section relative to the second coupling part section about a hinge-axis,
the hinge axis being parallel to the first coupling part plane and the second coupling part plane.

Second item 17. Base plate according to second item 16, wherein a proximal side of the second coupling part section is attached to a distal side of a second part of the top layer.

Second item 18. Base plate according to any of second items 16 or 17, wherein a proximal side of the first coupling part section is attached to a distal side of a first part of the top layer.

Second item 19. Base plate according to any of second items 16 or 17, wherein a proximal side of the first coupling part section is attached to a distal side of a first part of the electrode assembly.

Second item 20. Base plate according to any of second items 16-19, wherein the first coupling part section is attached to the first part of the base plate by a first coupling part section adhesive.

Second item 21. Base plate according to any of second items 16-20, wherein the first coupling part section is attached to the first part of the base plate by welding together the first coupling part section and the first part of the base plate.

Second item 22. Base plate according to any of second items 16-21, wherein the second coupling part section is attached to the second part of the base plate by a second coupling part section adhesive.

Second item 23. Base plate according to any of second items 16-22, wherein the second coupling part section is attached to the second part of the base plate by welding together the second coupling part section and the second part of the base plate.

Second item 24. Base plate according to any of second items 16-23, wherein in a resting state the first coupling part section and the top layer forms a resting angle, wherein the resting state is a state wherein no force is applied to the first coupling part.

Second item 25. Base plate according to second item 24, wherein the resting angle is more than 5 degrees, such as more than 10 degrees, such as more than 15 degrees, such as more than 20 degrees.

Second item 26. Base plate according to any of second items 16-25 comprising a back element between the first adhesive layer and the electrode assembly.

Second item 27. A sensor assembly part for an ostomy appliance, the sensor assembly part comprising:
- a top layer;
- a first adhesive layer;
- an electrode assembly comprising a plurality of electrodes having connection parts and sensing parts; and
- a monitor interface configured for connecting the sensor assembly part to a monitor device, the monitor interface comprising a coupling part configured for coupling between the monitor device and the sensor assembly part, wherein the coupling part comprises a first coupling part section and a second coupling part section, the first coupling part section being substantially planar in a first coupling part plane and the second coupling part section being substantially planar in a second coupling part plane, the first coupling part section being attached to a first part of the sensor assembly part comprising the connection parts of the plurality of electrodes, the second coupling part section being attached to a second part of the sensor assembly part, the first coupling part section being hingedly attached to the second coupling part section allowing a rotational movement of the first coupling part section relative to the second coupling part section about a hinge-axis, the hinge axis being parallel to the first coupling part plane and the second coupling part plane.

Second item 28. Sensor assembly part according to second item 27, wherein a proximal side of the second coupling part section is attached to a distal side of a second part of the top layer.

Second item 29. Sensor assembly part according to any of second items 27 or 28, wherein a proximal side of the first coupling part section is attached to a distal side of a first part of the top layer.

Second item 30. Sensor assembly part according to any of second items 27 or 28, wherein a proximal side of the first coupling part section is attached to a distal side of a first part of the electrode assembly.

Second item 31. Sensor assembly part according to any of second items 27-30, wherein the first coupling part section is attached to the first part of the sensor assembly part by a first coupling part section adhesive.

Second item 32. Sensor assembly part according to any of second items 27-31, wherein the first coupling part section is attached to the first part of the sensor assembly part by welding together the first coupling part section and the first part of the sensor assembly part.

Second item 33. Sensor assembly part according to any of second items 27-32, wherein the second coupling part section is attached to the second part of the sensor assembly part by a second coupling part section adhesive.

Second item 34. Sensor assembly part according to any of second items 27-33, wherein the second coupling part section is attached to the second part of the sensor assembly part by welding together the second coupling part section and the second part of the sensor assembly part.

Second item 35. Sensor assembly part according to any of second items 27-34, wherein in a resting state the first coupling part section and the top layer forms a resting angle, wherein the resting state is a state wherein no force is applied to the first coupling part.

Second item 36. Sensor assembly part according to second item 35, wherein the resting angle is more than 5 degrees, such as more than 10 degrees, such as more than 15 degrees, such as more than 20 degrees.

Second item 37. Sensor assembly part according to any of second items 37-36 comprising a back element between the first adhesive layer and the electrode assembly.

LIST OF REFERENCES 1 ostomy system
2 ostomy appliance
4 base plate
6 monitor device
6 accessory device
8 server device
10 network
12 coupling member
16 coupling ring
18 stoma-receiving opening
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
122 antenna
124 wireless transceiver
200 first adhesive layer
200A distal side/surface of first adhesive layer
200B proximal side/surface of first adhesive layer
202 second adhesive layer
202A distal side/surface of second adhesive layer
202B proximal side/surface of second adhesive layer
204 electrode assembly
204A distal side/surface of electrode assembly
204B proximal side/surface of electrode assembly
206 release liner
206A distal side/surface of the release liner
206B proximal side/surface of the release liner
208 top layer
208A distal side/surface of the top layer
208B proximal side/surface of the top layer
209 coupling ring
210 coupling part of first connector
210A distal side/surface of coupling part
210B proximal side/surface of coupling part
211 first connector
212 terminals of first connector
213 first intermediate element
213A distal side/surface of first intermediate element
213B proximal side/surface of first intermediate element
214 support layer of electrode assembly
214A distal side/surface of support layer
214B proximal side/surface of support layer
216 electrodes of electrode assembly
217 connection parts
218 masking element
218A distal side/surface of masking element
218B proximal side/surface of masking element
220 electrode configuration
222 ground electrode
222A ground connection part
222B ground sensing part
224 first electrode 224A first connection part
226 second electrode
226A second connection part
228 third electrode
228A third connection part
230 fourth electrode
230A fourth connection part
230B fourth sensing part
232 fifth electrode
232A fifth connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
272 terminal element(s)
272A distal end of terminal element(s)
272B proximal end of terminal element(s)
274A distal part of terminal element(s)
274B proximal part of terminal element(s)
276A distal terminal element bend
276B proximal terminal element bend
278 guide hole
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
292A fifth terminal
302 first part of electrode assembly
303 second part of electrode assembly
304 top layer opening
306 second adhesive layer opening
308 reinforcement element
308A distal side of reinforcement element
308B proximal side of reinforcement element
310 openings
311 conductive paths
312 back element
314 first elevated part
412 engagement direction
413 disengagement direction
424 opening
428 locking section
430 locking element
431 locking element protrusion
432 first direction
433 second direction
434 first slider direction
436 second slider direction
460 first surface of coupling part
462 second surface of coupling part
470 clamp
472 first clamp surface
474 second clamp surface
480 protruding part
482 concave side
484 cavity
486 deflectable element
488 protruding element
490 socket
492 first alignment element
494 second alignment element
496 first coupling part section
498 second coupling part section
499 lever
600 plurality of terminals of monitor device
602 indent
708 primary second coupling part section
710, 710A, 710B secondary second coupling part section
712 first coupling part section adhesive
714 second coupling part section adhesive
716 first coupling part thickness
718 second coupling part thickness
720 line of reduced thickness
722 hole(s)
724 first laminate
726 second laminate
728 third laminate
730 first part of top layer
732 second part of top layer
750 first coupling part plane
752 second coupling part plane
754 hinge-axis
756 resting angle
M number of terminals in the first interface of the monitor device

The invention claimed is:

1. A base plate for a medical appliance, the base plate comprising:
a top layer defining a distal side of the base plate;
a first adhesive layer comprising hydrocolloid;
an electrode assembly located between the top layer and the first adhesive layer, the electrode assembly comprising a plurality of electrodes having connection parts and sensing parts; and
a monitor interface adapted to allow a monitor device to electrically couple with the plurality of electrodes, the monitor interface comprising a coupling part comprising a first coupling part section rotatably attached to a second coupling part section;
wherein the first coupling part section is attached to a first part of the base plate provided with the connection parts of the plurality of electrodes, and the second coupling part section is attached to the top layer on the distal side of the base plate;

wherein the first coupling part section is rotatably attached to the second coupling part section by a hinge having a hinge-axis to allow the first coupling part section to rotate relative to the second coupling part section to displace the first coupling part section and the connection parts of the plurality of electrodes a distance away from the second coupling part section attached to the top layer on the distal side of the base plate.

2. The base plate according to claim 1, comprising a stomal opening formed through the top layer and the first adhesive layer, the stomal opening of the base plate being configured to allow passage of output from a stoma of a user.

3. The base plate according to claim 1, wherein a proximal side of the second coupling part section is attached to the top layer on the distal side of the base plate.

4. The base plate according to claim 1, wherein a proximal side of the first coupling part section is attached to the top layer on the distal side of the base plate.

5. The base plate according to claim 1, wherein the first coupling part section is attached to the first part of the base plate by an adhesive.

6. The base plate according to claim 1, wherein the first coupling part section is attached to the first part of the base plate by a weld.

7. The base plate according to claim 1, wherein the second coupling part section is attached to the second part of the base plate by an adhesive.

8. The base plate according to claim 1, wherein the second coupling part section is attached to the second part of the base plate by a weld.

9. The base plate according to claim 1, wherein in a resting state the first coupling part section and the top layer forms a non-zero resting angle relative to the plane of the top layer on the distal side of the base plate.

10. The base plate according to claim 9, wherein the non-zero resting angle is in a range from 5 degrees to 20 degrees.

11. The base plate according to claim 1, comprising a back element between the first adhesive layer and the electrode assembly.

12. The base plate according to claim 1, wherein the first coupling part section further comprises a hole adapted to removably engage with an engagement feature of the monitor device.

13. The base plate according to claim 1, wherein the hinge is defined by a reduced thickness along the hinge-axis.

14. The base plate according to claim 1, wherein the hinge is defined by a plurality of holes formed along the hinge-axis.

* * * * *